US009163355B2

(12) United States Patent
Suzuki et al.

(10) Patent No.: US 9,163,355 B2
(45) Date of Patent: Oct. 20, 2015

(54) HIGHLY ABSORBENT COMPOSITE AND METHOD OF MAKING THE SAME

(75) Inventors: Migaku Suzuki, Kamakura (JP); Ryoichi Matsumoto, Kunitachi (JP); Shingo Mori, Ota (JP)

(73) Assignee: DSG International Limited, Tortola (VG)

( * ) Notice: Subject to any disclaimer, the term of this patent is extended or adjusted under 35 U.S.C. 154(b) by 18 days.

(21) Appl. No.: 12/620,248

(22) Filed: Nov. 17, 2009

(65) Prior Publication Data

US 2010/0062165 A1    Mar. 11, 2010

Related U.S. Application Data

(62) Division of application No. 09/242,482, filed as application No. PCT/JP97/04606 on Dec. 15, 1997.

(30) Foreign Application Priority Data

Dec. 13, 1996 (JP) .................. 1996-333520
May 15, 1997 (JP) .................. 1997-124623
Jul. 17, 1997 (JP) .................. 1997-192159
Aug. 7, 1997 (JP) .................. 1997-213222
Nov. 14, 1997 (JP) .................. 1997-313368
Dec. 1, 1997 (JP) .................. 1997-329830

(51) Int. Cl.
*B05D 3/02* (2006.01)
*D06M 15/05* (2006.01)
(Continued)

(52) U.S. Cl.
CPC .............. *D06M 15/05* (2013.01); *A61F 13/53* (2013.01); *A61F 13/5323* (2013.01); *A61L 15/28* (2013.01); *A61L 15/60* (2013.01); *D06M 15/07* (2013.01);
(Continued)

(58) Field of Classification Search
CPC ..... D06M 15/05; D06M 15/07; D06M 23/08; D06M 23/10; D06M 23/16; A61F 13/53; A61F 13/5323; A61F 2013/530145; A61L 15/28; A61L 15/60; D21H 21/22; Y10T 428/1314; Y10T 428/1359; Y10T 428/1362; Y10T 428/1348; Y10T 428/1352; Y10T 428/139; Y10T 428/1303; Y10T 428/1386; Y10T 428/23993; Y10T 428/23936; Y10T 428/23921; Y10T 428/23929; Y10T 428/23997; C08K 7/02
USPC .......................... 427/180, 197, 201–203, 384
See application file for complete search history.

(56) References Cited

U.S. PATENT DOCUMENTS 4,425,127 A    1/1984   Suzuki et al.
4,474,949 A *  10/1984  Chatterjee et al. ............. 536/56
(Continued)

FOREIGN PATENT DOCUMENTS

EP    0 209 884 A    1/1987
EP    0 210 570 A    2/1987
(Continued)

*Primary Examiner* — Robert S Walters, Jr.
(74) *Attorney, Agent, or Firm* — Frommer Lawrence & Haug LLP

(57) ABSTRACT

A composite structure mainly composed of hydratable fine fibers in the form of microfibril and a water swellable solid body, the fibers being obtained from cellulose or derivatives thereof, and at least part of the surface of the solid body is covered with the fine fibers. The absorbent composite can be formed in various form of, for example, particle, pellet, sheet and the like, especially of a sheet type with a supporting sheet of a non-woven fabric. The present invention further provides a method of making the composite structure.

14 Claims, 48 Drawing Sheets

(51) Int. Cl.
*A61F 13/53* (2006.01)
*A61F 13/532* (2006.01)
*A61L 15/28* (2006.01)
*A61L 15/60* (2006.01)
*D06M 15/07* (2006.01)
*D06M 23/08* (2006.01)
*D06M 23/10* (2006.01)
*D06M 23/16* (2006.01)
*D21H 21/22* (2006.01)
*C08K 7/02* (2006.01)

(52) U.S. Cl.
CPC .............. *D06M 23/08* (2013.01); *D06M 23/10* (2013.01); *D06M 23/16* (2013.01); *D21H 21/22* (2013.01); *A61F 2013/530145* (2013.01); *C08K 7/02* (2013.01); *Y10T 428/13* (2015.01); *Y10T 428/1303* (2015.01); *Y10T 428/139* (2015.01); *Y10T 428/1314* (2015.01); *Y10T 428/1348* (2015.01); *Y10T 428/1352* (2015.01); *Y10T 428/1359* (2015.01); *Y10T 428/1362* (2015.01); *Y10T 428/1386* (2015.01); *Y10T 428/1393* (2015.01); *Y10T 428/23921* (2015.04); *Y10T 428/23929* (2015.04); *Y10T 428/23936* (2015.04); *Y10T 428/23979* (2015.04); *Y10T 428/23993* (2015.04); *Y10T 428/296* (2015.01)

(56) References Cited

U.S. PATENT DOCUMENTS

| | | | |
|---|---|---|---|
| 4,773,903 A | | 9/1988 | Weisman et al. |
| 4,784,892 A | | 11/1988 | Storey et al. |
| 4,837,067 A | * | 6/1989 | Carey et al. .................... 428/108 |
| 4,911,700 A | | 3/1990 | Makoui et al. |
| 5,047,456 A | | 9/1991 | Onwumere et al. |
| 5,156,902 A | * | 10/1992 | Pieper et al. .................. 428/206 |
| 5,248,524 A | * | 9/1993 | Soderlund ...................... 427/200 |
| 5,387,208 A | | 2/1995 | Ashton et al. |
| 5,436,066 A | | 7/1995 | Chen |
| 5,609,727 A | * | 3/1997 | Hansen et al. ................. 162/184 |
| 5,643,238 A | * | 7/1997 | Baker ............................ 604/368 |
| 5,651,862 A | | 7/1997 | Anderson et al. |
| 5,763,044 A | | 6/1998 | Ahr et al. |
| 5,853,867 A | * | 12/1998 | Harada et al. ............... 428/317.9 |
| 6,068,620 A | | 5/2000 | Chmielewski |

FOREIGN PATENT DOCUMENTS

| | | |
|---|---|---|
| EP | 0 719 531 A | 7/1996 |
| JP | 57-45057 | 3/1982 |
| JP | 62-2918 | 1/1987 |
| JP | 62-27413 | 2/1987 |
| JP | 62-36467 | 2/1987 |
| JP | 4-504969 | 9/1992 |
| JP | 8-50911 | 10/1996 |

* cited by examiner

FIG. 7
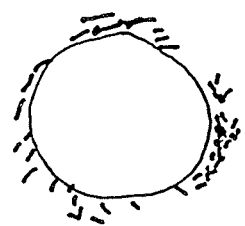
(a)
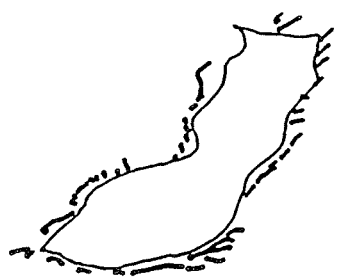
(b)
FIG. 8
(a) 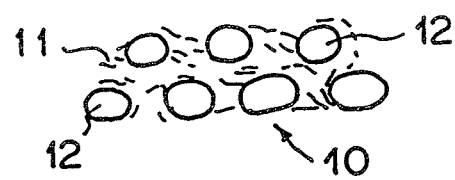
(b) 

FIG. 9
(a) 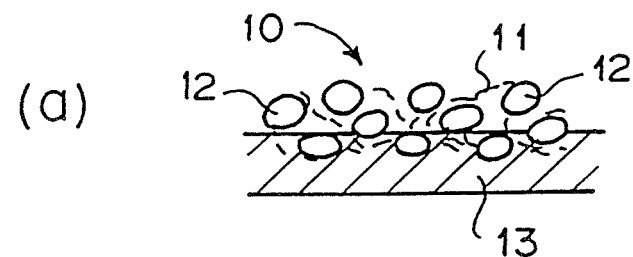
(b) 
FIG. 10
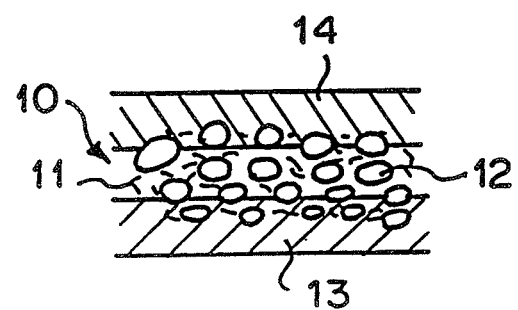

FIG. 19
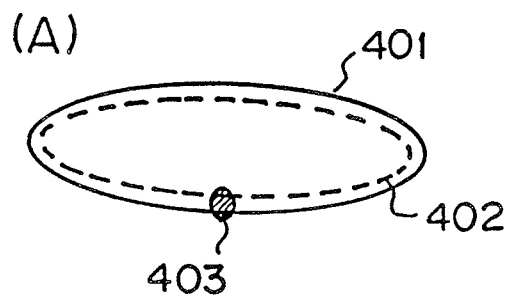
(A)
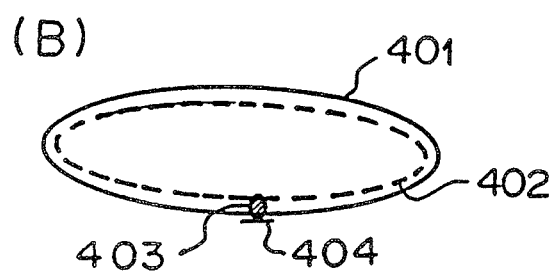
(B)
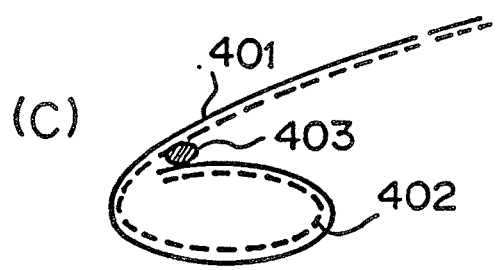
(C)
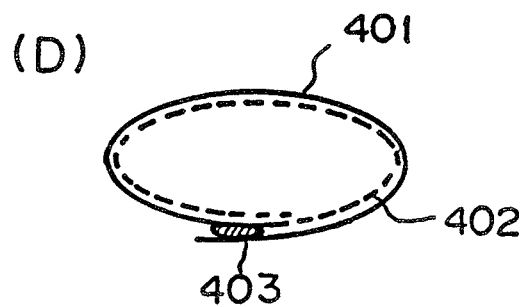
(D)

FIG. 66
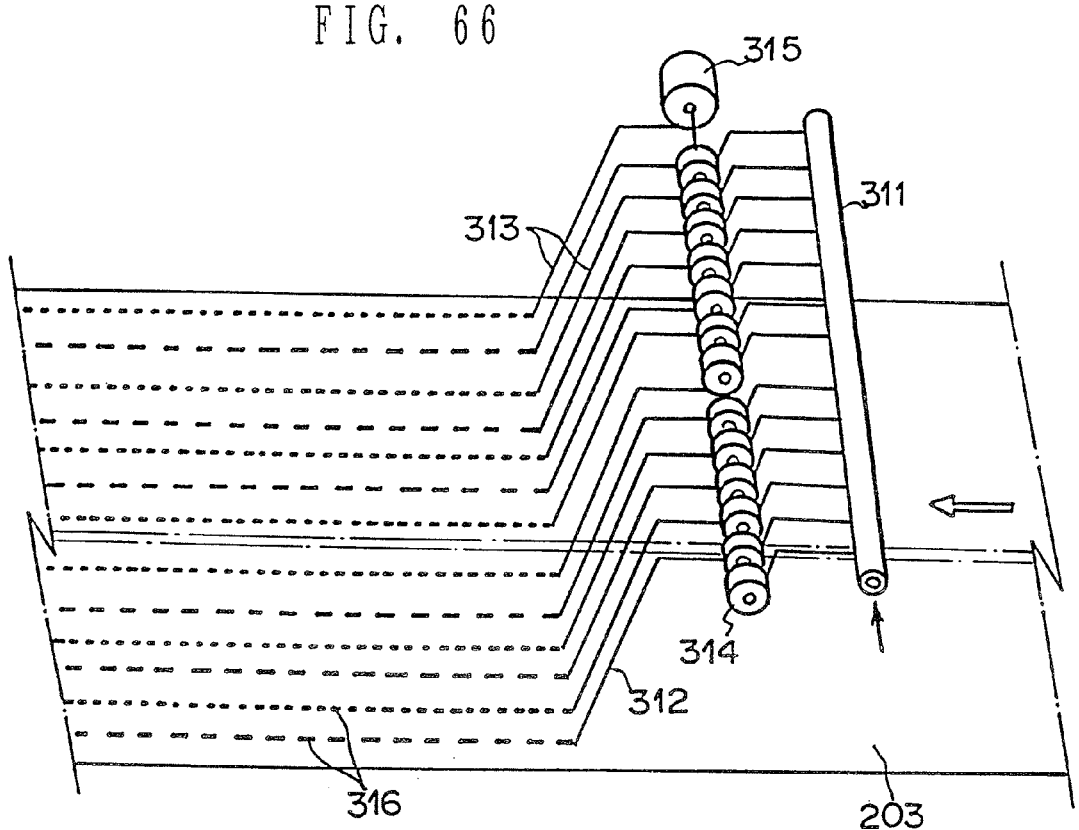
FIG. 67
(A) 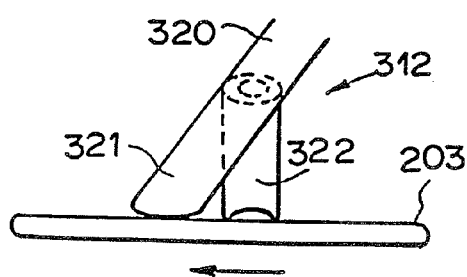
(B) 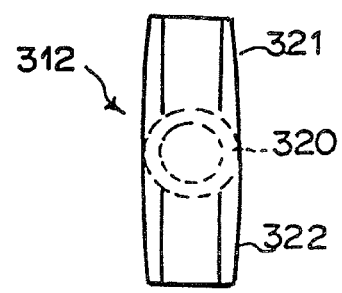

JUDGEMENT CRITERIA

| DEPOS'N STATE | ::::: | :·:·: | · · · | ·   · | (blank) |
|---|---|---|---|---|---|
| DEPOSITE AREA (%) | 80~100 | 30~60 | 10~20 | 5~1 | 0 (NO DEPOS'N) |
| GRADE | CLASS 1 | CLASS 2 | CLASS 3 | CLASS 4 | CLASS 5 |

FIG. 81
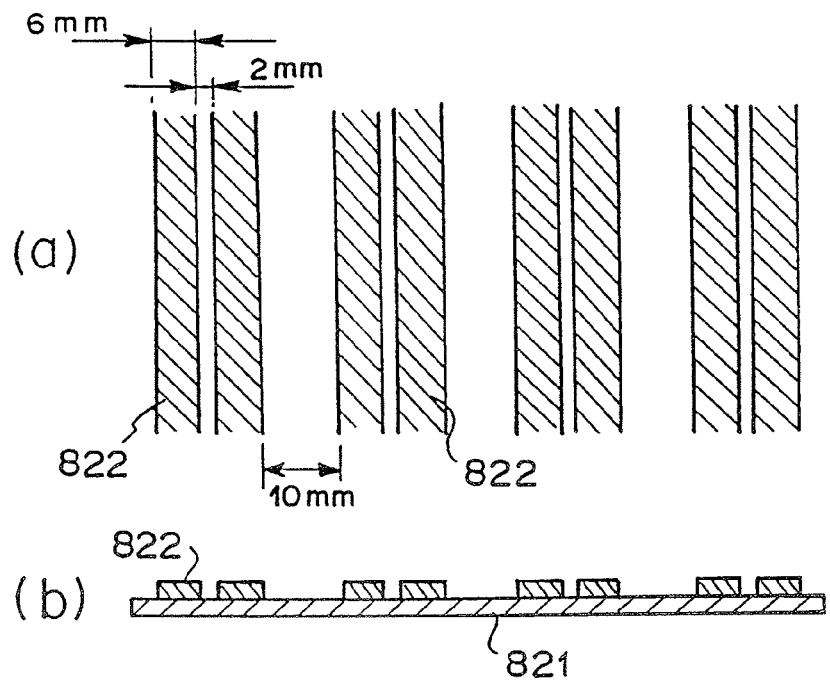
FIG. 82
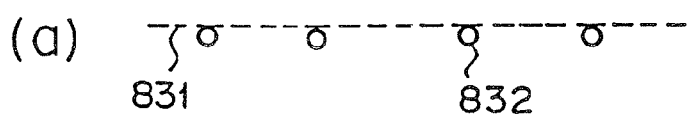
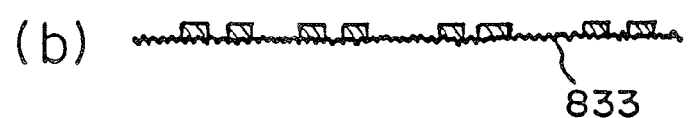
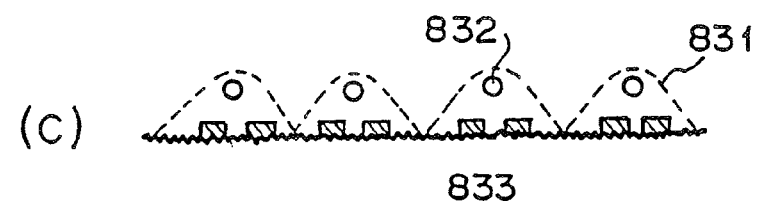
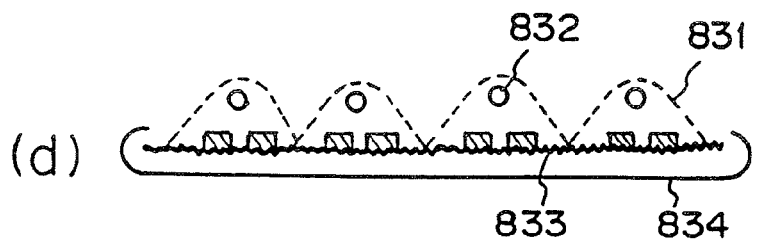

FIG. 83
(a)
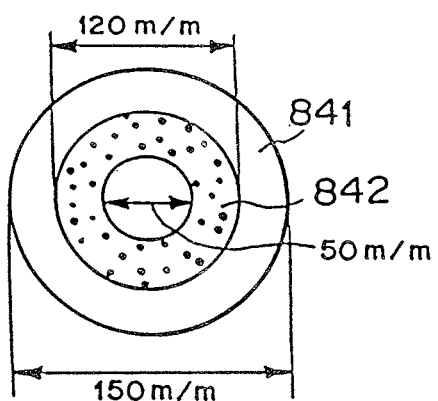
(b)
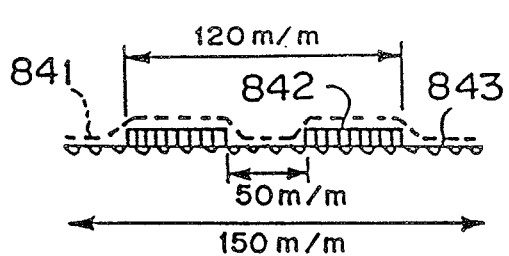
(c)
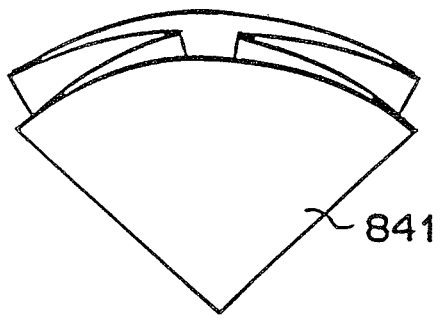
(d)
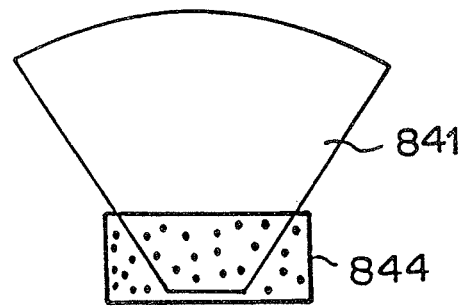

| PG/WATER RATIO | 70/30 | 50/50 | — | 30/70 | — | 10/90 | 2/98 |
|---|---|---|---|---|---|---|---|
| RESIDUAL PG | 100 | | 60 | | 30 | 10 | 0.5 |

HIGHLY ABSORBENT COMPOSITE AND METHOD OF MAKING THE SAME

This application is a division of U.S. patent application Ser. No. 09/242,482 filed Oct. 22, 1999 entitled "Highly Absorbent Composite Compositions, Absorbent Sheets Provided with the Compositions, and Process for Producing the Same" which is a 371 application of PCT/JP97/04606 filed Dec. 15, 1997 which claims priority of Japanese Patent Application Number 333520/1996 filed Dec. 13, 1996 and Japanese Patent Application Number 124623/1997 filed May 15, 1997 and Japanese Patent Application Number 192159/1997 filed Jul. 17, 1997 and Japanese Patent Application Number 213222/1997 filed Aug. 7, 1997 and Japanese Patent Application Number 313368/1997 filed Nov. 14, 1997 and Japanese Patent Application Number 329830/1997 filed Dec. 1, 1997, all the disclosures of which are herein incorporated by reference.

BACKGROUND OF THE INVENTION

1. Field of the Invention

The present invention relates to a new type absorbent composite wherein a water swellable solid body, particularly consisting of particles of various sin and shapes from powder to pellets is improved in functioning and handling characteristics. More particularly, the present invention relates to a highly absorbent composite composed of of containing an absorbent polymer as a water swellable solid body and having a shape entirely different from conventional absorbent materials and a capability of stably absorbing a liquid of much higher quantity than its own volume and to a highly absorbent composite mainly composed of the composite.

The highly absorbent composite of the present invention can widely be used in diapers for babies and adults, feminine hygiene products, products for handling liquid and solid wastes of animals, and medical blood absorbent products just like conventional highly absorbent products and thus is particularly useful as a super thin pulpless absorbent making the best use of the capabilities of a so-called absorbent polymer. In addition, the absorbent composite can be used for a cold insulator, water holding material, an anti-dewing material, covering material of submarine cables, material for preventing water related accidents.

In addition, the present invention relates to methods and apparatuses for making the absorbent composite and the composite mainly composed of the absorbent composite.

Moreover, the present invention relates to an absorbent sheet which provides also the leakage resistance of a conventional backsheet when the absorbent composite is used in absorbent products in combination with various sheet substrates, to an absorbent sheet which provides also the acquisition capability of a conventional topsheet when the absorbent composite is used in absorbent products in combination with various sheet substrates, and to an absorbent sheet which can be used alone providing also the capabilities of conventional backsheet and topsheet.

2. Prior Art

A main absorbent component used in a absorbent product, which absorbs water and liquid exudates, is composed of a combination of fluff type wood pulp and so-called super absorbent polymer (hereinafter referred to as the "SAP"). However, in recent years, in order to improve the distribution efficiency of absorbent products, to reduce the inventory and display space thereof, and to save natural resources, social needs for reducing the dimensions of otherwise relatively bulky absorbent products are becoming strong.

A means for making an absorbent product more compact and thinner, in a combination of SAP and pulp, would be to increase the content of SAP that has a higher absorbency than that of pulp by 2 to 10 times and accordingly decrease the content of pulp. Eventually, if the content of the SAP is made 100 percent, the thinnest and most compact absorbent product would be able to be obtained.

However, as the content of the SAP increases, when it absorbs water, so-called "gel blocking phenomenon" due to the characteristic of SAP occurs. Thus, the absorbent product does not work as designed. At the present time, it is said that the ratio of the contents of the SAP and pulp is at most 1 to 1. A structure in which the ratio of the contents of the the SAP to pulp is 2 or higher to 1, or so-called pulpless in which the content of the SAP is nearly 100 percent is very difficult to achieve at the present time. According to the conventional concepts generally applied in the field of absorbent products, the term "pulpless" means that the ratio of the contents of pulp to the SAP is approximately 1 or lower.

So far, various attempts for the pulpless structure have been made. A fiber type or web type SAP is made by directly spinning into acrylic acid type fiber or partially hydrolyzing acrylic acid type fiber. Another method is to make a web type absorbent polymer by impregnating a web with a monomer such as acrylic monomer and then polymerizing the monomer applying ultraviolet ray or electron beam. Still other method is to make an absorbent polymer sheet by carboxymethylating a non-woven fabric of cellulose or the like and then partially cross-linking the carboxymethyl cellulose.

However, so far, no successfully commercialized examples have been reported because of high costs of raw materials and high capital investments involved.

Liquid exudates discharged from living bodies are very different from each other depending upon their environmental and living conditions, and the frequency of discharging is not constant among them. Therefore, absorbent sheets used in many kinds of absorbent products need, responding to varied environs, to exhibit stably the capability of absorbing quickly and frequently.

As described above, a conventional two component (pulp and the SAP) absorbent is capable of meeting the need of frequently absorbing to some extent by taking advantage of the temporary retaining by pulp of liquids and the stably retaining by the SAP of liquids. However, an absorbent product in which the content of the SAP is made high or the SAP alone is used in order to secure high absorbency has a serious drawback; upon a liquid being discharged at first the SAP starts to absorb it all at once and thus an initial absorbing is very speedy but as the discharging is repeated, the absorbing speed drastically decreases.

SUMMARY OF THE INVENTION

A first embodiment of the present invention provides a highly absorbent composite comprising hydratable fine fibers in the form of microfibril obtained from cellulose or an derivative thereof, and water swellable solid particles, at least part of the surfaces of said water swellable solid particles being covered with said fine fibers in the form of microfibril.

Said hydratable fine fibers in the form of microfibril obtained from cellulose or an derivative thereof useful in the present invention will be hereinafter referred to as the "HFFM".

The absorbent composite can be formed in a three dimensional structure such as powder type, particle type, pellet type, sheet type, and any other type, and also in a sheet type with a supporting sheet of a non-woven fabric or the like as the base.

The present invention further provides a method of making the absorbent composite. The method comprises the steps of dispersing a water swellable solid body and the HFFM, in a dispersion medium comprising a mixture of an organic solvent and water, the organic solvent being capable of controlling the swelling of the water swellable solid body and dispersing the HFFM and thus being miscible with water, of separating the water swellable solid body and the HFFM from the resultant dispersion liquid from the dispersion medium, and of removing the liquid component and of drying them.

The absorbent composite of the present invention is basically a composite of a water swellable solid body and the HFFM covering the solid body. Examples of a water swellable solid body are various kinds of polysaccharides, flocculents, super water swellable absorbent polymer (the SAP) particles and the like. Among them, a drawback of the SAP, which is that the SAP is not easy to handle and store because of its high water absorbency, can be solved by covering it with the HFFM according to the present invention. In addition, in a structure in which the SAP particles are bonded together with the HFFM, the SAP particles are each held in position by the HFFM and an appropriate space surrounding each particle is secured. Thus, an extremely thin absorbent sheet is obtained.

A second embodiment of the present invention provides an absorbent sheet, wherein a supporting sheet and an absorbent layer provided on at least either surface of the supporting sheet are provided and wherein the absorbent layer has the HFFM, the SAP particles, and a short-cut staple fiber component having longer fiber length than the average particle diameter of the SAP particles and has an improved dimensional stability when wet swollen.

In the present invention, the short-cut staple fiber component having longer fiber length than the average diameter of the SAP particles connects the SAP particles with each other and at the same time provides a network structure which covers in network the top surface of a layer formed by the SAP particles and thus serves to prevent the SAP particles as wet swollen from going away.

The present invention further provides a method of making the absorbent sheet. The method comprises the steps of preparing a three-component dispersion slurry by adding and dispersing a short-cut staple fiber component and the SAP particles in a dispersion liquid wherein the HFFM is dispersed in a dispersion medium, of forming a layer of the slurry by spreading the three-component dispersion slurry onto a supporting sheet, of removing the dispersion medium from the slurry layer, and then of drying.

The absorbent sheet of this embodiment of the present invention consists of four components the SAP particles, the HFFM, a short-cut staple fiber component, and a substrate fabric supporting them. The SAP particles are a basic component giving a water absorbing capability. The SAP is available in various forms such as film and non-woven fabric besides the above described particles.

The HFFM prevents the SAP from settling as the dispersion stabilizer and also the SAP particles from coagulating with each other in making the absorbent sheet of the present invention and, after the absorbent sheet is made, play the role of a binder to bond the SAP particles together and the SAP with the substrate fabric. The short-cut staple fiber component takes the SAP particles into a network structure in cooperation with a supporting sheet by dividing the SAP particles covered with the HFFM and then covering the SAP particles in a network form.

A third embodiment of the present invention provides a composite absorbent sheet, wherein, in an absorbent sheet provided with a liquid pervious supporting sheet and an absorbent layer containing the SAP particles as bonded onto either surface of the liquid pervious supporting sheet, the absorbent layer forms a plurality of high absorbing regions having higher absorbing capability than otherwise as distributed onto the surface of the liquid pervious supporting sheet in a desired pattern.

In the composite absorbent sheet of the present invention, a liquid such as discharged liquid exudates, when it comes into contact with surface of the liquid pervious supporting sheet of an absorbent sheet, i.e., the surface where no absorbent layer exists, is first absorbed by the liquid pervious supporting sheet, penetrates inside the sheet by virtue of the liquid permeability, then diffuses, and contacts and is absorbed by an absorbent layer provided in contact with the opposite side of the surface where the liquid was discharged. The speed of absorption of the absorbent sheet as a whole is determined by the speed of absorption and diffusion into the liquid pervious supporting sheet and by the speed of the swelling and the absorption which occur in succession from the surface of the absorbent layer into its inside.

Therefore, if there is any difference in the thickness or density of the absorbent layer, as a liquid is discharged, the swelling and absorption progress first from thinner regions or regions of lower density. Also, if there is any difference in particle diameter of the SAP particles contained in the absorbent layer, the swelling and absorption progress first from regions of smaller diameters of particles. A basic concept of the present invention is that differences in absorbing capability caused by distributing regions of higher absorbency onto the surface of an absorbent sheet in a desired pattern are made to be reflected in differences in swelling and absorbing speeds.

In addition, by giving irregularly shaped circumference to the absorbent layer, the length of the circumference is made much longer than a straight or simply curved line of the circumference which would be if the irregular shape were not given, and therefore, a liquid once absorbed by the supporting sheet is absorbed rapidly by the absorbent layer having the long contact line so that the absorbing speed is thus further improved.

In order to distribute and form in a desired pattern the component forming the absorbent layer onto the supporting sheet, a method of making the component a slurry and applying and fixing the slurry onto the supporting sheet in a desired pattern meeting objectives is effective. The method needs to consist of a dispersing step where a slurry dispersion liquid containing the SAP particles is prepared, of a coating step where the dispersion liquid prepared in the dispersing step is applied onto the surface of the liquid pervious supporting sheet to form a plurality of regions of higher absorption distributed in a desired pattern and having higher absorbing capability than otherwise, and of a drying step where the absorbent layer formed in the coating step is dried.

In addition, the present invention provides an apparatus for working the methods. The apparatus comprises a plurality of nozzles for applying a dispersion slurry liquid containing the SAP particles in bands onto either surface of a liquid pervious supporting sheet running continuously and a supplying means for supplying the dispersion slurry liquid to the nozzles, and is characterized in that the supplying means has a mechanism of pulsating the flow of the dispersion liquid.

The present invention further provides an apparatus for making an absorbent sheet wherein a plurality of nozzles for applying a dispersion slurry liquid containing the SAP particles in bands onto either surface of a liquid pervious supporting sheet running continuously and a supplying means for supplying the dispersion slurry liquid to the nozzles are provided, and wherein the nozzles each have a plurality of discharging outlets.

The apparatus can be provided with a hot pressing means for pressing the liquid pervious supporting sheet as heated after a dispersion slurry liquid is applied.

A fourth embodiment of the present invention provides an absorbent tube, wherein the absorbent tube is composed of a supporting sheet consisting of a fiber web and the SAP particles or fibers supported by either surface of the supporting sheet, and wherein the supporting sheet is formed in a tube shape with the surface supporting the SAP facing inside.

The absorbent tube of the present invention has a novel three-dimensional structure, wherein a space for the SAP to swell is provided as the inherent structure of the absorbent by forming a tube of an absorbent sheet supporting the SAP.

In the absorbent tube of the present invention by virtue of the above described structure, an absolute quantity of the SAP existent in a unit area is approximately two times as much as that of an absorbent of a plane structure, and the absorbing capability of a unit area is also approximately two times as high as that of an absorbent of a plane structure. In addition, in the absorbent tube of the present invention, because the SAP is supported as attached onto the inner wall of a tube shaped supporting sheet, an adequate space for swelling is secured, and even if the SAP has swollen to its maximum absorbing capability absorbing a liquid, the absorbent as a whole still maintains its flexibility.

Various types of absorbent sheets have been spreaded so far. In order to make the function of an absorbent as used in an absorbent product exhibit to its maximum, the absorbent before it absorbs a liquid needs to be very thin like an underwear so that a sufficient space for swelling needs to be provided not to prevent the swelling of the absorbent. The present invention satisfies the need adequately, and provides an absorbent exhibiting an outstanding absorbing capability as assisted by the capability of a supporting sheet to diffuse a liquid.

The present invention further provides an absorbent product, wherein a absorbent tube consisting of a highly absorbent composite having a three-dimensional structure as described in the above is disposed in regions of desired absorptions as an absorbent core. The absorbent tube of the present invention is flat as not yet swollen and extremely thin like a crushed flat hollow tube, and when swollen absorbing water rises up as it as a whole swells with the cross-section area showing a nearby circular shape for the inside vacancy is filled with the SAP which increases in volume as swollen. In the absorbent product of the present invention, a single absorbent tube may be disposed in the absorbing region, but more preferably, a plurality of absorbent tubes are disposed in parallel. In the latter case, the structure is more stable and more flexible, and may more smoothly follow the body movement of the wearer of the absorbent product.

A fifth embodiment of the present invention provides an absorbent sheet, wherein a liquid impervious sheet material one of whose surfaces has many dents and absorbent material received and fixed in the dents are provided and thus leakage resistance and absorbing capability are imparted at the same time. In this embodiment of the present invention, the absorbent composite forms a structure where in the many dents provided on one of the surfaces of a liquid impervious sheet material, absorbent material containing absorbent polymer particles is filled. The composite absorbent has leakage resistance and absorbing capability at the same time satisfying the following requirements:

(1) A liquid impervious sheet material having dents on its surface, and, preferably, air permeability as well as water proofing is used.
(2) Absorbent material having such absorbing capability that is as high as possible is used.
(3) Absorbent material is filled and fixed in the dents.

The commonest form of material having a structure of dents as used in the present invention is flexible thermoplastic film such as polyethylene, polypropylene, and EVA of approximately 5 to 50 micron thickness on which many holes or recesses of given shapes are formed by mechanical punching, thermal forming, vacuum forming, or the like. Liquid impervious sheet material can also be used effectively and efficiently part of which has openings formed which are filled with absorbent material, to be described later, so that water proofing and leakage resistance are imparted.

Absorbent material to fill the dents needs to be of fine sizes to fill a relatively small space, and at the same time to have a high absorbing capability per a unit volume to secure a required absorbency with the quantity of the material to fill the small space.

The liquid impervious sheet material is, for example, thermoplastic film of 5 to 50 micron thickness, or a conjugate of 5 to 50 thick thermoplastic film and non-woven fabric. The dents formed on the sheet material may have the same liquid imperviousness as otherwise, or, an alternative configuration is that, in the bottoms of all or part of the dents, opening or porous portions which, as they are, liquid may pass through may exist and are stopped up with the absorbent material. The absorbent sheet of this configuration is liquid impervious as a whole, and at the same time, with the absorbent material received ad fixed in the recesses, exhibits a high liquid absorbing capability so that it combines the two functions of a liquid impervious sheet and an absorbent.

As a method of filling and fixing the dents provided on a liquid impervious sheet material with the SAP or absorbent material containing the SAP, a method generally applied in making absorbents for use in diapers and sanitary napkins can be applied as it is. One preferable method comprises the steps of dispersing, for example, the SAP and the HFFM in air current, of filling the dispersed materials into the dents, and of fixing the filled dents by means of hot melt.

If each and every dent on a liquid impervious sheet material is provided with an opening or liquid pervious structure, by supplying the liquid impervious sheet material onto a conveyor with a vacuum provided and supplying the slurry from above the liquid impervious sheet material continuously, the liquid contained in the slurry passes the sheet material through the opening or liquid pervious structure to be separated, leaving only the solid component in the slurry in the dents. Further, by removing the liquid component and drying, the SAP particles or the SAP particles and the sheet material are bonded by the HFFM with each other, and fixed in the positions that they are situated, so that water proofing is imparted, too. By selecting an appropriate ratio between the quantity of the SAP and the quantity of the HFFM as well as the properties of the HFFM, preferable properties can be imparted as material for an absorbent: while desired leakage resistance and some air permeability are obtained at the same time.

The SAP which is used for these purposes should be particles, preferably, fine particles, so that it may be held stably in a small space, and specifically, the diameter of the particles should be 0.4 mm or less, or, more preferably, 0.3 mm to 0.1 mm. Very fine particles, such as those of 0.1 mm diameter, can be coexistent with coarser particles, such as those of 0.4 mm or coarser. In case fiber material such as wood pulp is made to coexist with the SAP, the more the content of the SAP, the better the result: the content of the SAP is preferably 50 percent or higher.

As discussed in the above, in making the composite absorbent of the present invention, the HFFM, the SAP and, as required, a short-cut staple fiber component are dispersed in a dispersion medium. A particularly effective dispersion medium is a polyvalent alcohol, which has the tendency to be highly viscous at a low temperature and logarithmically to reduce in viscosity as heated. Specifically, by utilizing the behavior in the relation between temperature and viscosity of a mixed system of a polyvalent alcohol and water, the transferring and forming are carried out while the system is stably maintained which is made at a low temperature and highly viscous at the time of dispersion and storing, and the forming and removal of the liquid component are made easier while the system is heated and hydrated at the time of removing the liquid component so that the viscosity is decreased and the liquidity is increased.

DETAILED DESCRIPTION OF THE INVENTION

Hereunder, the elements constituting each structure of the highly absorbent composite and the absorbent sheet provided with the absorbent composite of the present invention will be described.

In a first aspect of the present invention, the absorbent composite is composed of the SAP and the HFFM.

In a second aspect of the present invention, the absorbent composite is composed of the SAP, the HFFM, and a short-cut staple fiber component, which is larger than the SAP.

In a third aspect of the present invention, either of the absorbent composites of the first and the second aspects forms an absorbent sheet combined with a supporting sheet.

If components are extracted from these absorbent composites and these absorbent sheets to be made by combining the absorbent composites, the following four components will come out.

First of all, each component will be described:

(1) SAP Particles

Absorbent polymer particles, herein called the "SAP", are generally carboxy methyl cellulose, polyacrylic acid and polyacrylates, cross-linked acrylate polymers, starch-acrylic acid grafted copolymers, hydrolysates of starch-acrylonitrile grafted copolymers, cross-linked polyoxyethylene, cross-linked carboxymethyl cellulose, partially cross-linked water swellable polymers such as polyethylene oxide and polyacrylamide, isobutylenemaleic acid copolymer, etc. Base polymer particles are obtained by drying any of these polymers. Then, after treatment is applied to increase the cross-linking density of the surface of the particles, and at the same time, a blocking inhibitor is added to control the blocking of product particles due to absorbing moisture.

Also, an amino acid cross-linked polyaspartic acid which is biodegradable or a microorganism based highly absorbent polymer which is a cultured product of Alcaligenes Latus is added, too.

SAP products are available on the market in such forms as particles, granules, films, and non-woven fabrics. The SAP product in any of such forms can be used in the present invention. A preferable SAP product for the present invention is in such forms as particles, granules, pellets, flakes, short needless and the like which can be uniformly dispersed in a dispersion medium. In this specification of the present invention, the term "particle(s)" is used to generally mean any of these forms.

(2) HFFM

In the present invention, a micro-network structure holding the SAP particles in position is fixed with the HFFM. The structure prevents the SAP particles from coagulating with each other, and stabilizes and makes uniform dispersion condition in making the composite absorbent of the present invention, and serves as a binder for binding the SAP particles with each other and the SAP with a supporting sheet after drying is carried out.

The HFFM is, in general, extremely fine fibrous material of 2.0 to 0.01 microns in average diameter, and of 0.1 microns or finer on average, and sufficiently water resistant to prevent the structure from collapsing immediately after or when the SAP absorbs water and so swells, and besides, has such properties as do not hinder the permeability of water and the swelling of the SAP. What is specially noteworthy here is that the HFFM has an extremely strong hydratable property of binding with water. By virtue of the strong hydratable property, the HFFM hydrates when dispersed in a medium containing water to show a high viscosity which serves to maintain a stable dispersion condition.

A characteristic of the hydrating property of microfibril is a high amount of retained water. For example, the desired hydrating property of microfibril after their dispersion is centrifuged at 2,000 G for 10 minutes as calculated by the following formula should be 10 ml/g or higher, and preferably 20 ml/g or higher:

$$\text{Amount of water retained (ml/g)} = \text{Precipitated volume (ml)/Microfibrils (g)}$$

In this specification of the present invention, the term "HFFM" is used to mean generally strongly hydratable fibrous materials in the form of microfibril. In some cases, the HFFM of 2.0 microns or larger in average diameter can be used, and may be a mixture of so-called fibrils and the HFFM.

The HFFM can be obtained by microfibrillating cellulose or a cellulose derivative. For example, the HFFM is obtained by grinding and sufficiently beating wood pulp. The HFFM is called "microfibrillated cellulose (MFC)", and if further fibrillated, is called "super microfibrillated cellulose (S-MFC)".

Also, the HFFM can be obtained by grinding and sufficiently beating finely cut fiber of man-made cellulosic fiber such as Polynosic modified rayon staple fiber, Bemberg cuprammonium rayon yarn, and solvent spun LYOCELL rayon fiber.

Alternatively, the HFFM can also be obtained by metabolizing microorganism. In general, acetic acid bacteria such as Acetobactor Xylinum is cultivated, while stirred, in a nutrient containing an appropriate carbon source so as to generate crude HFFM, which is in turn refined to obtain the HFFM. Such HFFM is called "bacteria cellulose (BC)".

Also, so-called fibril type material which is obtained by coagulating under a shear force a copper ammonium solution of cellulose, an amine oxide solution of cellulose, an aqueous solution of cellulose xanthate, or an acetone solution of cellulose, all of which can be spun into fibers, is refined to obtain microfibril-type material, which material can also be used for the present invention. The details of the HFFM are described in Japanese Patent Examined Publication Nos. SHO 48-6641 and SHO 50-38720.

Such HFFM is commercially available under trademarks "CELLCREAM" (made by Asahi Chemical Industry Co. Ltd.), "CELLISH" (made by Daicel Chemical Industries, Ltd.), and so forth.

MFC, S-MFC, and BC are particularly preferable for the present invention. The technical details of the S-MFC are described in Japanese Patent Publication No. HEI 8-284090, and of the BC in Japanese Patent Examined Publication No. HEI 5-80484.

How to use the MFC and the S-MFC, (both being hereinafter referred to as the "MFC") is explained in detail below. The MFC which is concentrated to approximately 30 percent of solid content is available on the market. To use such concentrated MFC, an additional procedure of diluting and refining such MFC is required, which requires an additional time, and the concentrating needs an additional cost. For the present invention, the MFC whose concentrated solid content is 10 percent or lower is preferable. However, if the MFC is diluted to 2 percent or lower, the water content will become too high, and the selection of the contents of the MFC in an organic solvent/water mixture system will be too narrow. In case the MFC in a diluted system like this is used, it is recommended that a organic solvent/water system in which an organic solvent to be used in a dispersion medium is used rather than a simple water system in microfibrillating raw material pulp. Hence, a dispersion liquid of the MFC which is diluted to around 2 percent can also be used for the present invention.

How to use the BC is also described in detail below. The BC is obtained as a metabolized product of microorganism. Depending on the methods of cultivating and harvesting, the concentrations and the forms of the BC will be different. In order to obtain as uniform concentrations and forms as possible, a refining treatment is recommended. Macerating harvested and refined BC which is diluted to 2 percent or lower by means of a mixer or a defibrator will make finer and more uniform HFFM in coagulated condition, and its viscosity will be much increased and its capacity of binding the SAP will also be improved. For the present invention, therefore, the use of the BC which is refined is recommended.

(3) Short-Cut Staple Fiber Component

The preferable denier of short-cut staple fibers constituting a short-cut staple fiber component is 10 or more times as coarse as that of the MFC. The average denier is preferably approximately 0.01 denier or corner and approximately 3.0 denier or finer.

In the present invention, the length of short-cut staple fibers constituting a short-cut staple fiber component is an important element. The short-cut staple fibers which are to divide in sections the SAP particles covered by the MFC and to cover the particles in a network structure need to have longer fiber length than the average diameter of the SAP particles. In general, the average particle diameter of the SAP available on the market is approximately 0.1 mm to 0.6 mm.

The SAP which is made by dispersion polymerization has relatively small particle diameter. If such SAP is used, short-cut staple fibers which are relatively short can adequately be used. On the hand, if the SAP in pelletized or flake form is used, short-cut staple fibers which are relatively long should preferably be used.

These short-cut staple fibers play the role of covering swollen SAP. If the short-cut staple fibers swell or dissolve in the same way as the SAP, they will not be effective. The short-cut staple fibers, therefore, need to have a property that they will not swell or dissolve in water.

The short-cut staple fibers which can be effectively used for the present invention are grouped into the following two kinds:

(i) Pulp State Fibers

Typical pulp fibers are wood pulp obtained by digester reclaiming needle- or broad-leaved trees, linter pulp obtained with cotton linter as raw material, or the like. Other pulp state fibers are obtained by shear coagulation, flush spinning, or spray spinning of polymer solutions to make solidified fibers: acetate (ACe) fibril, polyacrylonitrile (PAN) fibril, polyethylene (PE) based synthetic fiber pulp, polypropylene (PP) based synthetic fiber pulp or the like are available. In addition, in case fine SAP is used, pulp state fiber obtained from strained lees of beet or coffee beans can also be used as the short-cut fibers.

PP and PE based synthetic fiber pulps are easy to thermally melt, and as such preferably used to make more stable structure by thermal treatment.

(ii) Short Cut Synthetic Fibers

Of cellulosic fibers such as rayon, Polynosic modified rayon, and LYOCELL, short-cut staple fibers and their fibrillated materials of 10 mm or shorter in fiber length made for making paper.

Short-cut staple fibers such as PET, PP, PVA, and PAN, and short-cut staple fibers of bicomponent fibers such as low melting point polyester/PET, PP/PE, and PE/PET.

Short-cut fibers of very fine fibers obtained by blending of different polymers, or by spinning is land-like fibers.

Particularly, bicomponent fibers such as PE/PET, PE/PP, and low melting point polyester/PET are preferable to aim at stabilizing the SAP by heat treatment through utilizing the effects of the component in the composite fibers that is easy to thermally dissolve. Also, those of such fibers on which an antibacterial agent or a deodorant is applied are preferable.

(4) Supporting Sheet

A supporting sheet functions as follows: through binding the SAP particles covered and bonded by the MFC to a supporting sheet, the strength and dimensional stability are improved, and the liquid to be absorbed through the supporting sheet is diffused and distributed, and the SAP particles are stopped up in the dents, raised fibers, entangled fibers, or vacancies which are likely to exist on the supporting sheet so that the stability is achieved.

The supporting sheets which can be used for the present invention are described in detail here: In the present invention porous sheets such as dry laid fluff pulp mat and its bonded sheet, wet formed pulp mat, carded dry laid non-woven fabric, spun lace, spun bond, melt-blown non-woven fabric, and non-woven fabric made of opened tow of acetate or polyester fibers can be used. A supporting sheet is preferably of a bulky structure to hold and stabilize the SAP particles in its spaces. As for the bulkiness of the supporting sheet, an apparent density as calculated from a thickness measured using a thickness gauge (as described later) and a weight should be 0.2 g/cm$^3$ or less, and preferably 0.1 g/cm$^3$ or less.

To obtain such bulky non-woven fabric, the following means are taken:

<Web Comprising a Combination of Finer Denier Fibers and Coarser Denier Fibers>

While coarser denier fibers are high in resilience and compression resistance, but a web of such coarser fibers is not high in bonding strength, finer fibers give the opposite tendency. Therefore, it is preferable to combine both types of fibers. Such combination is obtained by blending coarser denier fibers and finer denier fibers or laying a layer of coarser denier fibers on top of a layer of finer denier fibers. To achieve an object of the present invention, a two-layer structure, particularly, a non-woven fabric comprising a combination of a layer of hydrophilic fibers which are relatively high in density and of finer denier and a layer of hydrophobic fibers which are relatively low in density and of coarser denier, is preferable.

<Non-Woven Fabric Given Bulkiness>

In addition to combining fibers of different deniers, shrinkable fibers can be combined. By shrinking such shrinkable fibers, an uneven surface having dents or a corrugated surface having furrows is made, which is a method of making a bulky supporting sheet as is suitable for the present invention.

<Bulky Supporting Sheet Whose Surface is Treated>

By flocking a non-woven fabric of a smooth surface or raising a relatively thick non-woven fabric mechanically, a bulky supporting sheet suitable for the present invention can be made.

The composite absorbent sheet of the present invention comprising the above-described four components is required to have the following structure in order to fully exhibit the functions as are expected of an absorbent sheet: the sheet needs to have a stable structure so that when it is dry it can be folded, sated and stretched to extend, and formed to be corrugated, and when it is worn to absorb body exudates, it needs to have outstanding absorbing and diffusing capabilities, and after it is used, no SAP particles should exfoliate or come off.

Even if the absorbing rate is high, the sheet should not have such structure which may collapse. On the other hand, even if the SAP particles are stably fixed, if the sheet takes a long time to absorb and swell, it will not be suitable for the present invention. Hence, an important requirement of the present invention is how best the above-described four components are combined in a rational way.

(5) Combinations of the Four Components

Next, various combinations of the four components and their advantages are described in detail below:

(a) Combination of Supporting Sheet and Short-Cut Staple Fibers

Whether a supporting sheet is hydrophilic or hydrophobic determines desirable properties of short-cut staple fibers to be used in combination with the supporting sheet. That is to say, in case the supporting sheet is of hydrophobic fibers such as PP and PET, short-cut staple fibers to be combined with the supporting sheet are preferably cellulosic fibers such as wood pulp and fibrillated Lyocell. By using such fibers, the absorbency and diffusion will be much improved. On the other hand, in case hydrophilic fibers such as rayon are used, they should be combined with PE synthetic pulp, or short cut PE/PET bicomponent fibers, which will maintain a preferable balance between the absorbency and diffusion and the retention of form.

(b) Combination of Supporting Sheet and Heat Meltable Short-Cut Staple Fibers

To obtain a good wet stability of a absorbent sheet, heat setting a combination of a supporting sheet of a specified structure with short-cut staple fibers is preferable, which makes it possible to obtain a strong structure.

For example, if a carded web of 15 g/m$^2$ consisting of 1.5 denier rayon fiber and a carded web of 15 g/m$^2$ consisting of 6 denier PET fiber are water-jet entangled, then a web of a two layer structure having a strongly hydrophilic bottom layer and a bulky top layer is obtained. On the other hand, by dispersing a short-cut staple fiber (a bicomponent fiber of PET/low melting point polyester which is easy to heat melt, of 1.2 denier and 2 mm fiber length) in the MFC/SAP slurry, a co-dispersed slurry is obtained, and by spreading this co-dispersed slurry onto the PET layer of the two layer web, a solid layer is obtained. Next, by drying and then heat setting this solid layer, a network structure where PET of the supporting sheet and easy to heat melt polyester, of the short-cut staple fiber component are thermally fused is formed, in which network structure the SAP particles are contained in closed spaces.

In a structure like this, when liquid is absorbed, the liquid is rapidly supplied from the hydrophilic supporting sheet layer to the SAP particles to start swelling, and even after sufficiently swollen, the SAP will hardly come off the supporting sheet. The kinds of fibers forming the bulky layer of the non-woven fabric of a two layer structure and the combinations with the short-cut staple fibers suitable to such bulky layer fibers are shown below:

| Bulky fiber component of a supporting sheet of a two layer structure | Short-cut staple fiber component to be added as slurry |
| --- | --- |
| Coarser denier PE/PET | PE synthetic pulp, finer denier PE/PET |
| Coarser denier PE/PET | PE synthetic pulp, finer denier PE/PET |
| Coarser denier PET | Finer denier PET/easy-to-melt polyester |
| Coarser denier Rayon | Easily-soluble-in-hot-water PVA fibers |

(c) Blending Ratio of MFC and Short-Cut Staple Fibers

In general, short-cut staple fibers are added to a slurry of the MFC to provide a two-component dispersion liquid, and, the SAP particles are added further to provide a three-component slurry. The three component slurry is spreaded onto a supporting sheet. In the three-component slurry, if the ratio of short-cut staple fibers to the MFC in quantity is too high, the MFC will be used only to cover and bond the short-cut staple fibers and decease the bonding efficiency of the SAP, and the stability of the slurry becomes lower. On the other hand, if the quantity of short-cut staple fibers is too small, the desired network function will not be obtained. The ratio of the MFC (P) and short-cut staple fibers (Q) ranges between $P/Q=1/5$-$5/1$, and preferably $P/Q=1/3$-$3/1$.

In the present invention, as described in the above, the three components, the SAP, the HFFM, and a short-cut staple fiber component as required, are dispersed in a dispersion medium. The dispersion medium is described below:

To handle the SAP particles and the HFFM, and as required, a short-cut staple fiber component as a stable slurry-like dispersion liquid, it is important to select an appropriate dispersion medium. If the SAP is slurry-like already from the beginning of its making process, for instance, in a system such as a dispersion polymerization of acrylic acid where polymerization reaction is run in a cyclohexane/water system, by cross-linking in dispersion (if necessary) after polymerization reaction is finished and then adding to the slurry a water dispersion liquid of the HFFM or a solvent/water dispersion liquid while the liquid is stirred, a stable slurry containing partially swollen SAP and the HFFM can be obtained.

To obtain a stable dispersed slurry using dry SAP available on the market and the HFFM, and as required, the short-cut staple fiber component, it is preferable to disperse them in a mixture medium of water and a organic solvent.

If the SAP particles, the HFFM, and as required, the short-cut staple fiber component are dispersed in a dispersion medium like this consisting of an organic solvent and water, a dispersion liquid where the HFFM and the SAP particles are uniformly and stably dispersed is obtained owing to the viscosity generated by the combination of the HFFM and the dispersion medium.

As organic solvents used for the present invention, alcohols such as methanol, ethanol, and isopropyl alcohol, polyvalent alcohols such as ethylene glycol, diethylene glycol, propylene glycol, low molecular weight polyethylene glycol, and glycerin, and representative water soluble organic solvents such as acetone, methyl ethyl ketone, dioxane, and dimethyl sulfoxide are available. In using low boiling point alcohols, an apparatus may need to be of an explosion proof construction because of their high volatility and flammability. On the other hand, ethanol and propylene glycol are preferable because of their safety to the environment and to the skin of a wearer and low possibility of remaining in a product. To any of these solvents, a water insoluble solvent such as cyclohexane may be added in a quantity that does not interfere with dispersion.

As a dispersion medium used to maintain a condition where the HFFM, the SAP particles, and as required, the short-cut staple fiber component are uniformly dispersed, without being coagulated and settling, for a relatively long period of time, solvents of a group of polyvalent alcohols are particularly preferable. Solvents of a group of polyvalent alcohols are water soluble, and do not ice even below 0° C. or lower as are mixed with water showing a highly viscous condition, and thus can be stably stored for some time. As the temperature goes up, the viscosity will decrease, which makes easier the transfer by means of a pump and forming of the composite sheet.

Examples of polyvalent alcohol solvents are ethylene glycol, propylene glycol, diethylene glycol, triethylene glycol, low molecular weight polyethylene glycol, and glycerin. The viscosity of the polyvalent alcohol solvents will vary with the temperature very much. For example, as shown in Table 1 below, the viscosity greatly changes for the difference of 30° C. between 20° C. to 50° C.

TABLE 1

| Solvents | Viscosity (cp) | |
|---|---|---|
| | 20° C. | 50° C. |
| Ethylene glycol | 22.0 | 7.3 |
| Propylene glycol | 56.0 | 8.6 |
| Diethylene glycol | 30.0 | 11.5 |
| Triethylene glycol | 49.0 | 14.0 |
| Glycerine | 1412.0 | 142.0 |

A manufacturing process can be efficiently designed through incorporating this change in viscosity successfully in the process. However, a drawback of polyvalent alcohol solvents is that, because they show a high viscosity even when they contain water, they may cause uneven coating in coating a substrate sheet material because they do not fit well with the substrate material due to their hardly penetrating the material. In such case, adding of methanol or ethanol to combine with this polyvalent alcohol solvent, for example, applying of a three-component system, PG/ethanol/ water, may be effective.

The slurry obtained in the way described in the above which consists of the SAP particles, the HFFM, and as required, a short-cut staple fiber component forms an absorbent layer as applied on the surface of a liquid pervious supporting sheet. In general, the slurry is applied onto the whole surface of the absorbent sheet uniformly and evenly, but depending upon the uses, can be applied in an appropriate pattern.

In the event that the absorbent layer is formed in a pattern, a liquid pervious supporting sheet is a substrate supporting the absorbent layer and concurrently, plays the role of solid-liquid separating from the slurry in the manufacturing process. It is, therefore, preferable that the components of a supporting sheet have affinity to an absorbent layer and that at the same time the supporting sheet is of a structure having fine openings through which solid does not permeate, but liquid does permeate. For this purpose, a non-woven fabric made of natural fiber, chemical fiber and synthetic fiber provides a preferable supporting sheet. Especially, in case the HFFM of cellulose fiber is used as a bonding agent, cellulose fiber which has a bonding to hydrogen is preferably combined to make a supporting sheet.

In the present invention, an absorbent layer is formed by applying the above-described slurry onto the surface of a liquid pervious supporting sheet, and it is required that as a result of such application of the slurry a plurality of highly absorbing regions having higher absorbing capability distributed in a desired pattern need to be formed.

A representative means of forming an absorbent layer as non-uniformly distributed is to form a distribution in a pattern by pulsating in some appropriate way the discharging quantity or width of a slurry dispersion liquid or to form the absorbent layer yet to be solidified after the slurry is applied.

Means for pulsating the dispersion liquid as discharged is to use a plunger pump or a tube pump which discharges the liquid with pulsation. When a pump which does not pulsate the quantity of discharge is used, a device of giving pulsation needs to be installed at the side of discharging.

BRIEF DESCRIPTION OF THE DRAWINGS

FIG. 7 is a sectional view of an absorbent composite embodying the present invention; FIG. 7(a) shows an absorbent composite in particles, and FIG. 7(b) shows an absorbent composite in flake;

FIG. 8 shows a sheet material consisting of an absorbent composite embodying the present invention; FIG. 8(a) is a schematic sectional view and FIG. 8(b) is a sketch of a microphotograph thereof;

FIG. 9 shows another sheet material consisting of an absorbent composite embodying the present invention; FIG. 9(a) is a schematic longitudinal section and FIG. 9(b) is a sketch of a microphotograph thereof;

FIG. 10 is a schematic longitudinal sectional view of a composite sheet material embodying the present invention;

FIGS. 19(A), (B), (C) and (D) are longitudinal sectional views of different forms of an absorbent tube embodying the present invention;

FIG. 66 is a perspective view schematically showing an example of an apparatus for making an absorbent sheet of the present invention;

FIG. 67 shows an example of a nozzle for discharging a slurry dispersion liquid to be applied in the apparatus of FIG. 66: (A) is a side view thereof and (B) is a bottom view thereof;

FIG. 81 shows other example of a composite absorbent of the present invention: (a) is a plan view thereof and (b) is a sectional view thereof;

FIGS. 82 (A) and (D) are explanatory drawings showing a process of making still other form of a composite absorbent of the present invention;

FIG. 83 shows an incontinent pad for a woman in which a composite absorbent of the present invention is applied: (a) is a plan view thereof,(b) is a sectional view of the composite absorbent, (c) is a perspective view showing the condition where the composite absorbent of (a) is folded, (d) is a side view of a finished incontinent pad for a woman;

DETAILED DESCRIPTION OF THE PREFERRED EMBODIMENTS

The present invention will be described in detail with reference to the accompanying drawings.

Figure 1:
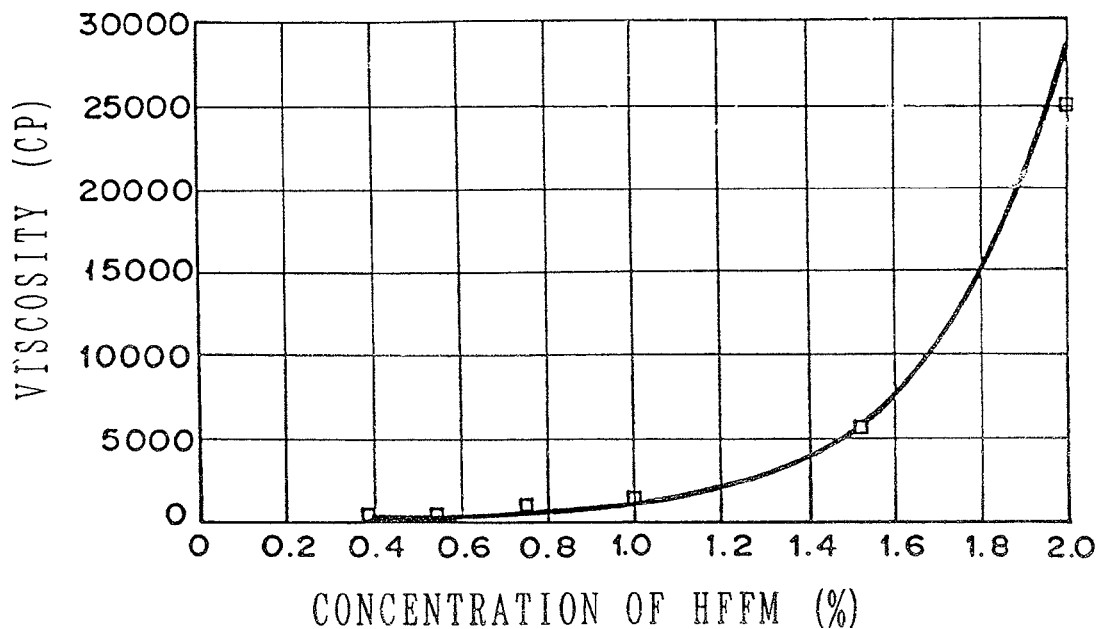
FIG. 1 is a graph showing the relationship between the concentration and the viscosity of the HFFM in a solvent.

FIG. 1 is an example showing the concentration and viscosity of super microfibrillated cellulose in the form of microfibril (hereinafter sometimes referred to as the "S-MFC") in a dispersion liquid. It will be understood from FIG. 1 that even at low concentration a high viscosity is still maintained. The dispersion liquid of the HFFM exhibits a structural viscosity, and a fluidized orientation is exhibited and the viscosity is reduced when a shear force is applied. However, as the shear force is reduced, the viscosity is restored. Thus, if the SAP particles are added and dispersed in the dispersion medium of the HFFM, in a low sheared dispersion state, the SAP particles are stably taken in a network structure of the HFFM, and consequently, the SAP of a high concentration can stably be dispersed. The dispersion is transferred with ease by means of a pump or the like, because then the viscosity is deceased.

Therefore, when the SAP is dispersed in a dispersion medium of the HFFM, the SAP of a high concentration can be stably dispersed. In the process where the dispersion medium is removed, the HFFM are in a plaster state to form a network structure as they are firmly self-bonded and contain and mechanically enclose the SAP particles, and as the HFFM is bonded with each other in the effect of hydrogen bons, hold securely the SAP particles.

Figure 2:
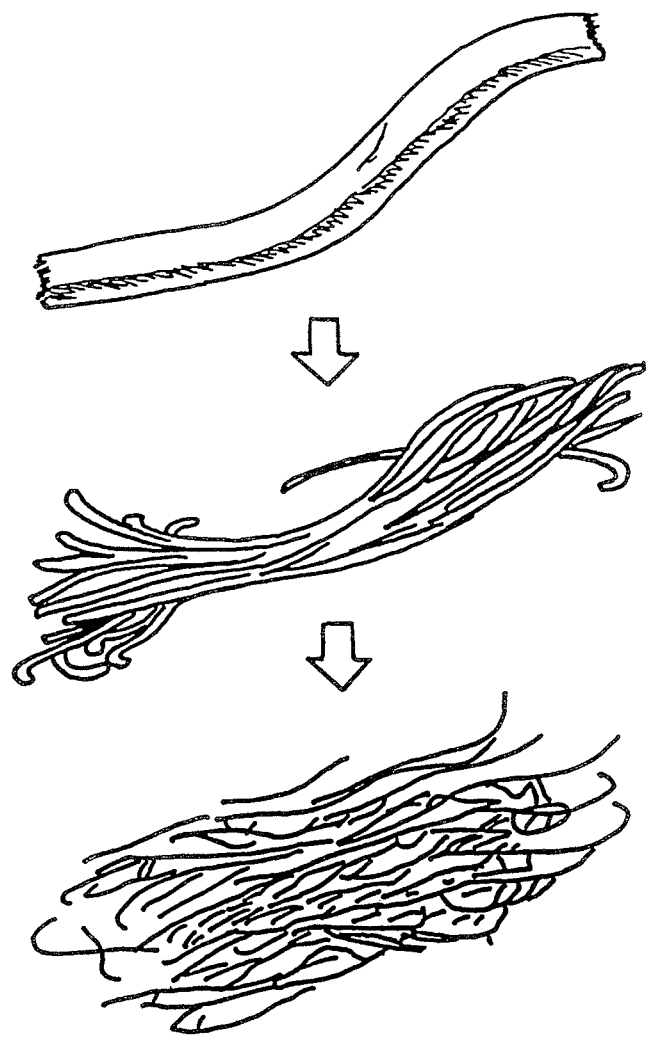
FIG. 2 is an explanatory diagram showing a process of obtaining the HFFM from cellulose.

Fine fibers in the form of microfibril (the "HFFM") can be obtained by microfibrillating cellulose or its derivative. For example, by grinding and sufficiently beating wood pulp, the HFFM is obtained in a process as shown in FIG. 2. The HFFM is sometimes referred to as the "MFC" (microfibrillated cellulose) and if further fibrillated, as the "S-MFC" (super microfibrillated cellulose).

Next, a method of making a highly absorbent composite composed of the above-described HFFM and the SAP is described below:

According to the present invention, in making the above-described highly absorbent composite, the dispersion behavior of the SAP in a dispersion medium of the HFFM and the behavior of the HFFM after removing the liquid component are ingeniously utilized. In other words, the highly absorbent composite of the present invention can be obtained by dispersing the SAP particles and the HFFM in a dispersion medium that is a mixture of an organic solvent miscible with water and water where the HFFM is stably hydrated and dispersed, by separating the SAP particles and the HFFM from the resultant dispersion liquid, and by removing the liquid component, followed by drying. As a result of this procedure, a typical pulpless highly absorbent composite where the content of the SAP is 90 percent or higher can be obtained.

To prepare a dispersion liquid of the HFFM, a dispersion liquid where the HFFM is dispersed in water is first prepared as a stock liquid. As the concentration of the stock liquid becomes higher, an apparatus preparing the HFFM dispersion becomes more compact. On the other hand, however, the viscosity of the stock liquid increases at higher concentrations, which makes the handling of the stock liquid more difficult. Therefore, a water dispersion liquid with a concentration of 10 percent or lower, preferably 5 to 1 percent, is used. The stock liquid is added to a dispersion medium consisting of an organic solvent and water to obtain a dispersion liquid of the HFFM having a prescribed concentration of the HFFM and a viscosity accompanied by the concentration. As a means of adding and mixing the SAP to the dispersion liquid, a means of dispersing the SAP particles into the above-described dispersion liquid is generally applied.

By dispersing the HFFM and the SAP in this dispersion liquid of an organic solvent and water, a network structure of the HFFM is formed and the SAP particles are incorporated in the network structure so that a stable dispersion state is secured. When the dispersion medium is removed later, the physical entwined structure of the HFFM and the stable hydrogen bonding of the HFFM with each other are formed, and as a result, it is assumed that a three dimensional structure is formed.

The mixture ratio of an organic solvent and water is established in a range enabling the formation of a network structure of the HFFM and suppressing as much as possible the absorption of water by the SAP.

Figure 3:
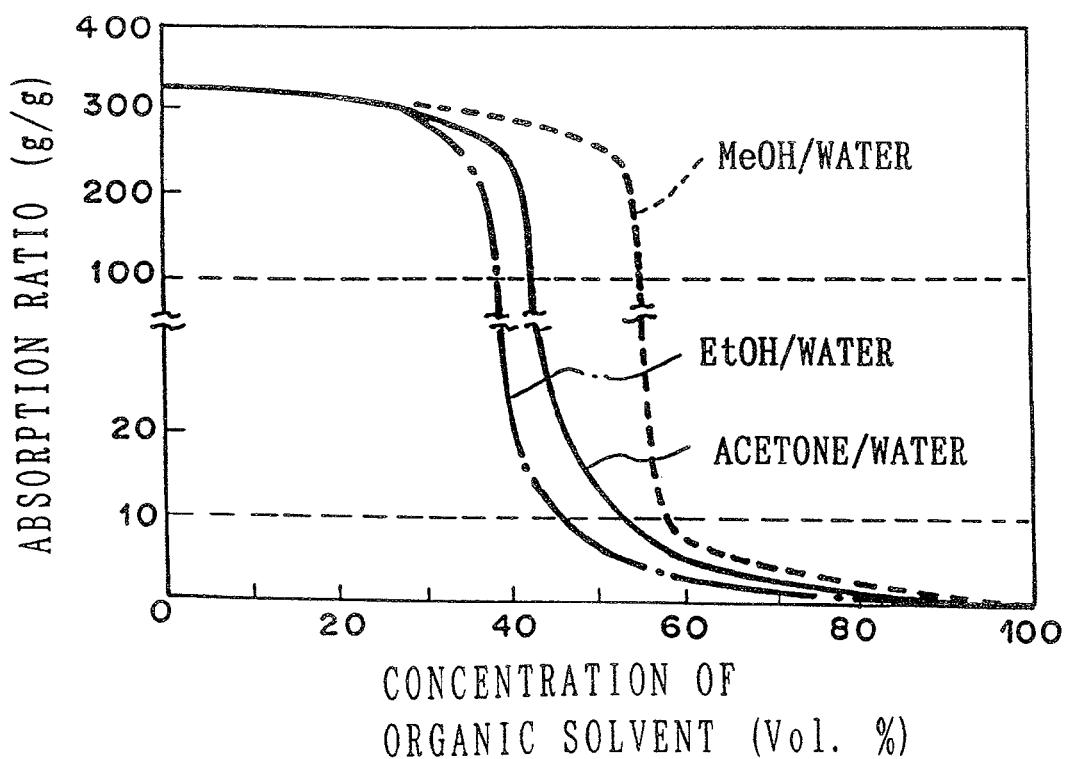
FIG. 3 is a graph showing the concentration of an organic solvent and the swelling rate of the SAP in a dispersion medium.

Of the above-described organic solvents, representative solvents are described here. In the graph of FIG. 3 is shown the relationship between the concentration of an organic solvent and the water absorbing ratio of the SAP in the case that as such organic solvent methyl alcohol, ethyl alcohol, and acetone are used. It is shown in FIG. 3 that in case ethyl alcohol or acetone is used, when the concentration of the solvent is 50 percent or lower, the water absorbing ratio of the SAP sharply increases, and that, in case methyl alcohol is used, when the concentration is 60 percent or lower, the water absorbing ratio of the SAP sharply increases. It is, therefore, preferable to have a higher concentration of an organic solvent.

Figure 4:
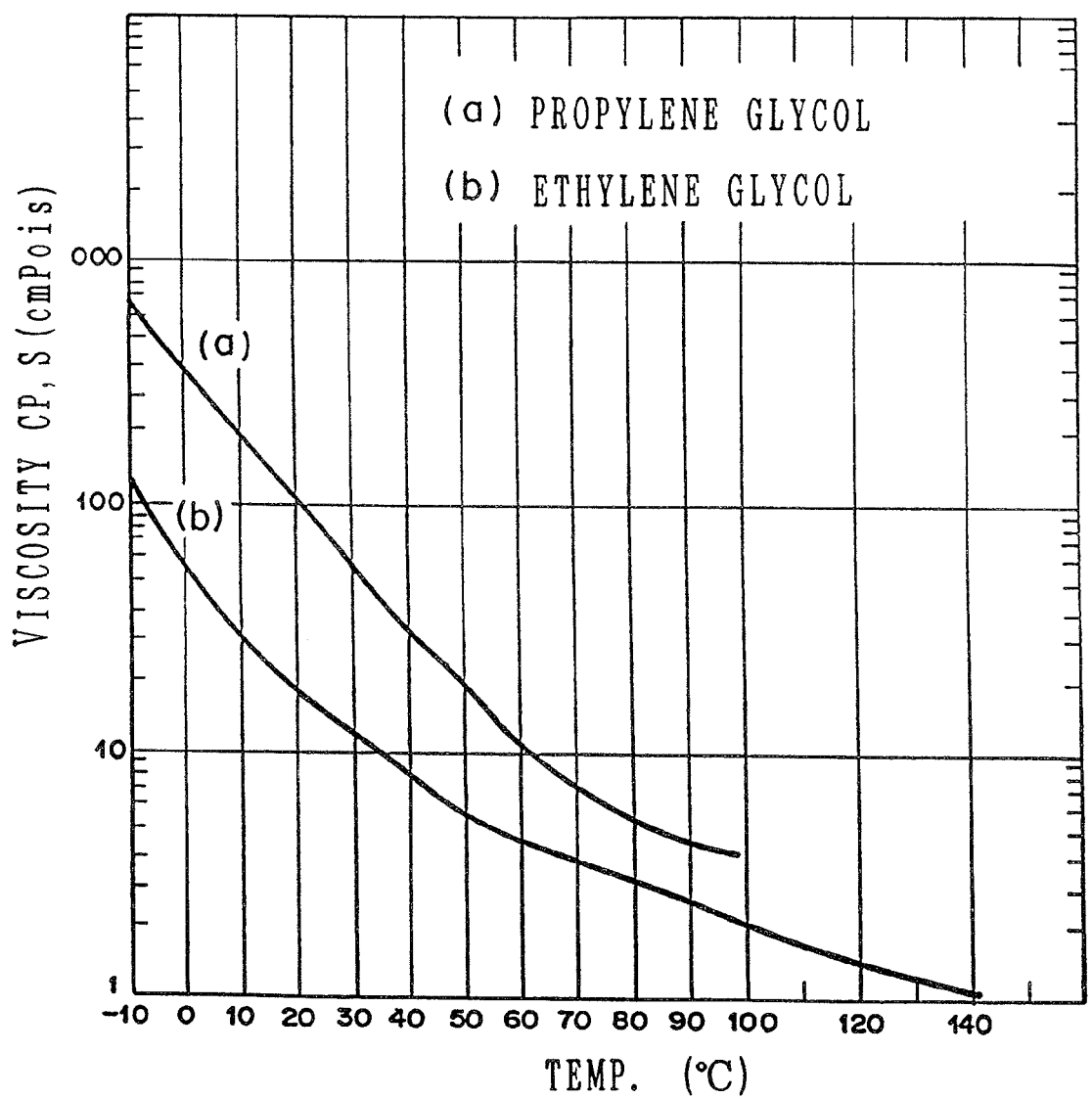
FIG. 4 is a graph showing the relationship between the viscosity of ethylene glycol and of propylene glycol and the temperature from minus 10° C. to 100-140° C.

Of the above-described solvents, solvents of polyvalent alcohols are more viscous, and among them ethylene glycol and propylene glycol are relatively easy to handle and easily available on the market. FIG. 4 shows the relationship between the viscosity and the temperature from minus 10° C. to 12° C. for both of them. With safety to the environment and to the persons who wear sanitary material taken into consideration, the most preferable organic solvent is propylene glycol (hereinafter abbreviated as the "PG").

Figure 5:
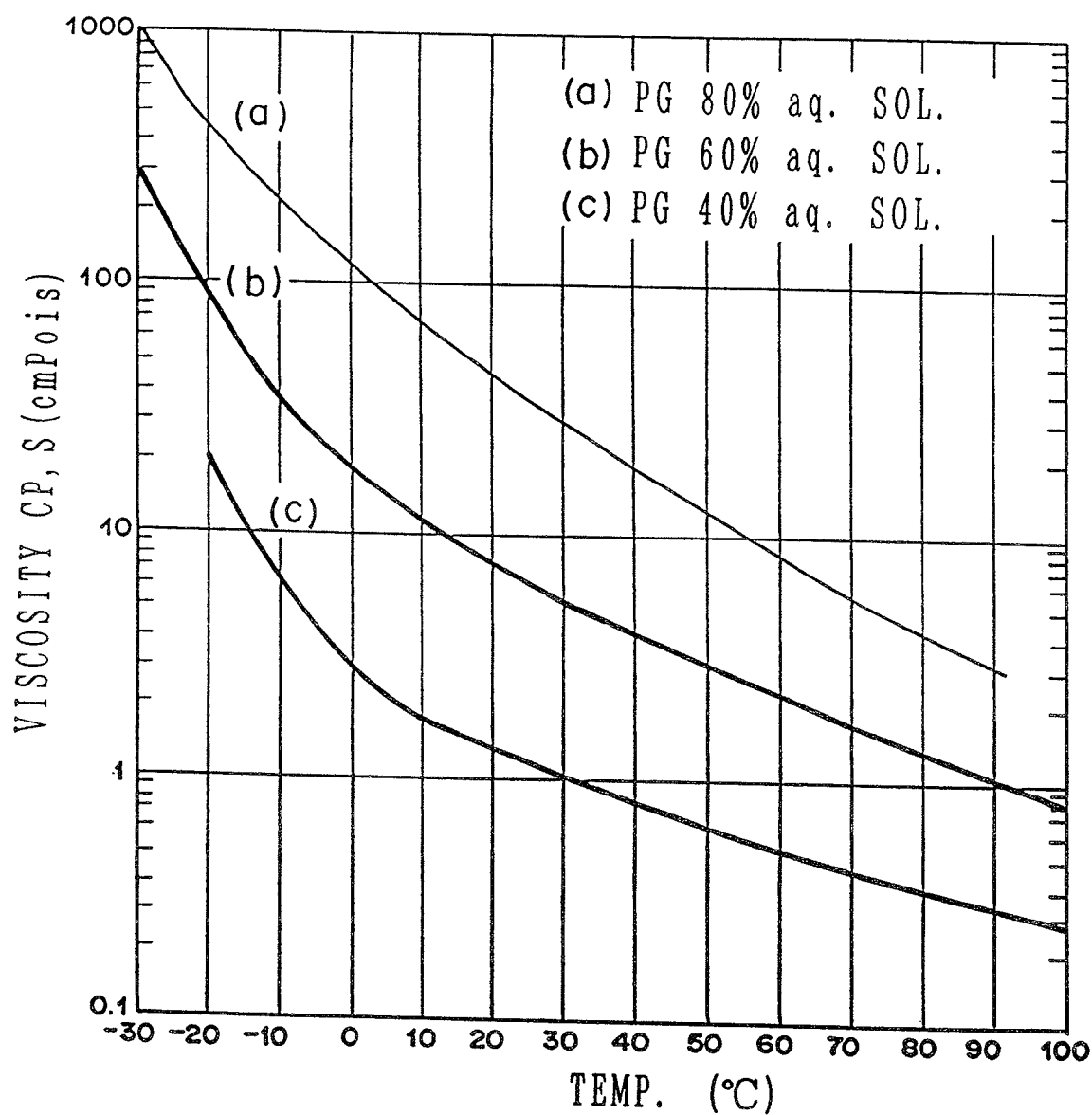
FIG. 5 is a graph showing the relationship between the viscosity of propylene glycol and the temperature in an aqueous solution for the cases of mixing ratios of 4/6, 6/4 and 8/2.

The above-described solvents are used mainly in mixture with water in the present invention. An appropriate mixture ratio between water and a solvent needs to be selected in order to prevent coagulation and swelling of the SAP particles and to disperse stably the SAP particles with the MFC and the short-cut staple fiber component. The mixture ratio of solventwater is approximately 9/1 to 5/5. If water is more than 5/5, the swelling of the SAP is rapidly increased, and if a solvent is more than 9/1, the MFC starts to settle. The transition region and nature are somewhat different depending on the kinds of the solvents used. If the PG is taken as an example, a particularly preferable mixture ratio is 6/4 to 8/2. FIG. 5 shows the relationship between the viscosity and the temperature of the PG in an aqueous solution for the mixture ratios of 4/6, 6/4 and 8/2. It is shown that, as the content of water increases, the viscosity relatively decreases, and that a difference in viscosity caused by difference in temperature is large even when the solvent is in an aqueous solution.

On the other hand, in order to hydrate and disperse the HFFM stably, it is more advantageous to have higher content of water in a dispersion medium. Therefore, an appropriate range of the ratio of an organic solvent/water is 90/10 to 40/60. Note that the ratio varies to some extent depending upon the organic solvents used and the properties of the SAP used.

The dispersion concentration each of the SAP and the HFFM in coexistence in this dispersion medium and the ratio in concentration between the SAP and the HFFM are described in more detail below. The concentration of the SAP is selected from a range of 60 percent or lower, preferably 50 percent to 5 percent from the standpoint of ease to handle, although it may be somewhat different depending upon the methods of slurry transportation. A preferable concentration of the HFFM is selected to obtain the bonding strength and the dispersion stability of the SAP. To maintain a good dispersion stability, the concentration of the HFFM needs to be 0.2 percent or higher, preferably 0.3 percent to 1.0 percent.

At this concentration of the HFFM, a dispersion medium containing the HFFM exhibits a good dispersion stability. Even after the medium is allowed to stand for a long period of time, no settling occurs.

Experimental results show that, as the concentration of the HFFM increases, the dispersion stability improves. When the concentration of the HFFM was 0.3 percent, no settling occurred for one hour. At the concentration of 0.5 percent, no settling occurred for 65 hours. It proves that, with this good dispersion stability, not only the coating procedure becomes easier, but also, the HFFM enclose the SAP particles completely so that a stable dispersion is realized.

As the ratio of the HFFM to the SAP (MFC/SAP×100(%)) increases, the strength of the absorbent composite becomes higher, but at the same time, the absorbent composite hardens to a paper-like hand. Therefore, the ratio of the HFFM to the SAP is preferably 20% or lower. On the other hand, at the ratio of 0.3% or lower, a sufficient bonding strength cannot be obtained. The bonding strength is evaluated by applying a cellophane adhesive tape method for measuring a surface strength. The results of applying the method to the evaluation of the bonding strength show that more preferable range of the ratio is 5% to 0.5%.

Figure 6:
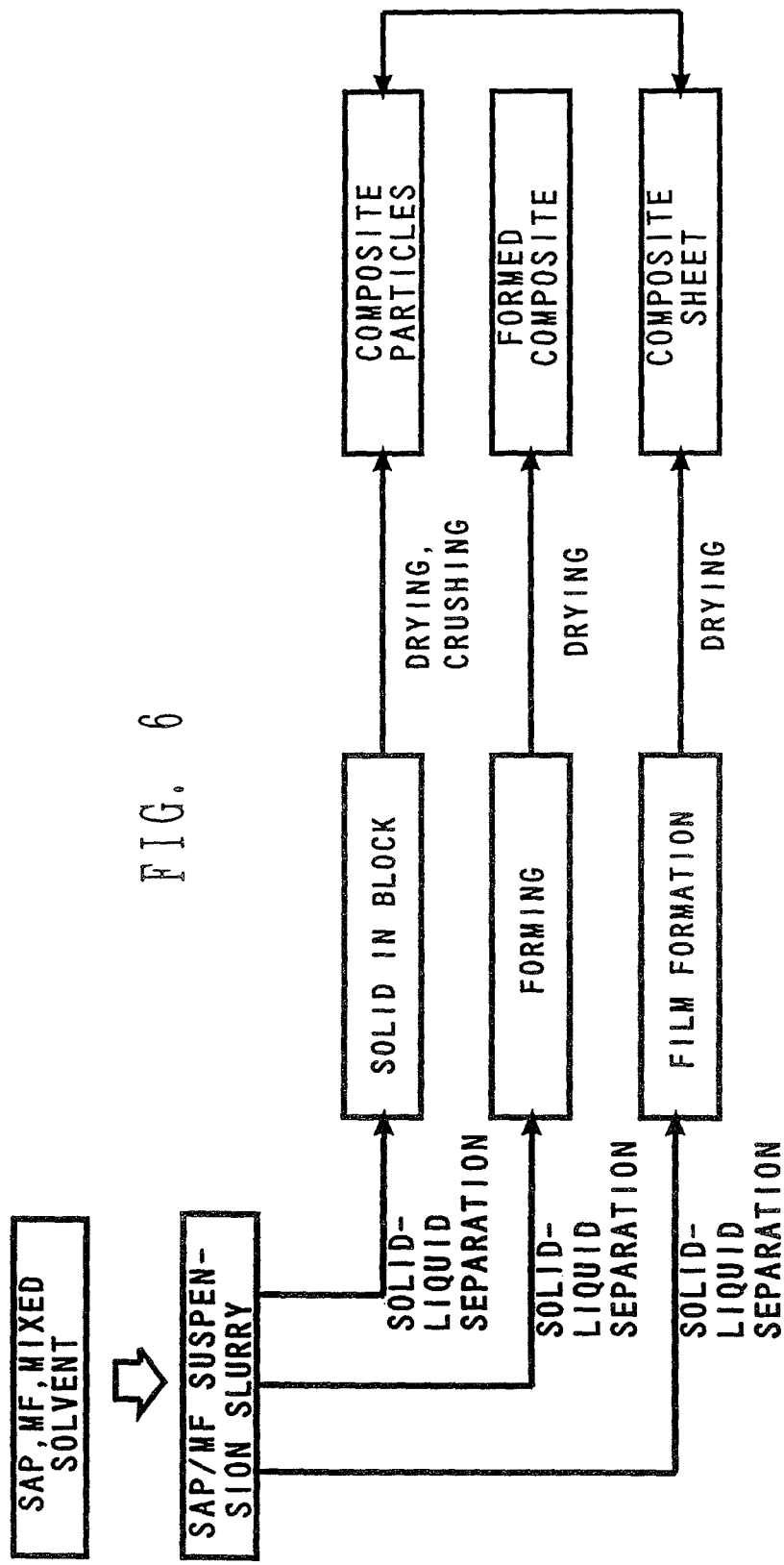
FIG. 6 is an explanatory diagram showing a concept of forming various absorbent composites from slurry dispersion liquids.

Next, a method of forming a composite from a dispersion liquid which is made by dispersing the HFFM and the SAP in a dispersion medium is described with reference to the accompanying drawings below. As a method of forming an absorbent composite from the above-described dispersion liquid slurry, for example, as shown in a conceptual drawing of FIG. 6, (1) by drying a block-like substance obtained by separating the solvent from the slurry and crushing the substance into particles, composite particles with the surface of the SAP covered by the HFFM, cubic-shaped as shown in FIG. 7(a) or flake-shaped as shown in FIG. 7(b), are obtained, (2) if the slurry is poured into a mold made of, for example, a net and solid and liquid components are separated and dried, a pellet-, rod-, cylinder-, or corrugated-plate-shaped three dimensional formed composite is obtained depending upon the mold used, and (3) if thin film is formed continuously and dried, a composite sheet is obtained.

An absorbent composite obtained in each of the above-described manners has flexibility depending upon the water content. Therefore, a composite sheet is formed in a mat shape together with fibers, for example, by an air-laid method and the mat is moistened, pressed, and dried so that it can be reformed into a sheet shaped composite.

Next, a method of directly forming a sheet from a dispersion liquid, which can be widely used, is described in detail. As described in the above, a network structure of the HFFM, while maintaining a condition where the SAP is stably and firmly held inside, enables the formation of a very thin layer. In other words, a dispersion liquid where the HFFM and the SAP are dispersed in a dispersion medium is applied onto a suitable flat surface, and a sheet-shaped highly absorbent composite can be formed which is composed of only the HFFM and the SAP.

A highly absorbent composite of a shape described in the above is shown in FIG. 8(a). In FIG. 8(a), reference numerals 11 and 12 represent the HFFM and the SAP particles, respectively. In fact, as shown in FIG. 8(b) which is a sketch of a microphotograph magnified by 70 times, each SAP particle is completely covered by the HFFM and at the same time, the SAP particles are taken in a network structure of the HFFM as the adjoining particles are entwined with each other by the HFFM.

Alternatively, when a dispersion liquid is applied onto a suitable supporting sheet, a highly absorbent composite sheet material composed of the supporting sheet and an absorbent composite layer is obtained after the dispersion liquid is dried. When a porous non-woven fabric is used as the supporting sheet, part of the dispersion liquid enters spaces made by the fibers of the non-woven fabric depending upon the density of the non-woven fabric, and a composite sheet where non-woven fabric 13 and the absorbent composite layer 10 are entwined as they are in contact with each other is formed as shown in FIG. 9(a) and FIG. 9(b) which is a sketch of a microphotograph, after the liquid is dried. A preferable density of the non-woven fabric is 0.2 g/cm$^3$ or lower in terms of the apparent specific density, and, more preferably, 0.01 to 0.1 g/cm$^3$.

Preferable fibers constituting the non-woven fabric are, from a viewpoint of the permeability of a liquid, a hydrophilic material such as cotton, rayon and wood pulp or synthetic fibers treated to be hydrophilic such as polyethylene, polypropylene and polyester. In particular, the HFFM which is of the S-MFC or the BC has a very strong hydrogen bonding strength in addition to being easily entangled physically. Therefore, when a cellulosic supporting sheet is used, such HFFM is more strongly and stably bonded with each other and with the supporting sheet in a dry state, and exhibits an outstanding permeability in a wet state.

In addition, in a structure as shown in FIG. 9, other sheet material 14 can be bonded in contact with the highly absorbent composite layer 10 as against the non-woven fabric 13, as shown in FIG. 10. If, as this other material 14, a liquid impervious sheet material is used, the composite sheet of FIG. 10 alone may have the function of an absorbent product composed of a topsheet, an absorbent, and a backsheet.

Figure 11:
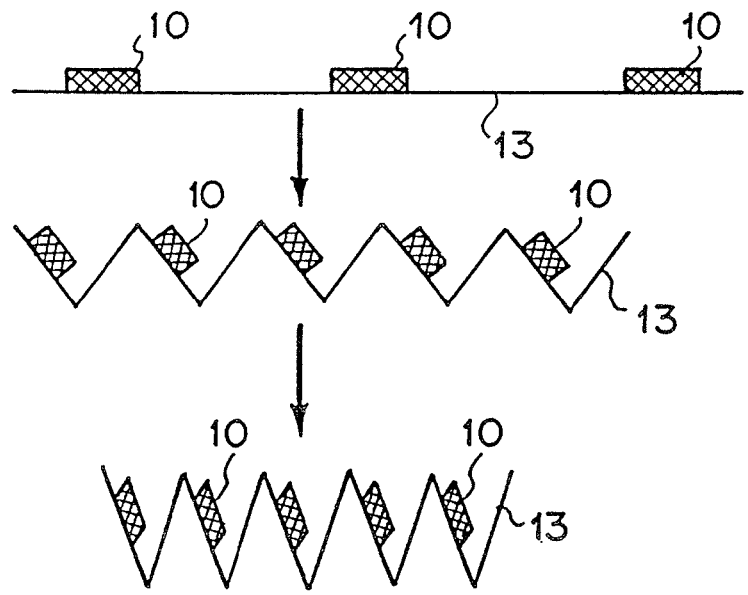
FIG. 11 is a longitudinal sectional view of a composite sheet material embodying the present invention.
Figure 12:
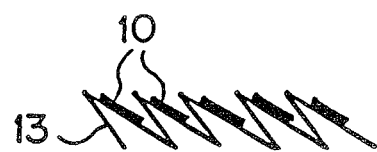
FIG. 12 is a longitudinal sectional view of a composite sheet material embodying the present invention.
Figure 13:
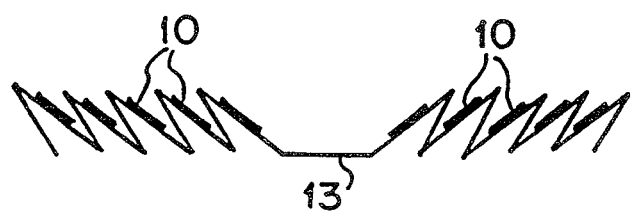
FIG. 13 is a longitudinal sectional view of a composite sheet material embodying the present invention.

Furthermore, in the structure of FIG. 9, a highly absorbent composite layer can be provided not only on the whole front surface of a supporting sheet, but also partially in a desired pattern. For example, as shown in FIG. 11, a plurality of the absorbent composite layers 10 are provided in bands of a desired width at prescribed intervals only on either surface of the supporting sheet 13, with the composite supporting sheet folded in between the adjoining absorbent composite layers in a zigzag pattern. Since a composite sheet of this structure has a larger volume of the absorbent composite layer 10 per unit area than a flat composite sheet, and accordingly a higher absorbing capability than the latter. Alternatively, as shown in FIG. 12, when the top portions of the zigzag pattern are largely brought down in one direction, the volume of the absorbent composite layer 10 per unit area can be further increased. In addition, as shown in FIG. 13, the top portions of the zigzag pattern can be brought down outwardly in mutually opposing directions to either side with a flat area provided in the center.

Such a zigzag structure provides a free and sufficient space that enables the SAP as used in an absorbent product to easily swell by absorbing a liquid.

Figure 14:
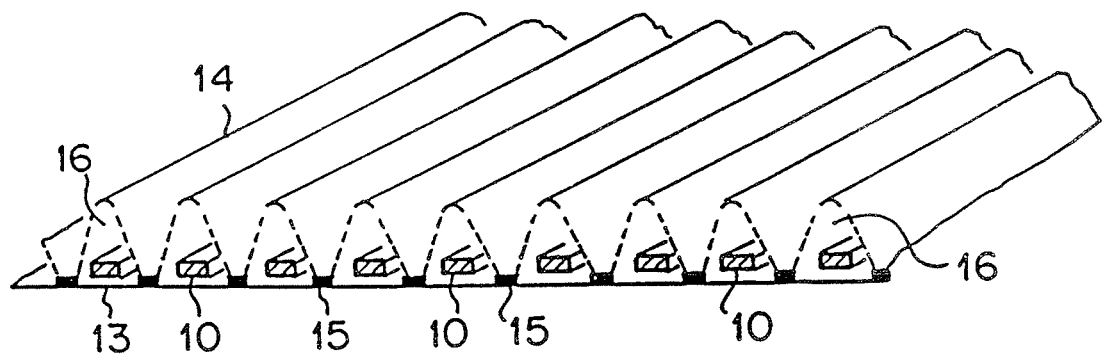
FIG. 14 is a partial perspective view of a composite sheet material embodying the present invention.

FIG. 14 shows an example of a highly absorbent composite sheet material as composed according to the present invention. This highly absorbent composite sheet material has a structure where a highly absorbent composite layer 10 is disposed in bands extending in parallel to each other at prescribed intervals on either surface of the supporting sheet 13 made of a elastic substance, over the highly absorbent composite layer a corrugated (zigzag) liquid pervious non-woven fabric 14 is disposed, and in the bottom portions of the zigzag of the non-woven fabric 14 the non-woven fabric 14 and the supporting sheet 13 are bonded in the bonding areas 15. Thus, each highly absorbent composite layer 10 is contained in the channel 16 which is formed between the supporting sheet 13 and the non-woven fabric 14. A highly absorbent composite sheet material of a structure described in the above can be preferably used, for example, in absorbent products such as feminine hygiene products and diapers, as highly elastic and absorbent sheet material: the highly absorbent composite sheet material has a high elasticity in the direction perpendicular to the longitudinal direction of the highly absorbent composite layer 10. In this case, the non-woven fabric 14 is used in contact with the body of a wearer, and body exudates of the wearer are first absorbed by and distributed in the non-woven fabric 14 and then absorbed by the highly absorbent composite layer 10. As the absorbed amount of body exudates increases, the volume of the highly absorbent composite layer 10 increases. However, since each band of the highly absorbent composite layer 10 is contained in the channel 16 formed between the supporting sheet 13 and the non-woven fabric 14, the layer is allowed to swell freely.

Figure 15:
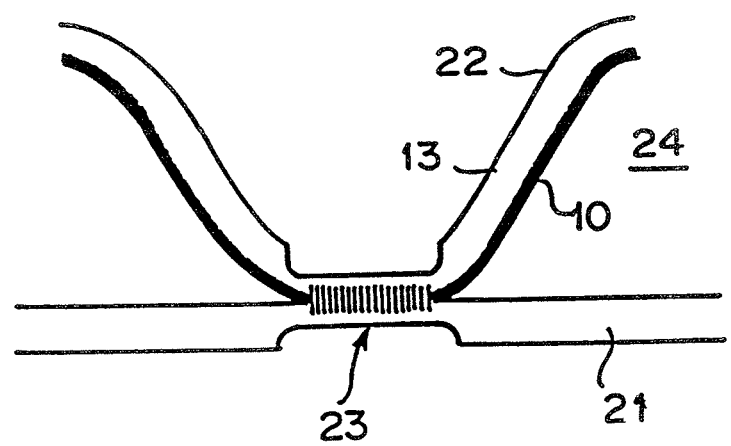
FIG. 15 is a longitudinal sectional view of a composite sheet material embodying the present invention.

FIG. 15 shows a highly absorbent composite sheet material embodying the present invention. A liquid impervious sheet designated by reference numeral 21 in FIG. 15 is liquid impervious and reasonably elastic. A highly absorbent composite sheet material 22 is laid on top of the liquid impervious sheet 21. Both of them are bonded with each other at many bonding areas 23 extending in lines or bands parallel with each other disposed at prescribed intervals. The bonding areas 23 are formed by thermally fusing, by a conventional method such as heat sealing and high frequency bonding, the liquid impervious sheet 21 and the highly absorbent composite sheet material 22 with a predetermined width. In between the adjoining bonding areas 23 and 23, the length of the highly absorbent composite sheet material 22 is longer than the length of the liquid impervious sheet 21, and, therefore, in between the bonding areas 23 and 23, a channel 24 is formed between the highly absorbent composite sheet material 22 and the liquid impervious sheet 21 by the sagging of the former. The highly absorbent composite sheet material 22 has a structure, as shown in FIG. 15, where, on either surface of a supporting sheet 13 of spun-bond or dry-laid non-woven fabric made of polyolefin such as PP and PE, an absorbent composite layer 10 is supported which layer 10 is disposed on the side facing the liquid impervious sheet 21. A sheet product of this structure is outstanding in retaining stably its own sheet shape even when the sheet product absorbs a large amount of liquid.

Figure 16:
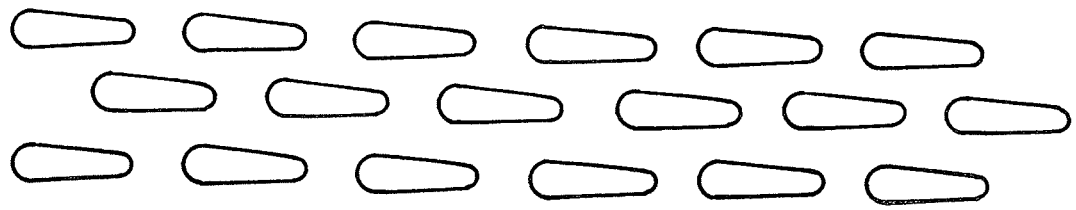
FIG. 16 is an explanatory drawing typically showing an example of an absorbent sheet having a distribution of patterns.
Figure 17:
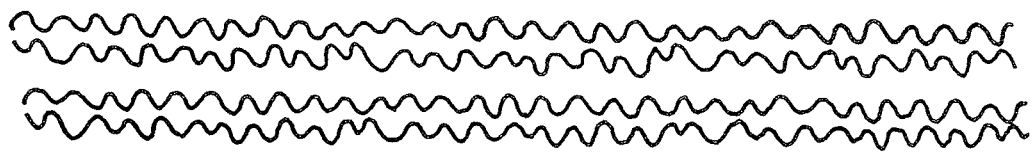
FIG. 17 is an explanatory drawing typically showing another example of an absorbent sheet having a distribution of patterns.
Figure 18:
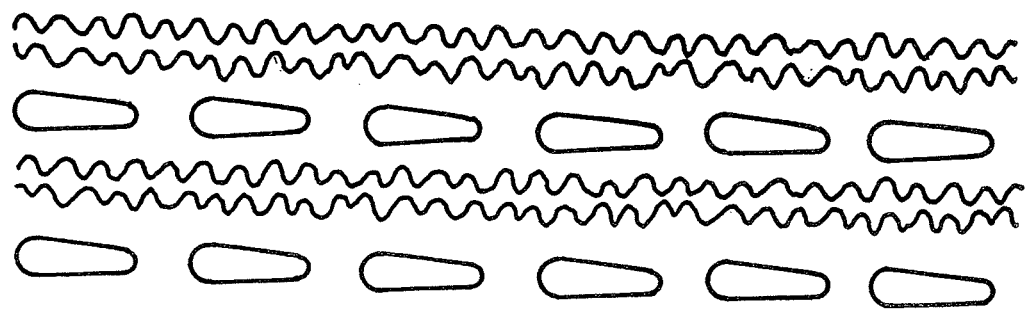
FIG. 18 is an explanatory drawing typically showing still other example of an absorbent sheet having a distribution of patterns.

FIGS. 16 to 18 show typically examples of an absorbent sheet having a distribution of patterns as obtained by the above-described means. FIG. 16 shows a pattern made by utilizing pulsation, FIG. 17 shows a pattern made by utilizing a branched nozzle, and FIG. 18 shows a pattern made in combination of the two. Examples of a distribution of higher absorbing regions are classified into the following three types: (1) on top of a thin absorbent layer distributed on the whole area a partially thick layer exists; (2) parts of a supporting sheet exposed without any absorbent layer, and parts thereof with such absorbent layer exist separately; and (3) in the higher absorbing regions thin and thick layers coexist. The distribution pattern of high absorbing regions is, for example, a pattern of islands in the sea as shown in FIG. 16, a continuous band-type pattern with a thin margin as shown in FIG. 17, and a combination of island and band patterns as shown in FIG. 18. An absorbent sheet which is coated with a slurry in a distribution of patterns is bonded with a supporting sheet stably by press, and the structure is fixed by removing the liquid component and drying. In doing so, a absorbent sheet yet to be dried which has a distribution of patterns, is high in difference in thickness, and contains a lot of solvent is likely to adhere on a press roll and to partially peel off. To prevent this, a means of pressing an absorbent sheet covered with tissue or non-woven fabric is available, but an effective means is as follows: an absorbent sheet is first heat pressed to fit well a supporting sheet and the absorbent layer on the roll is subjected to removal of the liquid component to fix the structure so that the surface is stabilized. Then, if peeling is done only after the surface is thus stabilized, no absorbent sheet is wound on the roll without any covering.

FIGS. 19(A), (B), (C) and D) show typically the simplest shape of a absorbent tube of the present invention. In FIG. 19, reference numeral 401 represents a supporting sheet in tube, and 402 represents the SAP carried by the supporting sheet 401 only on the inner wall. In the absorbent tube as shown in FIG. 19(A) the supporting sheet 401 is formed having a cross-section of a closed ring, and made into tube with the adjoining of both ends bonded with an adhesive agent 403 such as hot melt type adhesive agent, and carries the SAP 402 nearly uniformly on the whole surface of the inner wall. In FIG. 19(B), a reinforcing sheet 404 is disposed at the adjoining point of both ends of the supporting sheet 401, and both ends of the supporting sheet 401 together with the reinforcing sheet 404 are bonded with the adhesive agent 403. In the absorbent tube of FIG. 19(C), a flat supporting sheet 401 carrying the SAP 402 on one surface is formed into tube only with one end of the supporting sheet 401 with the surface carrying the SAP 402 inside, and the side ends of both of them facing each other in opposition are adjoined as laid on top of each other with a appropriate width of margin provided and the portion where they are adjoined is bonded with the adhesive agent 403. Thus, on one end of the flat absorbent is a tube formed. In the absorbent tube of FIG. 19(D), on the side end disposed outside no SAP 402 exists, and, therefore, the adhesive agent 403 is directly applied on the surface of the supporting sheet 401.

As a supporting sheet which can be used in the present invention, substantially all kinds of sheet material composed of fiber web, if they are liquid pervious and do not have openings large enough for the SAP particles to pass through, can be used. Examples thereof are melt blown non-woven fabric, foamed net, extruded fibrillated net, spun-bond non-woven fabric, carded web non-woven fabric, spun-laced non-woven fabric, and any combinations of the foregoing materials.

The basic roles of this supporting sheet are to carry the SAP stably and, at the same time, to prevent the SAP swollen by absorbing a liquid from leaking and going out of an absorbent tube. If required, the supporting sheet can be given other roles by selecting the kinds and shapes of the constituting materials of the supporting sheet. For example, by selecting a cellulosic fiber or a blending with a cellulosic fiber as the fiber constituting the supporting sheet, the diffusion of liquid into carried SAP can be increased. Also, another example of giving a different role is that, by using non-woven fabric which is of high elongation, can be elongated with a small force, for the supporting sheet, the sheet itself can be elongated by the absorption and swelling of the SAP. By utilizing these effects, the liquid absorbing capability of the SAP can be made to exhibit to the maximum extent, and the diameter of the absorbent tube while no liquid is absorbed can be made small which in turn makes small absorbent products using such small absorbent tube. In this specification, the term "high elongation" of a substance means the property that the substance can be elongated or extended easily by a small force applied at least in one direction.

Figure 20:
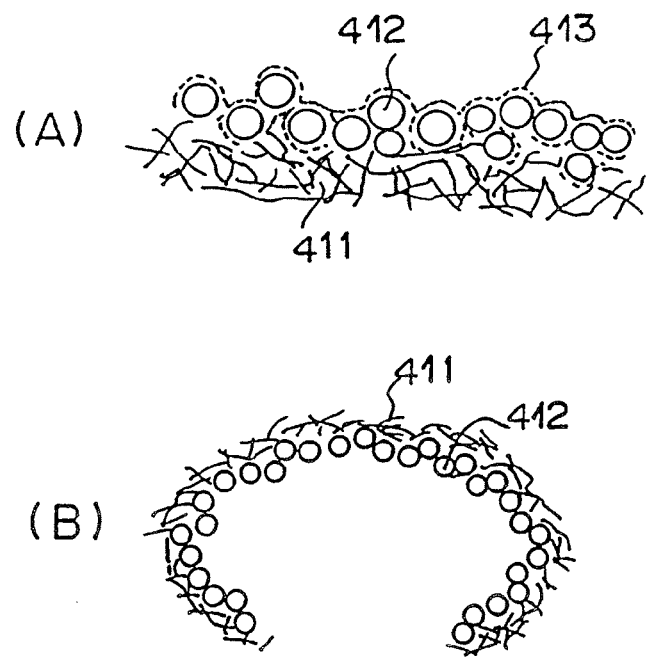
FIG. 20(A) is a sectional view of an absorbent sheet which can be used for the present invention.
FIG. 20(B) is a cross sectional view of an absorbent tube consisting of the absorbent sheet of FIG. 20(A)

A composite sheet obtained by this method has a structure, for example, as typically shown in FIG. 20(A). In FIG. 20(A), reference numeral 411 represents a supporting sheet, 412 represents the SAP, and 413 represents the HFFM which bonds the particles of the SAP 412 are bonded with each other and on the supporting sheet 411. Because this composite sheet can be formed as an extremely thin sheet as thin as 1 mm, it can be formed in tube as shown in FIG. 20(B), and is suitable as an absorbent tube of the present invention.

Figure 21:
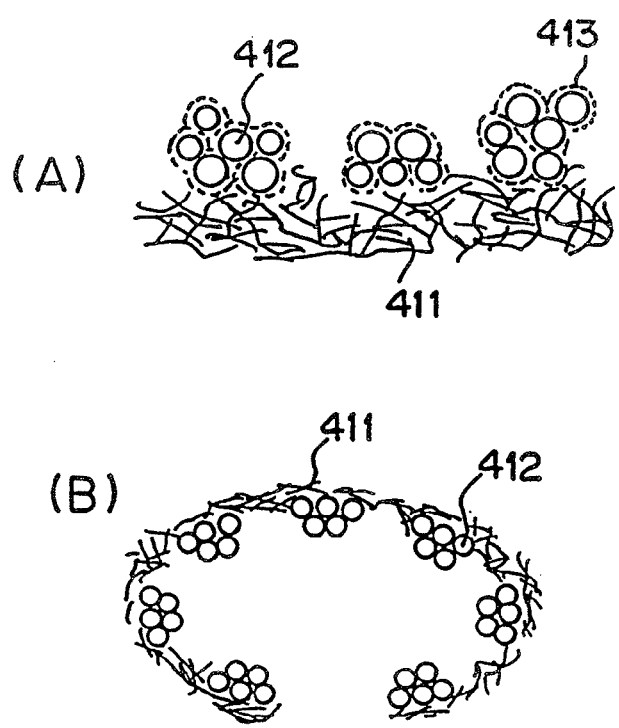
FIG. 21(A) is a sectional view of an absorbent sheet which can be used for the present invention.
FIG. 21(B) is a cross sectional view of an absorbent tube consisting of the absorbent sheet of FIG. 21(B)
Figure 22:
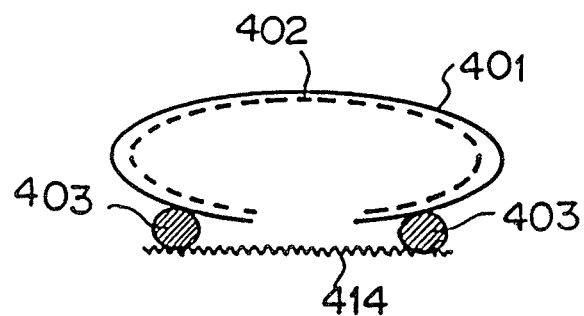
FIG. 22 is a cross sectional view of another example of an absorbent tube of the present invention.

FIG. 21(A) shows a composite sheet of a structure where, unlike an absorbent tube shown in FIG. 21(B) in which particles of the SAP 412 are distributed in nearly uniform density, blocks in which a plurality of the SAP 412 particles are gathered are formed which blocks are disposed in a suitable distribution. An absorbent tube as shown in FIG. 21(B) can be formed by Folding the composite sheet of FIG. 21(A) in the shape of a tube with the surface thereof carrying the SAP 412 particles facing inside. In the structures of FIG. 19 tubes in an O-letter shape are formed by directly bonding the side ends of the supporting sheet with each other, but in the structures of FIGS. 20(B), 21(B) and 22, tubes in a C-letter shape are formed where the side ends of a supporting sheet as it is made in such tube area bit away from each other. The absorbent of a tube in such C-letter may dispose a slit between the side ends of a supporting sheet facing either upward or downward. Also, another sheet material 414 may be bonded by means of adhesive 403 to the slit as shown in FIG. 22.

It should be noted that in the above description and in the sketches that are shown in the description to follow a absorbent tube is shown in a circle or ellipse or a shape that is somewhat swollen in order to help better understand it, but in fact, the absorbent tube before it absorbs liquid to swell takes a shape that is flat or collapsed.

One or a group of absorbent tubes having a structure described in the above can be incorporated into a conventional absorbent product as an absorbent core, but in practice, are advantageously used as linked to a sheet comprising an absorbent product. For example, one absorbent tube or a plurality of absorbent tubes disposed in parallel to each other comprises or comprise an absorbent core as linked in an absorbing region of an absorbent product to a liquid pervious inner sheet disposed on the side of the absorbent product in contact with the skin of a wearer or a leakage resistant outer sheet.

Figure 23:
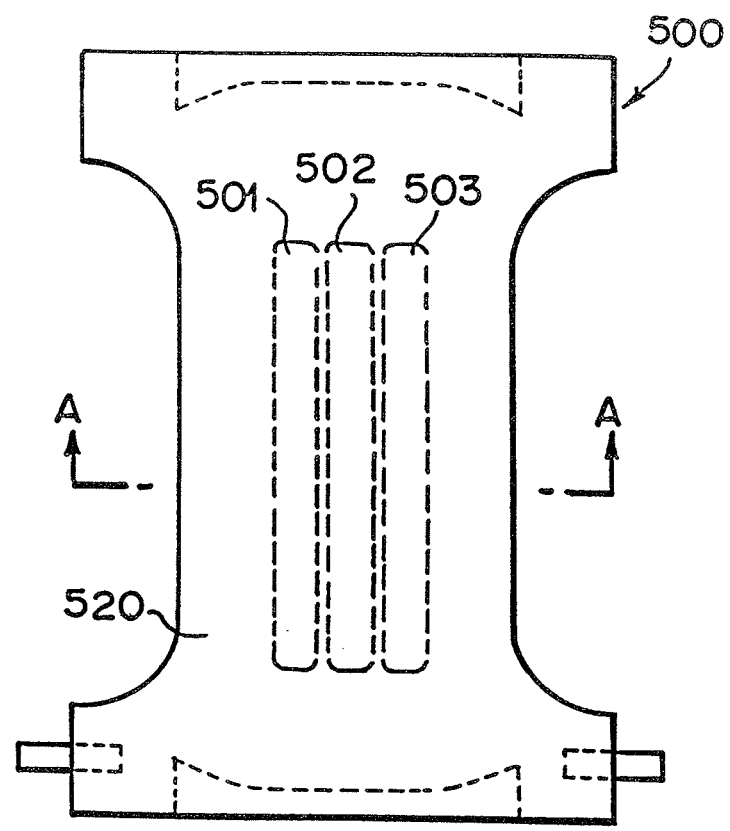
FIG. 23 is a plan view of an example of an absorbent product of the present invention.
Figure 24:
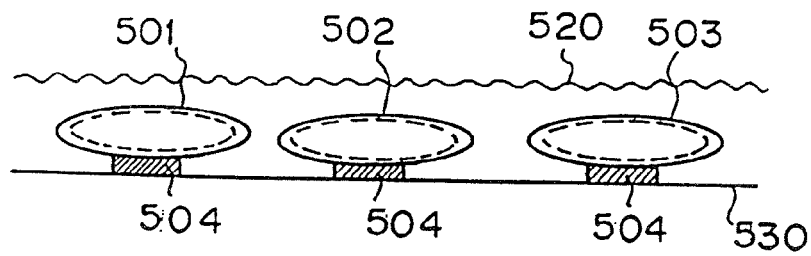
FIG. 24 is a fragmentary sectional view taken along section line A-A of FIG. 23.

FIG. 23 shows a disposable diaper as an absorbent product of the present invention having a structure described in the above. In FIG. 23, reference numeral 500 represents the body of an absorbent product. This body 500 is, as shown in FIG. 24, composed of a liquid pervious inner sheet 520 and of a liquid impervious outer sheet 530, and in its absorbing region three absorbent tubes 501, 502 and 503 disposed in parallel to each other are contained. The absorbent tubes 501, 502 and 503 are, in this embodiment of the present invention, linked to a liquid impervious outer sheet 530 by means of an adhesive 504 such as hot melt adhesive.

Figure 25:
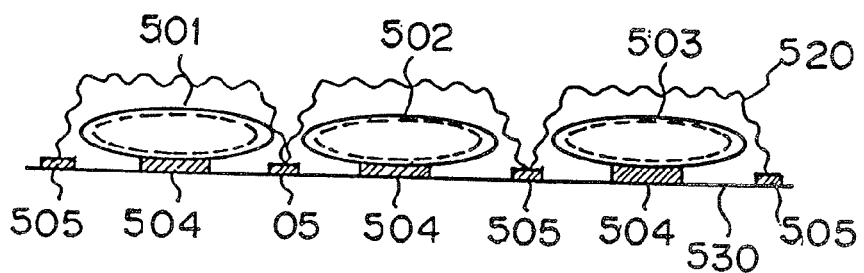
FIG. 25 is a sectional view of another absorbent product of the present invention as shown in the same way as in FIG. 23.

FIG. 25 shows a sectional view of the structure of another absorbent product of the present invention like FIG. 22. In this example, the inner sheet 520 is linked to the outer sheet 530 on both sides of the absorbent tube by adhesive 504.

Figure 26:
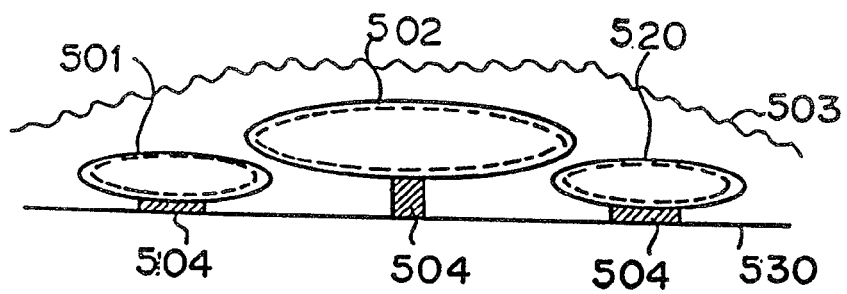
FIG. 26 is a sectional view of other absorbent product of the present invention as shown in the same way as in FIG. 23.

In the example of FIG. 26, the absorbent tube 502 disposed in the center is wider than the absorbent tubes 501 and 503 disposed on the respective sides of the absorbent tube 502 so that both side ends of the absorbent tube 502 are laid on the side ends of the absorbent tubes 501 and 503.

Figure 27:
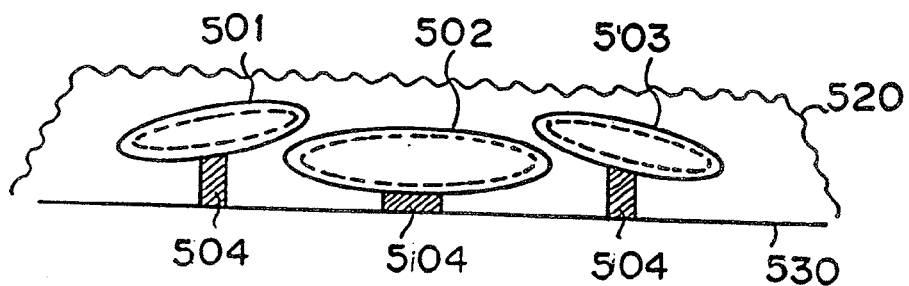
FIG. 27 is a sectional view of still other absorbent product of the present invention as shown in the same way as in FIG. 23.

In the example of FIG. 27, the relation in widths among the absorbent tubes 501, 502 and 503 is the same as in the example of FIG. 26, but the absorbent tubes 501 and 503 on the sides are disposed at positions higher than the absorbent tube 502 disposed in the center and the inside ends of the absorbent tubes 501 and 503 are laid on the side ends of the absorbent tube 502.

Figure 28:
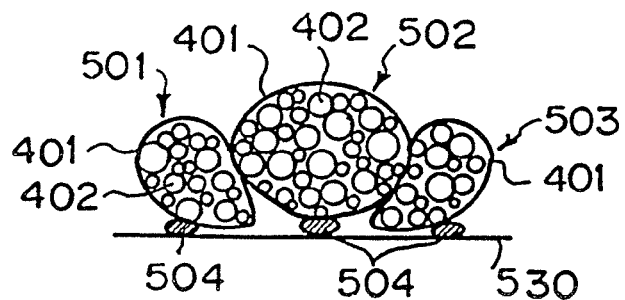
FIG. 28 is a sectional view of an absorbent tube, as swollen, used in the absorbent product of the present invention as shown in FIG. 24.

The absorbent products of the present invention provided with an absorbent core of a configuration shown each in FIGS. 24 to 27 exhibit a high absorbing property with the absorbing capability of the above-described absorbent tubes. Particularly, in a configuration as shown in FIGS. 26 and 27 where each absorbent tube is partially laid on an adjoining absorbent tube, because the amount of the SAP per unit area can be made larger, further higher absorbing property can be expected. For example, a condition where the absorbent tubes 501, 502 and 503 have absorbed to swell in a configuration of FIG. 26 is shown in FIG. 28. Also, in examples of FIGS. 24 to 27, each absorbent tube may be linked to the inner sheet 520, too, so that the absorbent tube may be secured in position.

Figure 29:
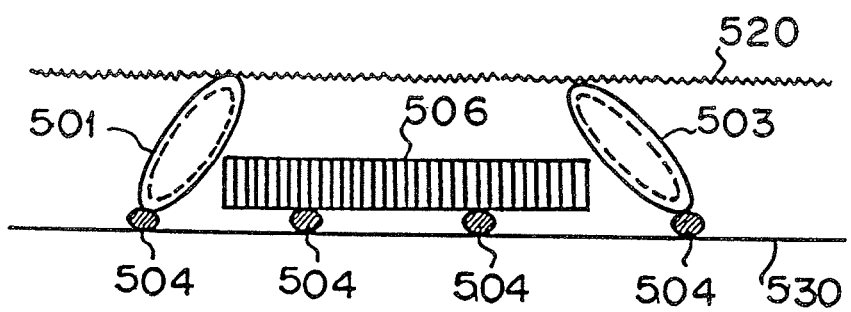
FIG. 29 is a sectional view of still other absorbent of the present invention as shown in the same way as in FIG. 23.

In the absorbent products of the present invention, an absorbent core to be disposed in an absorbing region may be comprised only by a plurality of absorbent materials, as described in the above, but one of the absorbent tubes may be replaced by another absorbent 506, as shown in FIG. 29.

Figure 30:
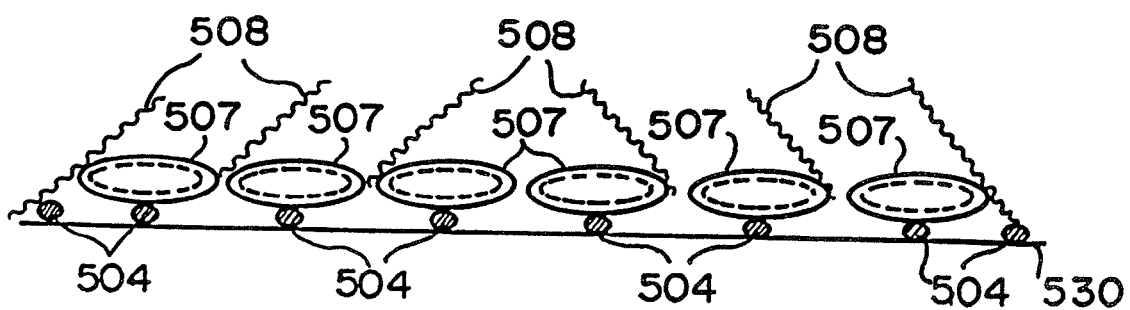
FIG. 30 is a sectional view of still other absorbent of the present invention as shown in the same way as in FIG. 23.

Alternatively, as shown in FIG. 30, a configuration can be made where absorbent tubes of long length and narrow width 507 are disposed in parallel to each other and tapes 508 made of a soft hand sheet such as non-woven fabric extending along the outer sides of each absorbent tube are disposed. This tape 508 allows a liquid coming to the absorbing region to reach the absorbent tube 507 and at the same time improves the touch existing between the absorbent tube and the skin of a wearer.

The number and the size of the absorbent tubes disposed in the absorbing region of an absorbent product can be selected depending upon the shape, use and desired absorbing property of the absorbent product, and the selection can easily be made by those skilled in the art.

Figure 31:
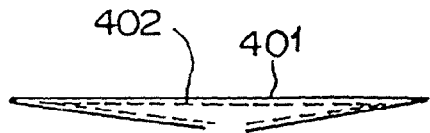
FIG. 31 is a cross sectional view of other example of the absorbent tube of the present invention.
Figure 32:
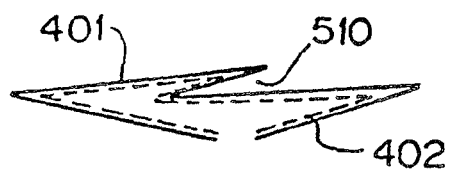
FIG. 32 is a cross sectional view of other example of the absorbent tube of the present invention.
Figure 33:
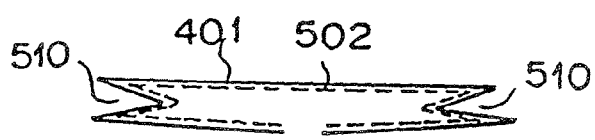
FIG. 33 is a cross sectional view of other example of the absorbent tube of the present invention.
Figure 34:
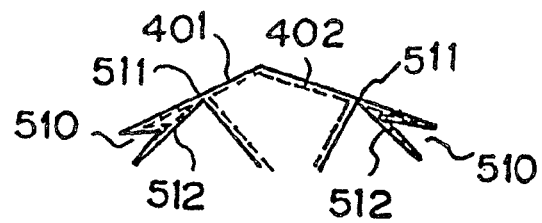
FIG. 34 is a cross sectional view of other example of the absorbent tube of the present invention.
Figure 35:
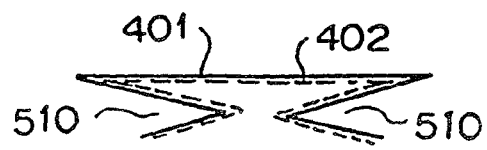
FIG. 35 is a cross sectional view of other example of the absorbent tube of the present invention.

In the descriptions and drawings made and shown in the above, the above-mentioned absorbent tubes are shown to have a virtually ellipsoidal cross-section, but the absorbent tube is normally thin having a flat shape before it absorbs a liquid to swell, as shown in FIG. 31. If the absorbent tube is of a single layer, the circumference length of the cross-section is constant regardless of the shape of the cross-section. The longer the circumference length is, the larger the area becomes to be provided to carry the SAP 402, and when the SAP 402 swells and increases in volume, the thickness or the height of the absorbent tube becomes larger. FIGS. 32 to 35 show examples where the supporting sheet 401 is provided with a gusset for such purpose. In the example of FIG. 32, a gusset 510 is disposed on the top surface of the absorbent tube, and in the examples of FIGS. 33 to 35, a gusset 510 is disposed on each side end of the absorbent tube. Note that in FIG. 34 the side ends on which gussets 510 are provided are linked at portions facing each other by heat sealing 511, forming a cell 512 as distinguished from the rest.

Figure 36:
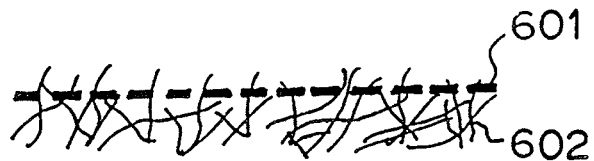
FIG. 36 is a sectional view of a supporting sheet which can be used to constitute the absorbent tube of the present invention.

In the absorbent tube of the present invention, a supporting sheet can be composed of any sheet material which is liquid pervious and has some degree of softness and tear strength. A preferable material is a non-woven fabric 601 as described in the above, and a non-woven fabric of an absorbent composite as shown in FIG. 36 can also be advantageously used. This composite non-woven fabric 601 may be made by composing one or two kinds of staple fiber 602 such as PET and rayon with spun bond non-woven fabric 601 made of synthetic fiber such as polypropylene by means of water jet entanglement. A composite non-woven fabric like this has a feature where the spun bond non-woven fabric 601 functions as the inner sheet and, as shown in FIG. 37, on the surface of the staple fiber the SAP 402 particles are securely held so that there is no need to cover the absorbent core with the inner sheet.

Figure 37:
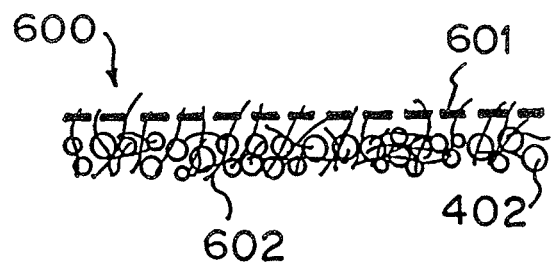
FIG. 37 is a sectional view show the condition where the SAP particles are carried and held by the supporting sheet of FIG. 37.
Figure 38:
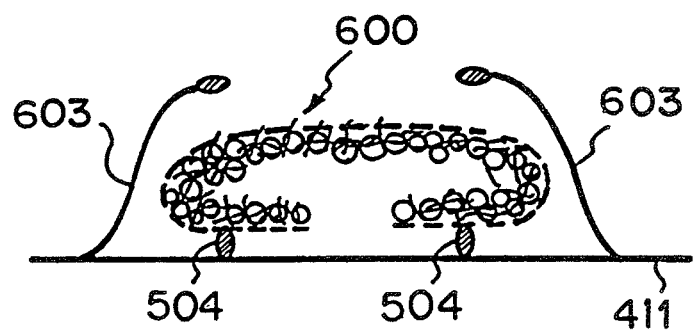
FIG. 38 is a fragmentary sectional view of an absorbent product constituted by using an absorbent tube having the structure of FIG. 37.

FIG. 38 shows an absorbent product of a structure where the absorbent sheet 600 of FIG. 37 is formed into a tube and linked to the outer sheet 411 of an absorbent product by means of adhesive 504, and on both sides leg gathers 603 are provided composed of a liquid impervious sheet. Either side of each leg gather 603 is linked to the outer sheet 411, and the other side is made to face the end of the other leg gather 603 at some interval in which interval the center portion of the absorbent tube 600 is located.

Figure 39:
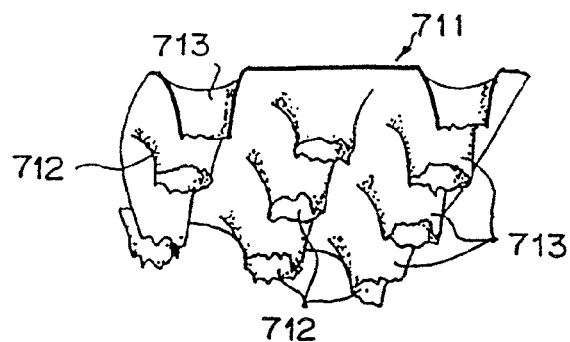
FIG. 39 is a partial perspective view of a porous liquid impervious sheet constituting the absorbent of the present invention.
Figure 40:
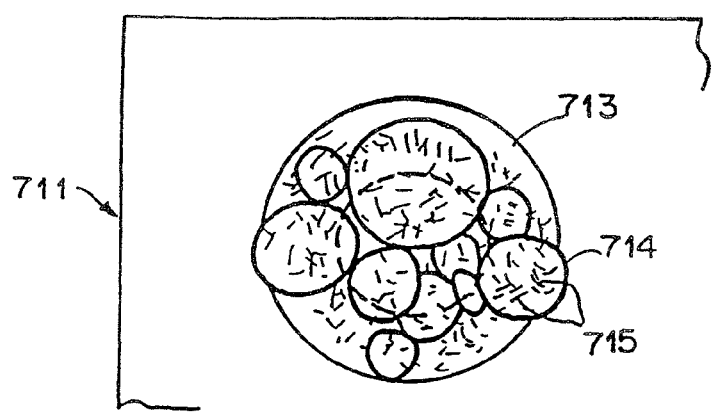
FIG. 40 is a plan view showing a part of the surface of the absorbent sheet of the present
Figure 41:
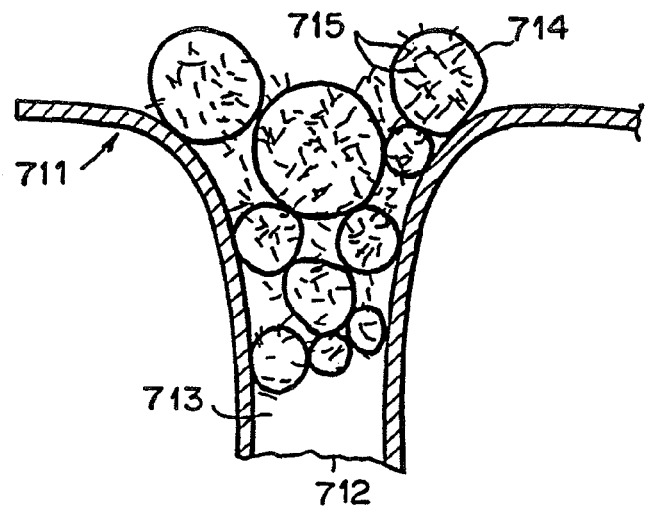
FIG. 41 is a longitudinal sectional view of the absorbent sheet of FIG. 40.

Other examples of an absorbent sheet of the present invention are described with reference to the accompanying drawings:

FIG. 39 shows a sheet material where on a liquid impervious sheet material 711 made of flexible thermoplastic film many dents 713 are formed having openings 712 in the bottom. An absorbent sheet where the dents 713 are filled with absorbent material is shown in FIGS. 40 and 41. The absorbent material is made by fixing the SAP particles 714 on the inner wall of the dent 713 of the liquid impervious sheet material 711 with the HFFM 715.

In general, such a structure is preferable as smaller dents are filled with finer particles and larger dents are filled with coarser particles.

Figure 42:
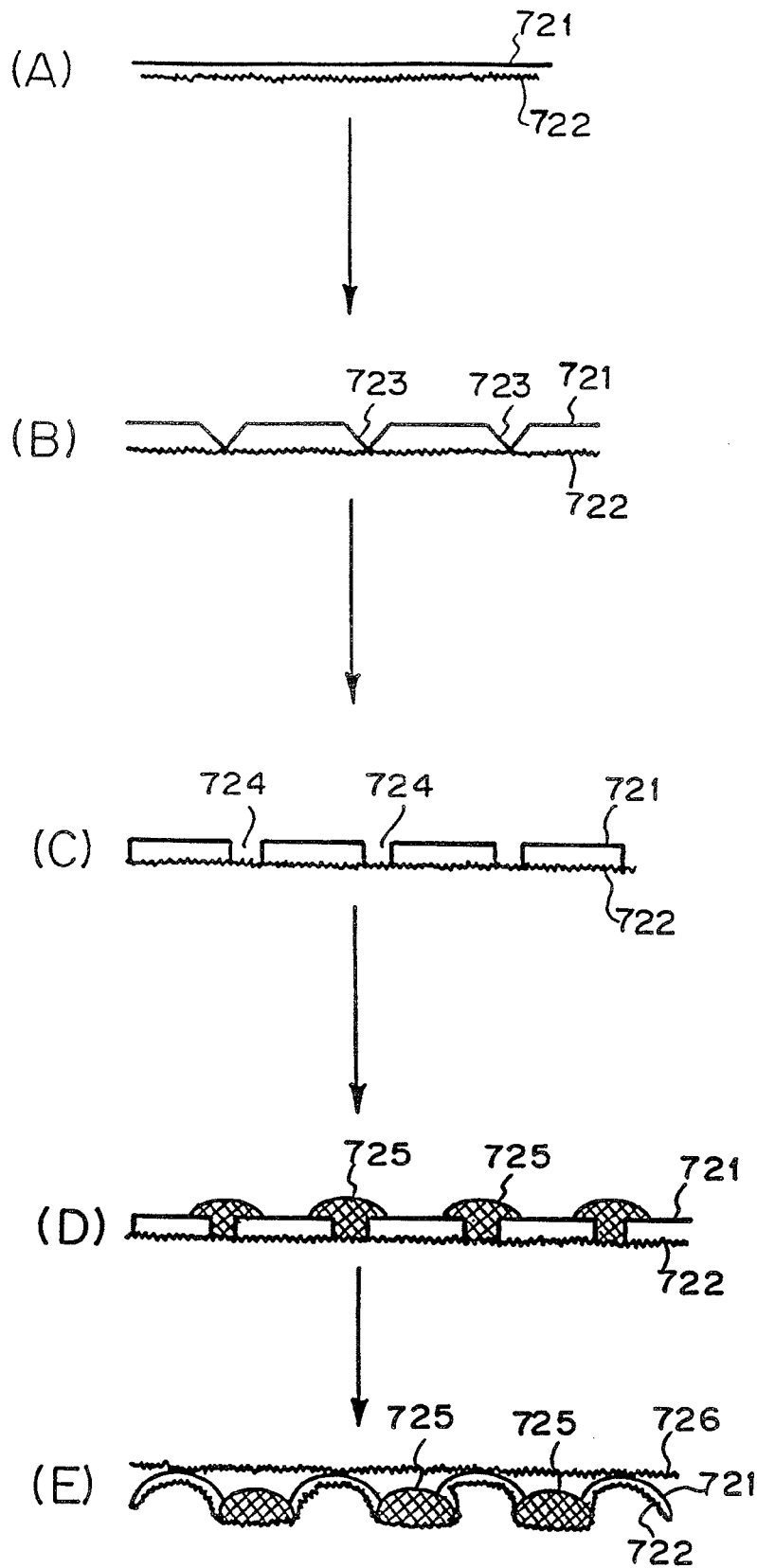
FIGS. 42 (A) to (E) are schematic diagrams showing a process of making the absorbent sheet of the present invention.

Also, FIG. 42 shows the steps of making other absorbent sheet of the present invention. In the step of FIG. 42(A) a liquid impervious sheet material 721 and a liquid pervious non-woven fabric 722 having a lateral extensibility are laid one each other with a hot melt adhesive layer (not shown) in between, and in the step of FIG. 42(B) many grooved portions 723 extending in parallel to each other are formed by means of hated grid roll, and at the same time, the liquid impervious sheet material 721 is bonded with the liquid pervious non-woven fabric 722 at the positions of the grooves with hot melt in between. This composite sheet is, in the step of FIG. 42(*c*), extended in a direction perpendicular to the longitudinal direction of the grooved portion 723, whereby the liquid impervious sheet material 721 is cut off at the positions of the grooves 723 to form dents 724. The dent portion is made up of only the liquid pervious non-woven fabric. Next, in the step of FIG. 42(D), slurry where the SAP and the HFFM are uniformly dispersed in a dispersion medium of a water miscible organic solvent and water is applied onto the liquid pervious sheet material 724 and then after removing the liquid component and drying, the dents 724 are filled with absorbent material 725 composed of the SAP and the HFFM. Lastly, in the step of FIG. 42(E), the topsheet 726 such as non-woven fabric is disposed on the liquid impervious sheet material 721 and the absorbent material 725 and the liquid impervious sheet material 721 and the absorbent material 725 are bonded to the topsheet 726 at the position 721 where no absorbent exists.

Figure 43:
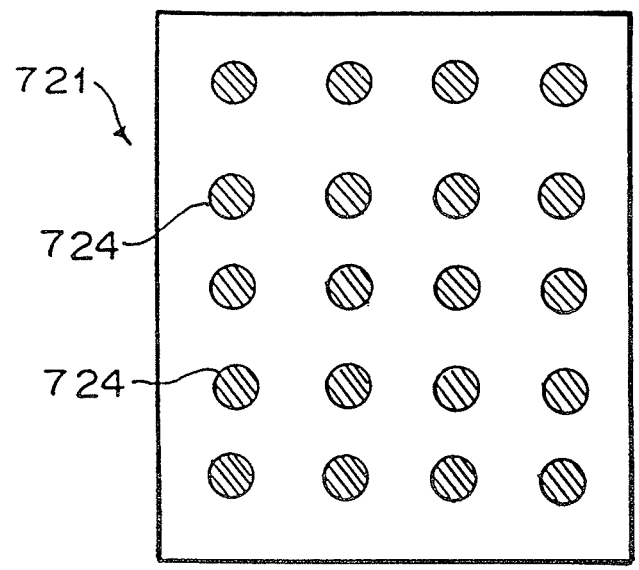
FIG. 43 is a plan view of a liquid impervious sheet material used for the absorbent sheet of the present invention.
Figure 44:
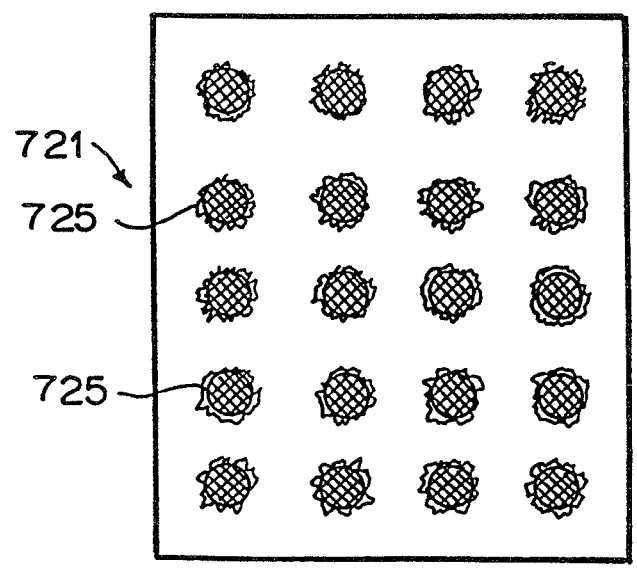
FIG. 44 is a plan view showing the condition where in the recesses of the liquid impervious sheet of FIG. 43 absorbent material is filled.

FIG. 43 shows a liquid impervious sheet material where the many dents formed in the step C of FIG. 42 are circular. FIG. 44 shows a sheet material where the dents 724 in the step D of FIG. 42 are filled with the absorbent material 725.

In the absorbent sheet as shown in FIG. 42, the non-woven fabric 722 constituting the composite sheet together with the liquid impervious sheet material 721 is preferably a non-woven fabric of 10 g/m² to 50 g/m² weight such as a non-woven fabric of a hydrophobic synthetic fiber such as PE, PP and PET and a non-woven fabric of a mixture of a synthetic fiber and a cellulosic fiber such as rayon, LYOCELL and cotton.

Figure 45:
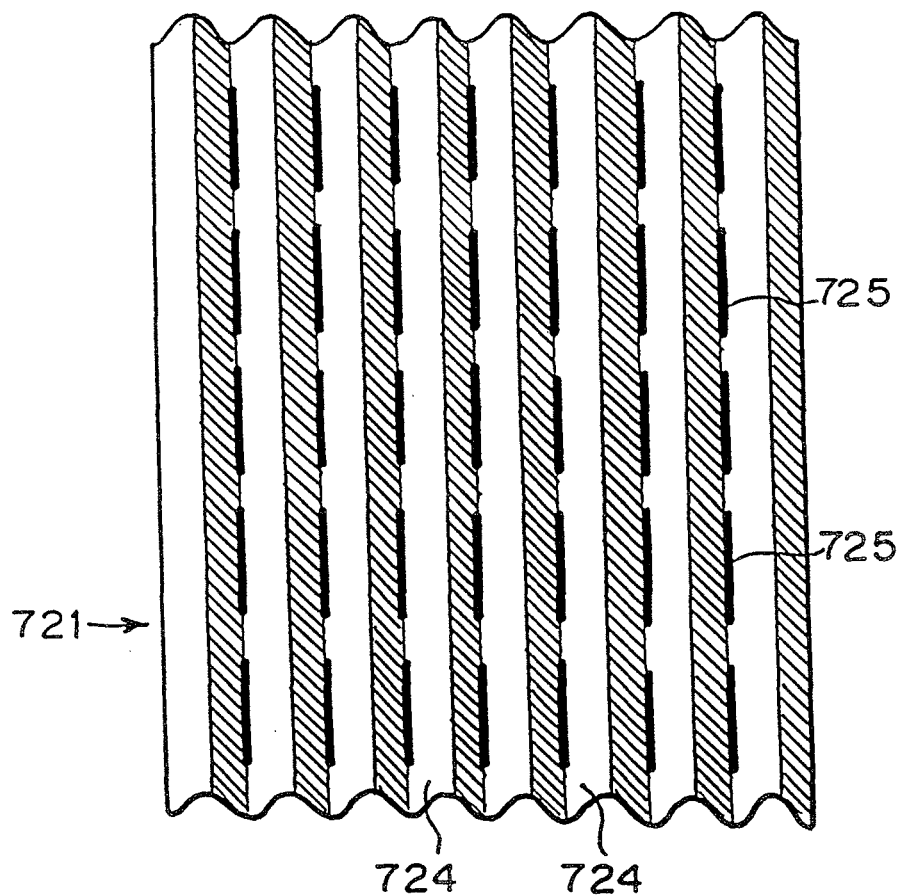
FIG. 45 is a fragmentary plan view showing other absorbent sheet of the present invention.
Figure 46:
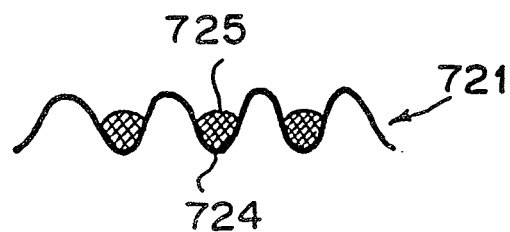
FIG. 46 is a fragmentary longitudinal sectional view of FIG. 45.

FIGS. 45 and 46 show configuration where a liquid impervious sheet material 721 is formed in a corrugated sheet and absorbent material 725 is disposed and fixed in narrow bands or in bars in the bottoms of dents 724 of V-letter shape extending in parallel to each other.

Figure 47:
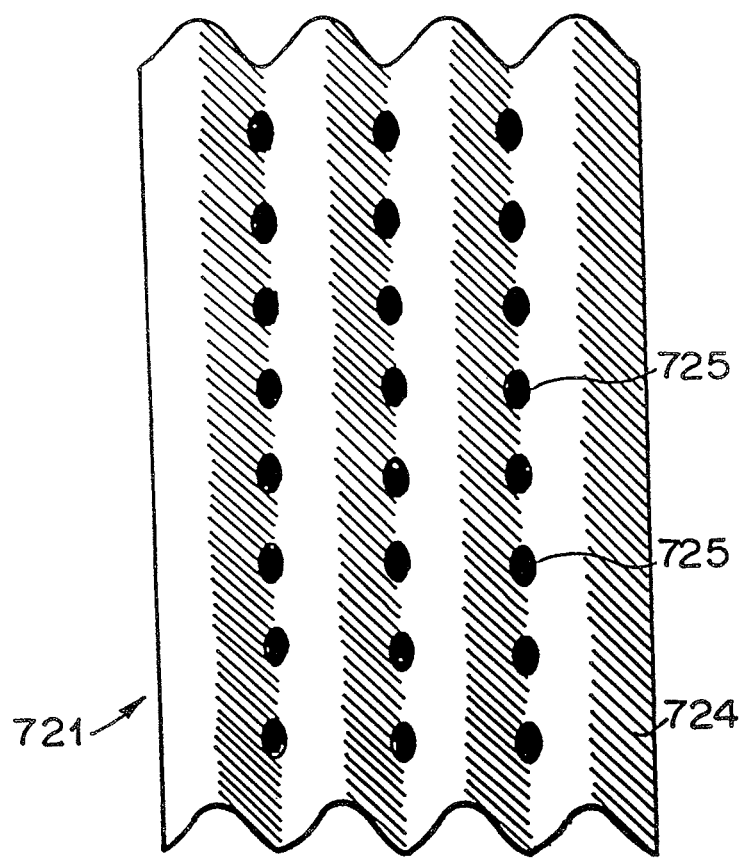
FIG. 47 is a fragmentary plan view showing still other absorbent sheet of the present invention.
Figure 48:
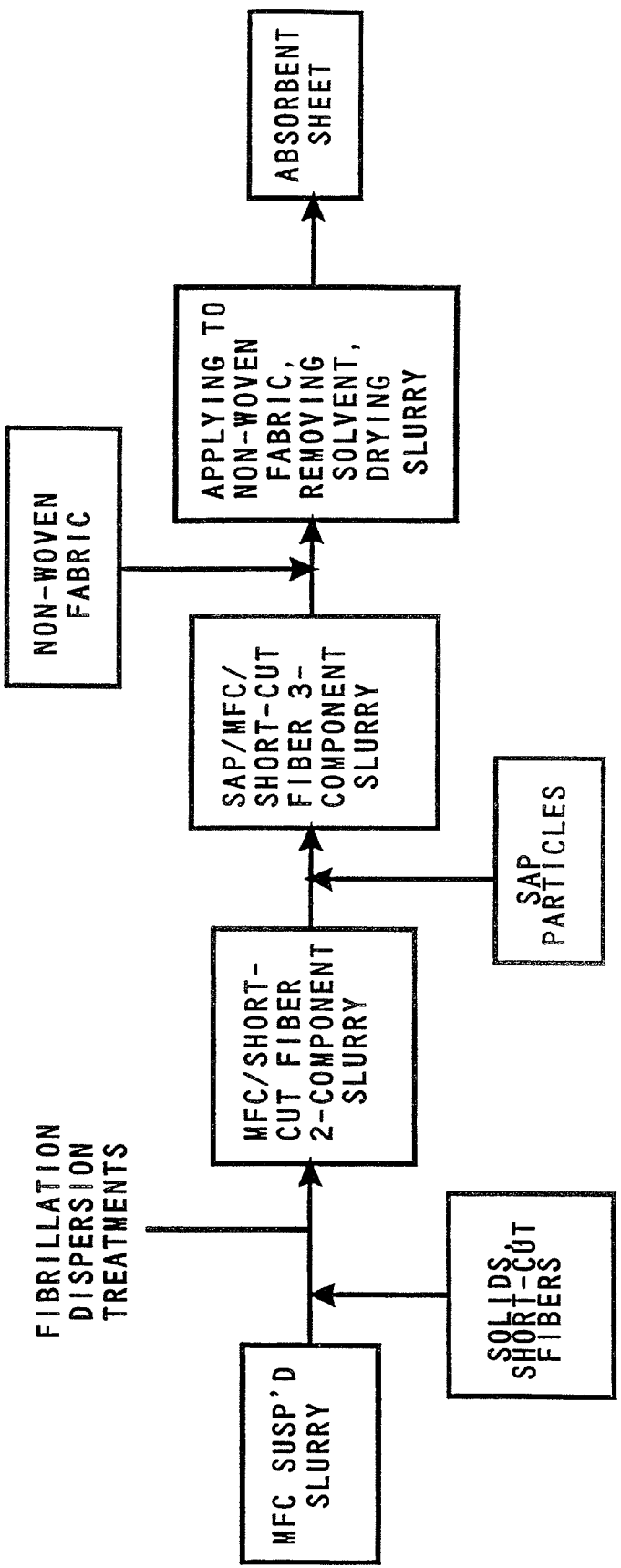
FIG. 48 is a block diagram showing an example of a process of adding a short-cut staple fiber component to the HFFM in the present invention.
Figure 49:
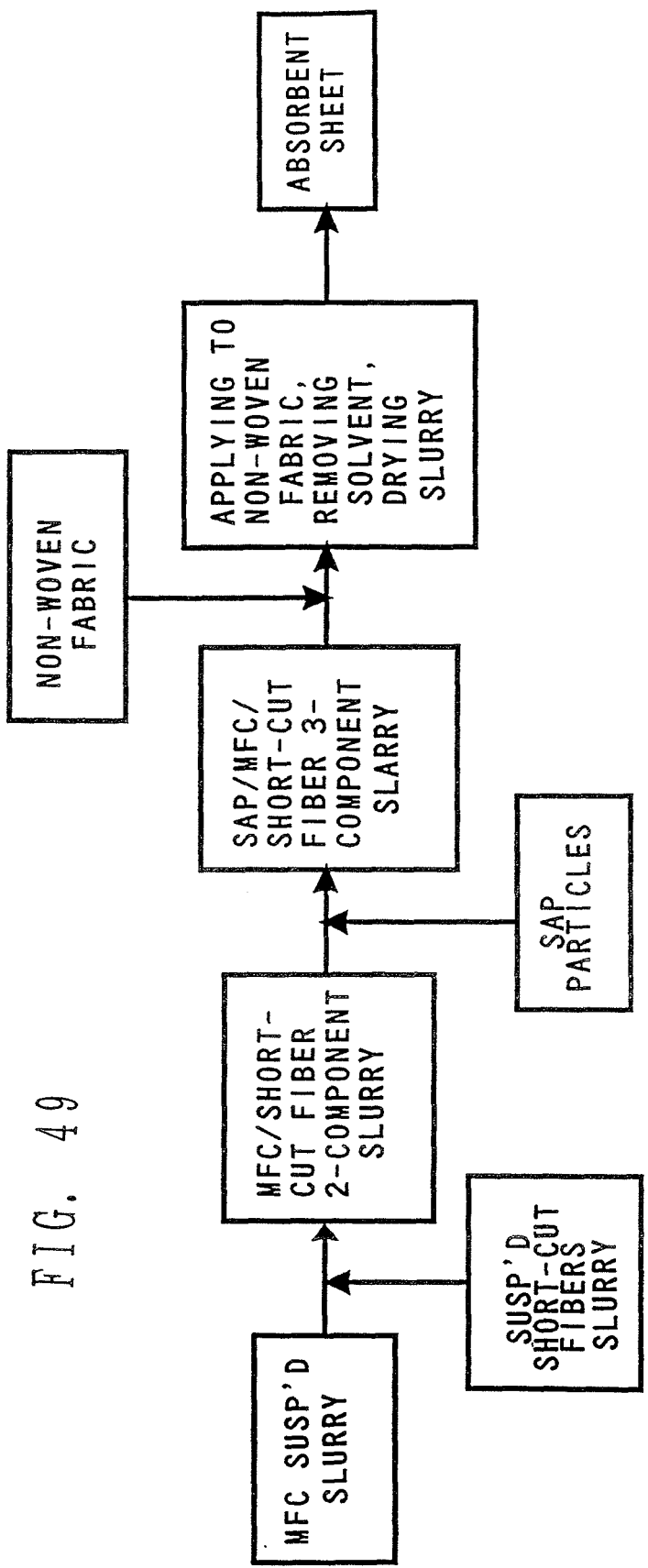
FIG. 49 is a block diagram showing an example of a process of adding a short-cut staple fiber component to the HFFM in the present invention.
Figure 50:
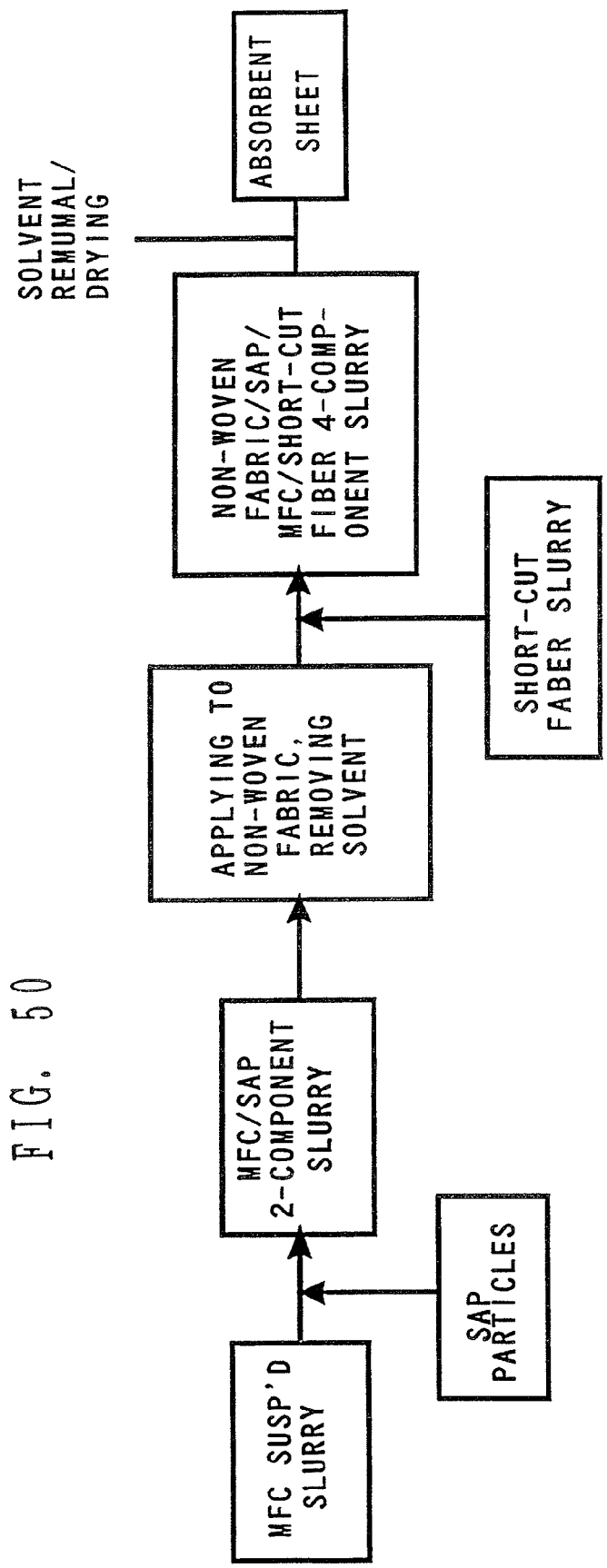
FIG. 50 is a block diagram showing an example of a process of adding a short-cut staple fiber component to the HFFM in the present invention.
Figure 51:
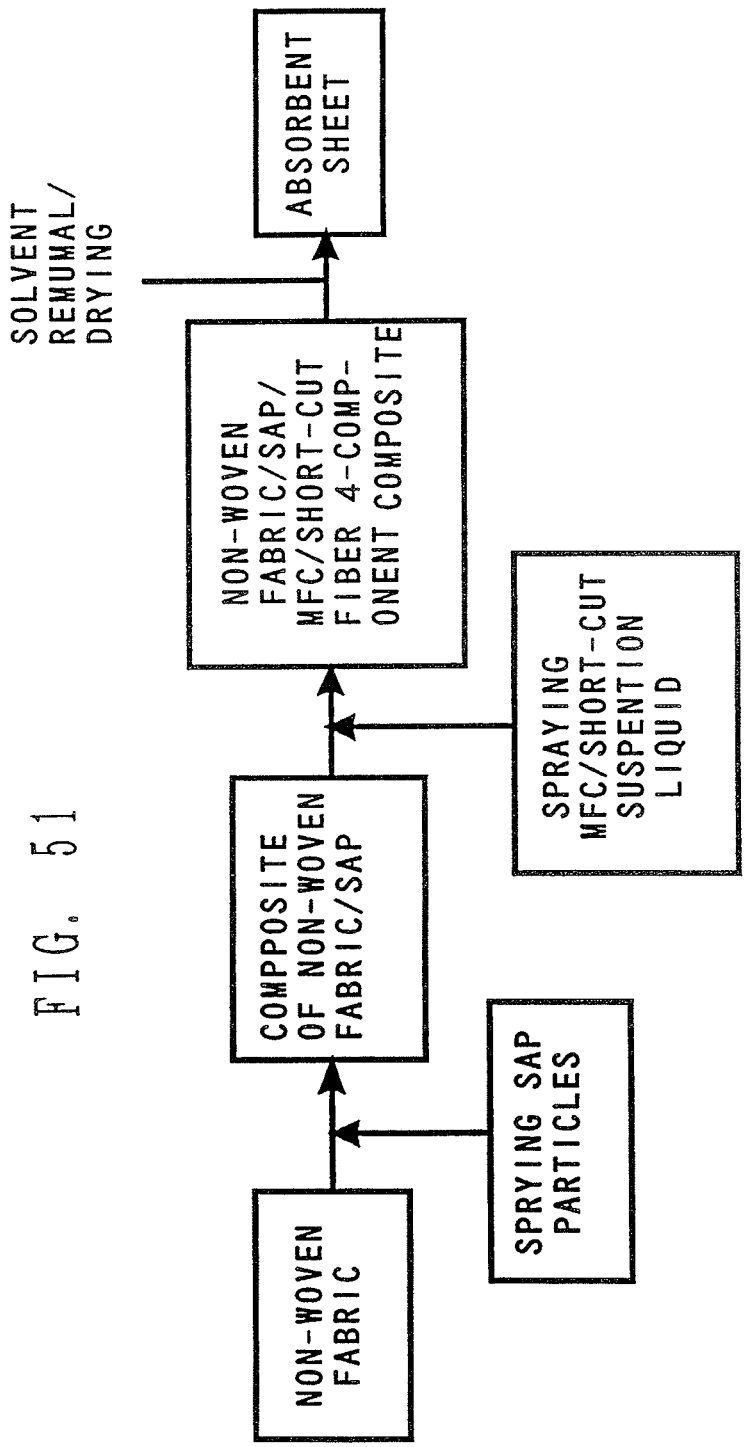
FIG. 51 is a block diagram showing an example of a process of adding a short-cut staple fiber component to the HFFM in the present invention.

Also, FIG. 47 shows an example where the absorbent material 725 is disposed in dots, not in bands or bars as shown in FIGS. 45 and 46.

In the structures shown in FIGS. 45 to 47, the liquid impervious sheet material 721 may have or have not openings in the bottoms of the dents 724.

In any case, the dents 724 formed on the liquid impervious sheet material may have an inner wall extending perpendicularly to the surface of the sheet material, but preferably, should have a funnel-like taper with the size becoming smaller from top to bottom which allows absorbent material to fill in more easily. The size of dents depends upon the size or shape of the absorbent material, but should be at least 0.3 mm, preferably 0.5 mm in the diameter if the dents are circular or, in the width of the shorter direction if the dents are long and narrow in the shape of ellipse, rectangle or groove. It is because if the diameter or width is too small, it is difficult to hold a sufficient amount of absorbent material stably in the dents.

Next, briefly, processes preferably applied in making the absorbent sheet of the present invention are described using the HFFM, the SAP and a short-cut staple fiber component. A process of adding the short-cut staple fiber component is selected, which is optimum depending upon the characteristic or property of the short-cut staple fiber component, namely in dry state or wet state, the necessity of fibrillation. FIGS. 48 to 51 show several examples of representative processes of making the absorbent sheet. From these flow charts the configuration of each process can easily be understood.

Figure 52:
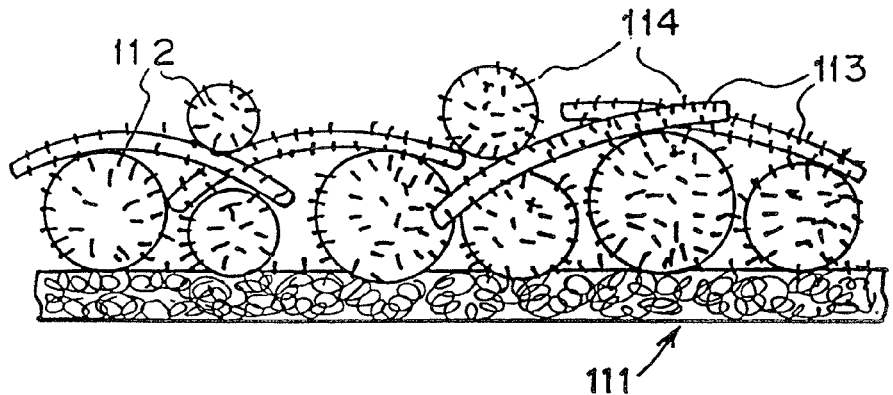
FIG. 52 is a fragmentary longitudinal sectional view showing an absorbent sheet of the present invention while it is in dry condition.
Figure 53:
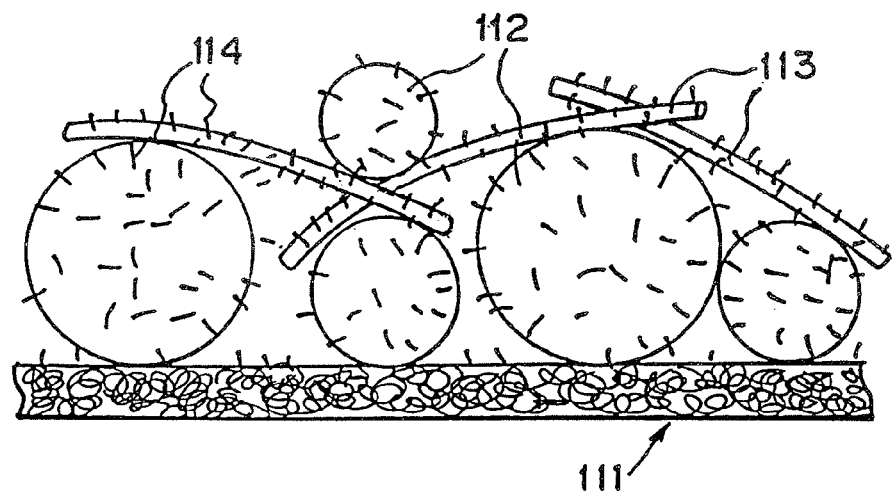
FIG. 53 is a fragmentary longitudinal sectional view showing the absorbent sheet shown in FIG. 52 while it is in wet condition.

First of all, typical model examples of the composite absorbent of the present invention composed of four components of the SAP, the MFC, short-cut staple fibers and a supporting sheet are shown in FIGS. 52 and 53. FIG. 52 shows the composite absorbent in a dry state, and FIG. 53 shows the composite absorbent of FIG. 52 which has absorbed a liquid and swollen. In FIGS. 52 and 53, reference numeral 111 represents a substrate, on the surface of which the SAP particles 112, a short-cut staple fiber component 113, and the HFFM 114 are held. As shown in FIG. 52, the SAP particles exist dispersed or with plural particles securely bonded by the MFC when they are in dry state, while groups of the SAP particles are contains with leeway as covered by the short-cut staple fiber component just like an umbrella.

When body exudates are discharged into the composite absorbent, the SAP absorbs them to swell. At that time the hydrogen bonds of the MFC are cutoff, and the SAP swells more freely but within the network where the SAP is contains so that the SAP is prevents from going out of the network.

Figure 54:
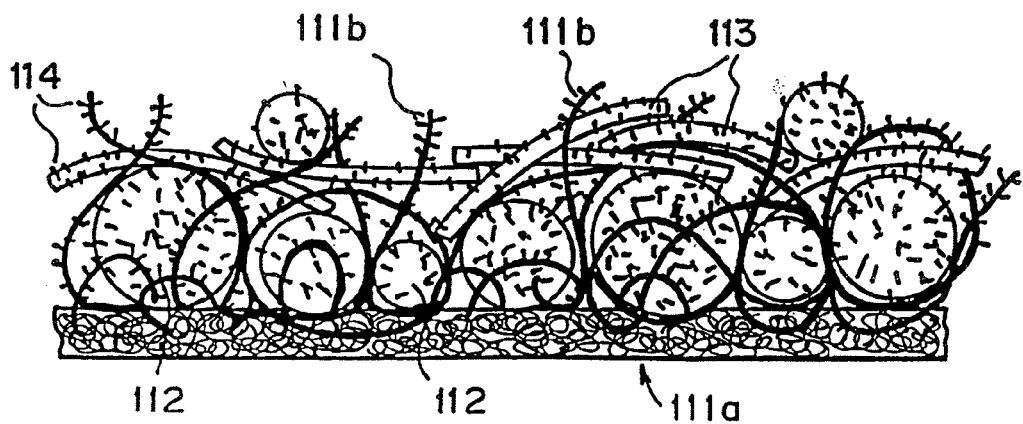
FIG. 54 is a fragmentary longitudinal sectional view showing other absorbent sheet of the present invention while it is in dry condition.

FIG. 54 is a structure where, by using a bulky substrate, the effects of the network are improved in concert with the effects of the short-cut staple fiber component. In FIG. 54, reference numeral 111*a* represents a high density layer of the substrate, 111*b* represents a low density layer of the substrate, 112 represents the SAP particles, 113 represents short-cut staple fibers, and 114 represents the HFFM. It is shown that the SAP particles are captured with relative leeway among the fibers of the low density layer of the substrate 111*b*. In the present invention, absorbent layer may be provided all over completely on either surface of the supporting sheet, but may also be provided in rows or any desired pattern. Also, by providing absorbent layer only on either surface of the supporting sheet, a composite absorbent having a sufficient absorbing capacity can be constituted, but in case the supporting sheet is used in such uses as a liquid contacts both sides of the supporting sheet, absorbent layer may be provided on both sides of the supporting sheet.

Methods of evaluating the properties applied in the present invention are described below:

1) Standing Sustainability of the Swollen SAP in a Composite Absorbent when Wetted Cut a Rectangle of 2 cm×10 cm from the Composite Absorbent to Make a Sample.

① Standing Sustainability of the SAP

Place two rectangular sample pieces with the SAP side upward at approximately 2 cm interval on a Petri dish of 12 cm diameter, add 50 ml of 0.9% NaCl (a physiological saline solution) gently and allow to stand for 10 minutes for the SAP to swell. Visually observe the condition where the SAP as swollen come off from the samples into the liquid.

(Judgement Criteria)

⊚ The SAP swells but little SAP is observed to come off.

○ As the SAP swells, a little SAP is observed to come off.

Δ As the SAP swells, the SAP is observed to come off appreciably.

X As the SAP swells, the SAP is observed to come off very much to pile up in the liquid.

② Standing Coming Off of the SAP

The procedure is the same including the judgment criteria as in the standing sustainability test, except that two sample pieces are placed with the SAP side downward.

③ Vertically Suspending Sustainability of the SAP

Take out the samples from the liquid with a pair of tweezers immediately after the evaluation in the above-described standing sustainability test, hold one end of the longitudinal direction with a clip to vertically suspend, and virtually judge the condition of the swollen SAP coming off from the supporting sheet.

(Judgement Criteria)

⊚ Little swollen SAP is observed to come off.

○ A little SAP as swollen on the surface is observed to come off.

Δ Of swollen SAP, a part of the SAP on the surface is observed to come off, but the SAP in direct contact with the supporting sheet is not observed to come off.

X A majority of swollen SAP is observed to come off.

2) Dispersion of an Absorbed Liquid by a Composite Absorbent

Cut a circle of 5 cm diameter from the composite absorbent to make a sample.

① Absorbing Time of Dropped Liquid (Seconds)

Place the sample on a Petri dish of 12 cm diameter with the SAP side upward, drop 1 ml of 0.9% NaCl (a physiological saline solution) with a burette in the center of the sample taking approximately one second, and measure the time (seconds) until the dropped liquid is absorbed.

②) Dispersing Time (Seconds)

Put 100 ml of 0.9% NaCl (a physiological saline solution) in a Petri dish of 12 cm diameter, float the sample with the SAP side upward with the side of the supporting sheet in contact with the liquid, and measure the time until the liquid disperses on the whole surface of the sample and the applied SAP finishes swelling on the whole surface.

3) Thickness of Supporting Sheet (mm)

Cut a circle of 5 cm diameter from the supporting sheet to make a sample. Measure using a thickness gauge of Daiei Chemical Precision Instruments Mgt. Co., Ltd. with the area of the probe of 15 cm$^2$ (43.7 mm diameter) and the measuring pressure of 3 g/cm$^2$.

4) Apparent Density of Supporting Sheet (g/cm$^3$)

Calculate from the weight (g/cm$^2$) and the thickness of the supporting sheet by the following formula:

Apparent density(g/cm$^3$)=[weight(g/m$^2$)/10$^4$]×[10/thickness(mm)]

Other composite absorbent sheet embodying the present invention are described where an absorbent sheet is provided with a liquid pervious supporting sheet and an absorbent layer containing the SAP particles bonded to either surface of the liquid pervious supporting sheet with the absorbent layer forming a plurality of high absorbing regions having higher absorbing capability than the other regions as distributed in a desired pattern on the surface of the liquid pervious supporting sheet.

Figure 55:
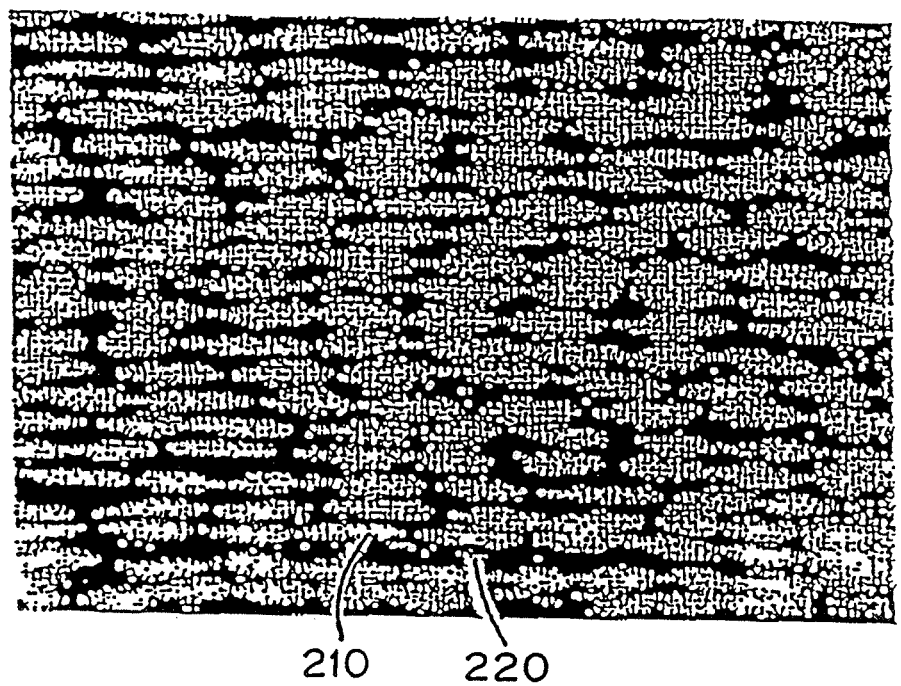
FIG. 55 is a plan view showing an example of an absorbent sheet of the present invention.

FIG. 55 typically shows a plurality of high absorbing regions having higher absorbing capability of the absorbent layer and low absorbing regions having lower absorbing capability on the supporting sheet embodying the present invention; on the drawing the white colored pans show high absorbing regions 210 and the black colored pans show low absorbing regions 220.

Figure 56:
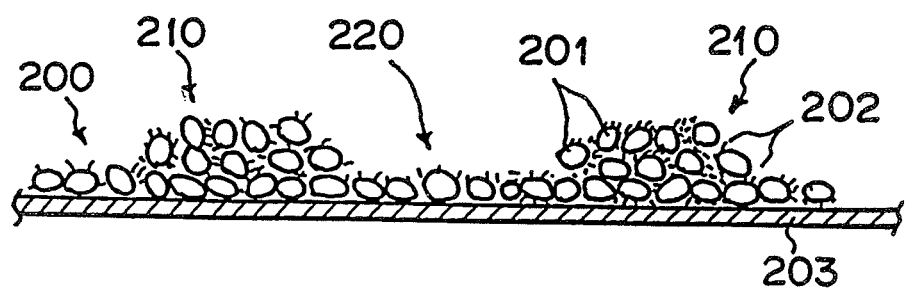
FIG. 56 is a fragmentary enlarged sectional view of the absorbent sheet of FIG. 55.

FIG. 56 is a longitudinal cross-sectional view of a part of the absorbent sheet shown in FIG. 55. Reference numeral 203 represents a supporting sheet made of material such as non-woven fabric having an appropriate liquid perviousness, and on either surface of this supporting sheet 203 absorbent layers 200 are provided forming regions of higher absorbing capability 210 and regions of lower absorbing capability 220.

The absorbent layers 200 are composed of the SAP particles 201 and the HFFM 202 existing around each particle 201, and the HFFM 202 bonds the SAP particles 201 together and is bonded to the surface of the supporting sheet 203 to function as a means of transferring a liquid to be absorbed to each particle.

In the examples shown in FIGS. 55 and 56, the difference in absorbing capability between the high absorbing region 210 and the low absorbing region 220 of the absorbent layer is realized by the difference in the thickness of the absorbent layer. This thickness is represented apparently by the configuration of the layer of the absorbent polymer, and as shown in FIG. 56, the thinner layer is in one layer, and the thicker layer is in two or more layers.

Figure 57:
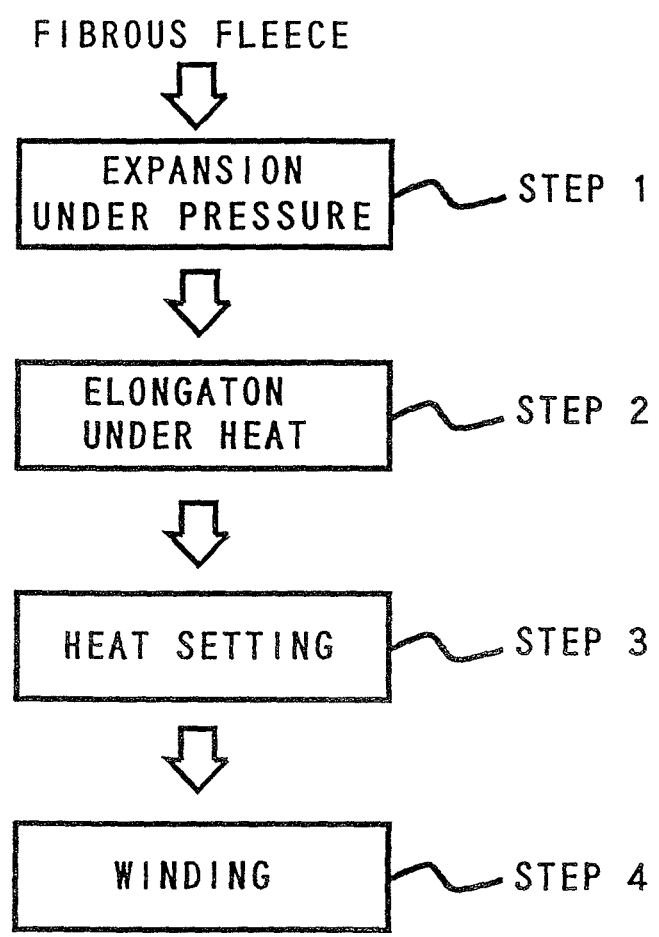
FIG. 57 is a flow chart showing an example of a process of making a supporting sheet to be used in the present invention.
Figure 58:
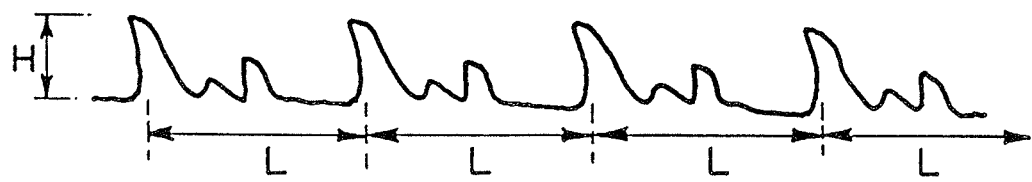
FIG. 58 is an explanatory drawing showing the sectional view of the supporting sheet made by the process of FIG. 57.

An example of non-woven fabric having preferable properties as material of the absorbent sheet of the present invention is, as previously proposed in Japanese Patent Examined Publication No. HEI 9-59862 of the present applicant, non-woven fabric where spun bond having a bi-component structure is used, stretched and heat set by a method shown in FIG. 57 to provide a cross-sectional structure as shown in FIG. 58. This non-woven fabric has a property of being more likely to elongate much only in one direction. In FIG. 58, the preferable range of H is 0.2 mm to 2 mm, and the preferable range of L is 1 mm to 5 mm.

Figure 59:
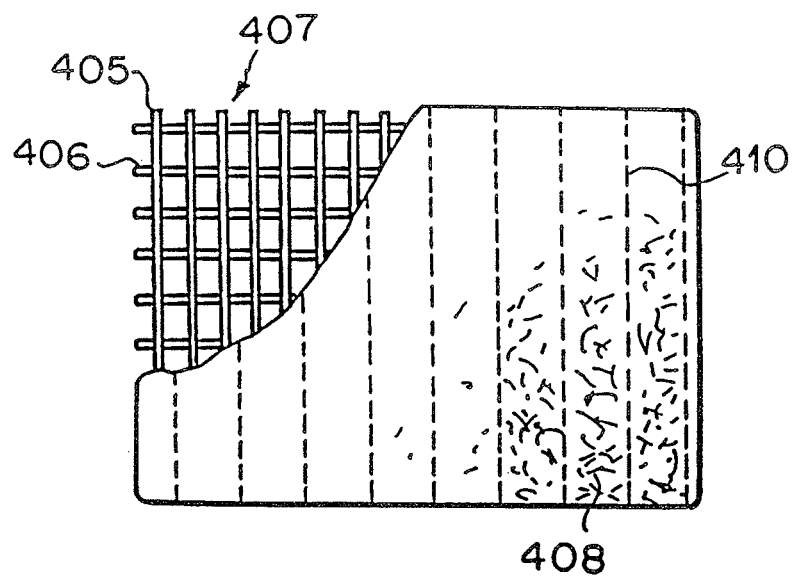
FIG. 59 is a fragmentary hatched plan view showing an example of a supporting sheet suitable
Figure 60:
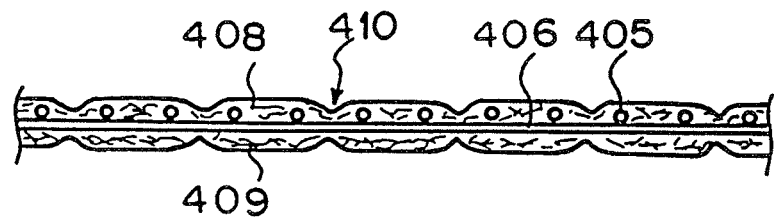
FIG. 60 is a fragmentary enlarged sectional view of FIG. 59.

Another example of non-woven fabric is, as previously proposed by the present applicant in his Japanese Patent Application No HEI 8-345410, non-woven fabric where a highly elastic net and a fiber web are partially laminated. This laminated non-woven fabric has a structure, as shown in FIGS. 59 and 60, where on both surfaces of a net 407 where longitudinal elastic string 405 and lateral elastic string 406 are intersected with each other and bonded at points of intersection, identical or different webs 408 and 409 are laminated, and the net and the web are bonded along bonding lines 410 arranged in parallel to each other so that the laminated non-woven fabric has a property of being likely to elongate much only in one direction perpendicular to the bonding lines 410.

The SAP can be beforehand carried by a supporting member previously formed in the shape of a sheet, but can also be introduced into a supporting sheet when the supporting sheet is manufactured by practising the present invention. An absorbent composite can be obtained, for example, by making a carded web of easy-to-melt synthetic staple fiber and fibrous SAP, by, after laminating a pulp, the SAP and easy-smelt staple fibers by an air-laid method, heat treating to fix the laminated composite, or by, after impregnating a non-woven web with acrylic acid monomer, polymerizing and cross-linking such impregnated non-woven web. The surface of the carried SAP may be exposed or may be covered by tissue or the like.

Figure 61:
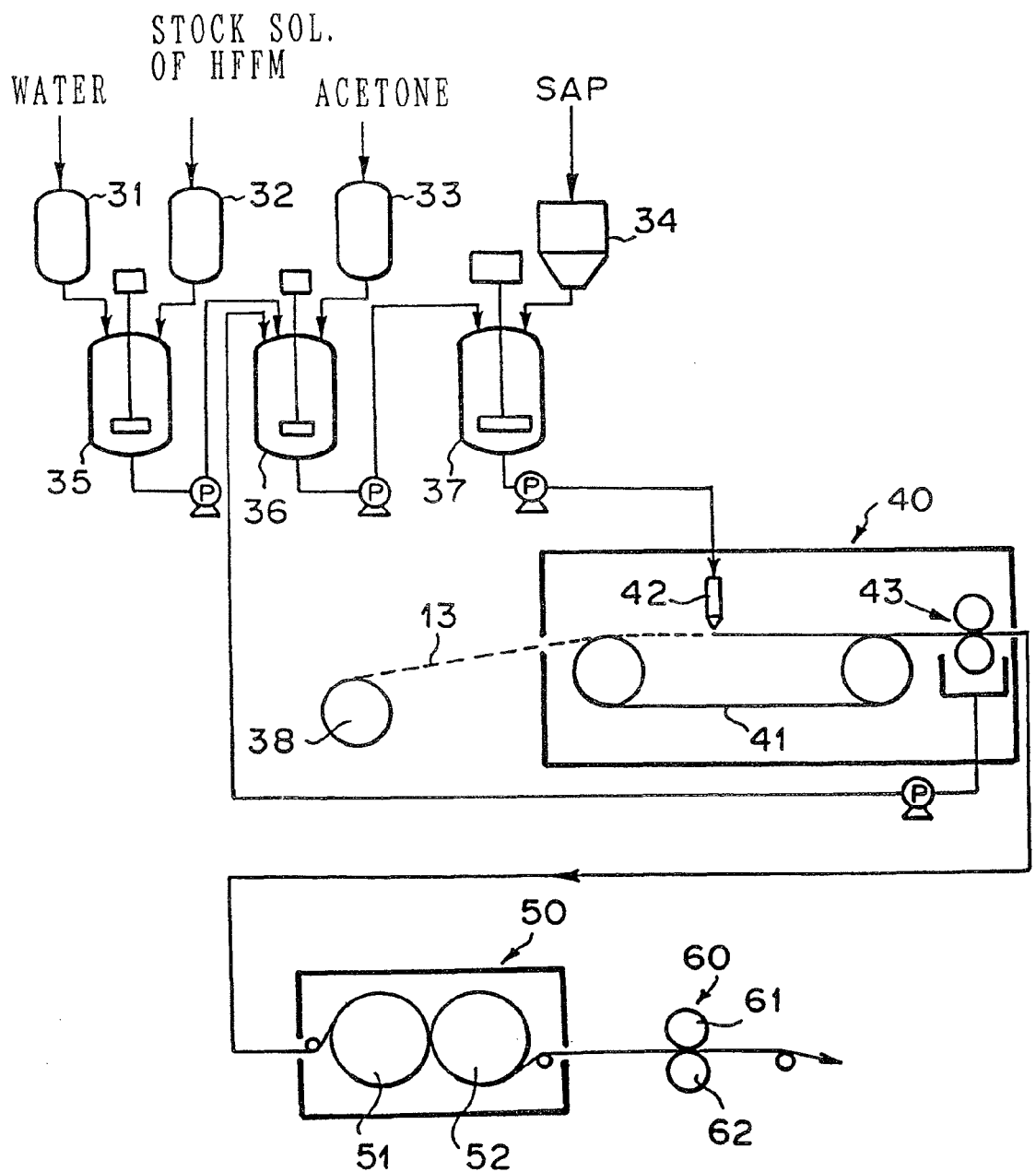
FIG. 61 is a schematic longitudinal sectional view of an apparatus for making a composite sheet material according to the present invention.

Next, with reference to the accompanying drawings, an apparatus suitable for making the absorbent composite of the present invention is described below:

In FIG. 61, reference numeral 31 represents a tank for storing ion-exchanged water, 32 represents a tank for storing the HFFM stock solution, 33 represents a tank for storing acetone, and 34 represents a tank for storing the SAP. The HFFM water dispersed stock solution taken from the tank 32 is introduced into a mixing unit 35 provided with a stirrer, diluted in the mixing unit 35 with water taken from the tank 31, and, then, pumped into a second mixing unit provided with a stirrer. Into the mixing unit 36, acetone taken from the tank 33 is introduced, and this mixture is pumped into a third mixing unit 37 provided with a stirrer. Into the mixing unit 37 the SAP particles are introduced from the tank 34, and in this mixing unit the HFFM, the organic solvent, water and the SAP are mixed to form their mixture.

On the other hand, an appropriate supporting sheet 13 of such material as non-woven fabric is unrolled from a roll 38 and then introduced to a forming area 40. The forming area is provided with a belt conveyor 41 and a nozzle 42 located disposed over the belt of the belt conveyor. The mixed dispersion liquid from the mixing unit 37 is pumped to this nozzle 42. While the supporting sheet 13 is being conveyed by the belt conveyor 41 at a prescribed speed, the mixture dispersion liquid is sprayed from the nozzle 42 onto the supporting sheet 13. The nozzle 42 may be of various configurations depending upon the pattern of absorbent composite layers formed on the supporting sheet 13.

The forming area 40 is further provided with a roll press 43 composed of a pair of rollers. The supporting sheet coated with the mixture dispersion liquid is pressed by the roll press 43 so that the solvent contained in the dispersion medium is squeezed and the solvent as separated is pumped to the second mixing unit 36.

The supporting sheet 13 after coming out of the forming area is sent to a drying area 50. To the drying area 50 hot air is supplied in which area a pair of porous rolls 51 and 52 are provided. The supporting sheet 13 and the mixture dispersion liquid sprayed on the sheet are dried while they are being conveyed along the peripheries of the porous rolls 51 and 52.

The supporting sheet after coming out of the drying area is compressed in a compressing area 60 consisting of a pair of press rolls 61 and 62, and thus, a product where absorbent composite layers are formed on the supporting sheet 13 is obtained.

Figure 62:
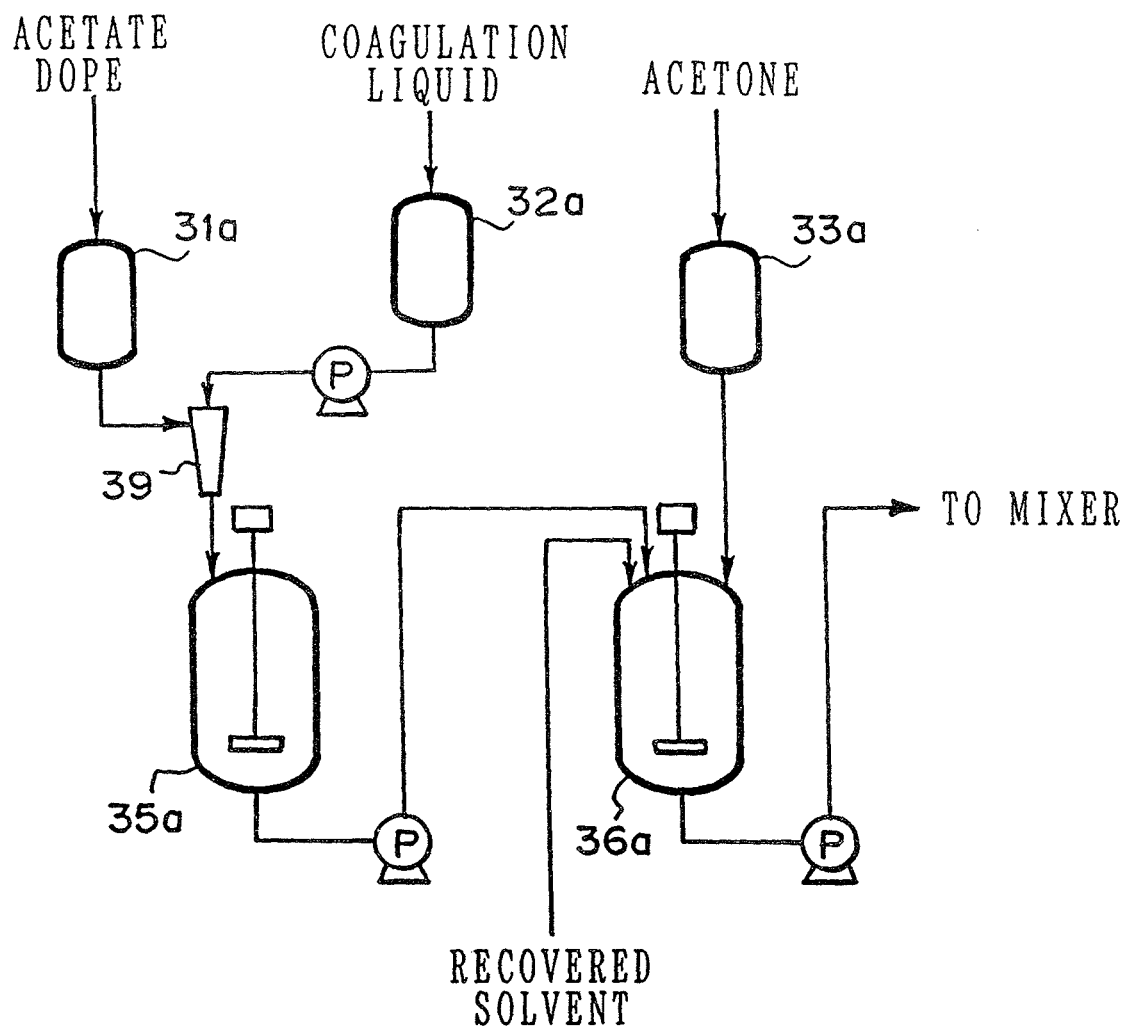
FIG. 62 is a schematic longitudinal sectional view showing a modified example of the apparatus of FIG. 61.

FIG. 62 shows a system wherein an apparatus for making the HFFM from acetyl cellulose is combined with the apparatus shown in FIG. 61. In this system acetate dope is stored in a tank 31a, a coagulation liquid is stored in a tank 32a, and acetone is stored in a tank 33a. The acetate dope and the coagulation liquid from the tanks 31a and 32a are sent to an aspirator type fibrillating unit, where fibrillation is carried out. The fibrils are refined in a mixing unit 35a to obtain finer fibrils, namely the HFFM in slurry. The HFFM are then mixed in a second mixing unit 36a with acetone from the tank 33a, and again mixed with the SAP in another mixing unit (not shown). The subsequent steps are the same as those of the process of FIG. 61.

Figure 63:
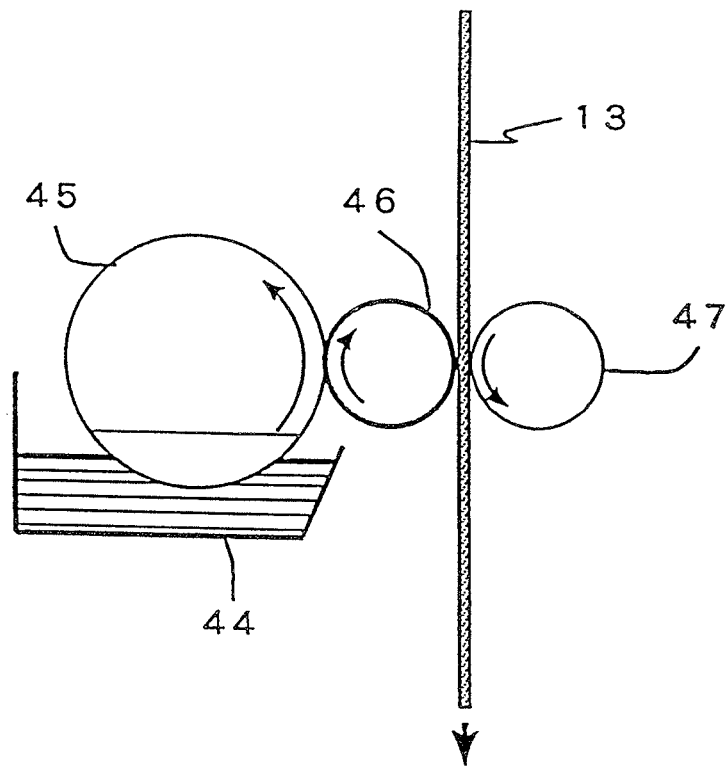
FIG. 63 is a schematic longitudinal sectional view showing another coating apparatus to be used in the apparatus shown in FIG. 61.
Figure 64:
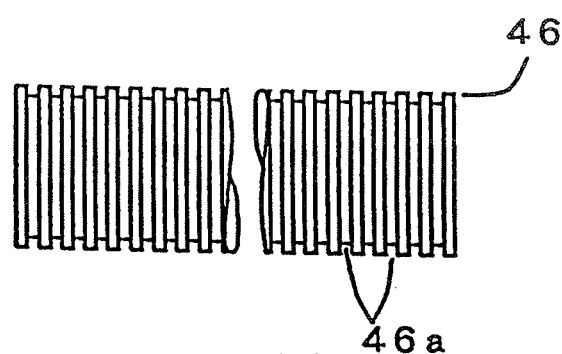
FIG. 64 is a plan view of a grooved roll used in the apparatus of FIG. 63.
Figure 65:
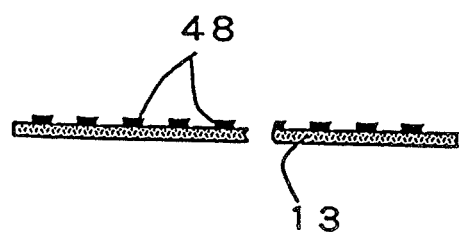
FIG. 65 is a cross sectional view of a supporting sheet which is coated with a dispersion liquid by the apparatus shown in FIG. 63 and FIG. 64.

FIG. 63 shows an example of another apparatus for applying a mixture dispersion liquid onto the supporting sheet 13 in the forming area 40 of FIG. 61. In FIG. 63, reference numeral 44 represents a top-opened tank for storing a mixture dispersion liquid, and in the tank 44 a dipping roll 45 is disposed which is rotatable with a horizontal shaft in the center with a part of the periphery being dipped in the mixture dispersion liquid. Also, a pair of rolls 46 and 47 are provided which are rotatable with a shaft in the center in parallel, respectively, to the dipping rolls 45. The roll 46 is contacted with the periphery of the dipping roll 45 with pressure, and, as, for example, shown in FIG. 64, has many ring shaped grooves on the periphery. Through the nip between the roll 46 and the other roll 47 which has a flat surface, the supporting sheet which is to be coated with the mixture dispersion liquid is made to pass. The mixture dispersion liquid stored in the tank 44 deposits by its own viscosity on the periphery of the dipping roll 45 rotating in the tank, and is transferred onto the supporting sheet via. the groove roll 46. Thus, as shown in FIG. 65, mixture dispersion liquid layers 48 in many bands arranged in parallel to each other are formed on the surface of the supporting sheet. The grooved pattern formed on the roll 46 can be freely designed, and the mixture dispersion liquid can be applied onto the supporting sheet in a pattern corresponding to the pattern on the roll 46.

The features and properties of an absorbent product in which the highly absorbent composite is incorporated are described briefly below:

When the highly absorbent composite is used in an absorbent product, firstly, the product is extremely thin and compact before worn and while worn before it absorbs a liquid, so that the SAP particles are held securely and stably and therefore, if it is folded or bent, the SAP particles do not move or come off. The structure of the product does not break down.

Secondly, when a liquid is absorbed by the absorbent product, although it is of a structure of pulpless with 90% or more of the SAP, the product absorbs the liquid very quickly without blocking thanks to the hydrophilicity and physical forms of the HFFM.

Thirdly, after a liquid is absorbed, swollen polymer particles are held still securely by the network of the HFFM and are thus prevented from coming off.

The fourth feature of the absorbent product relates to a characteristic when it is disposed of. The absorbent of the present invention when it is in contact with excessive water remains stable as it is, but, if shearing force is applied, it immediately is dissociated. The absorbent is suitable for making a flushable. In addition, since the cellulosic HFFM is extremely high in cellulase enzyme activity, the structure of such HFFM if buried in the land is dissociated in a short period of time. Further, if any biodegradable aminoacetic type absorbent polymer or the like is combined to make the SAP, an ideal nature-friendly absorbent can be designed.

The configuration of an example of an apparatus for making the absorbent sheet as shown in FIGS. 55 and 56 is described with reference to FIG. 66 below. In FIG. 66, reference numeral 311 represents a slurry supplying pipe by means of which a slurry dispersion liquid containing the HFFM and the SAP is supplied, and to the slurry supplying pipe 311 a plurality of pipes 313 each on the top end of which a nozzle 312 is provided is connected. Each pipe 313 is provided with a pump 314 as a transferring means of sucking the slurry dispersion liquid from the slurry supplying pipe 311 and discharging the liquid from the nozzle 312. The pump is driven by a motor 315 which is used in common.

On the other hand, it is so designed that the liquid pervious supporting sheet 203 which is to be coated with the slurry dispersion liquid discharged from the nozzle 312 is conveyed at a constant speed in a direction indicated by an arrow in the drawing. Each pump 314 is capable of supplying the slurry dispersion liquid at a periodically varying pressure to the nozzle 312, and as a result, on the liquid pervious supporting sheet 203, bands 316 of slurry dispersion liquid of a number corresponding to the number of the nozzles 312 are formed and each band 316 can be made different in the thickness of the absorbent layer and has a indefinite margin.

A means of forming a distribution of patterns is that, at the step of coating the surface of the liquid pervious supporting sheet with the dispersion liquid supplied in a constant flow, a nozzle is used having a structure or function of imparting an appropriate pattern to the thickness and/or width of the coated layers.

Figure 68:
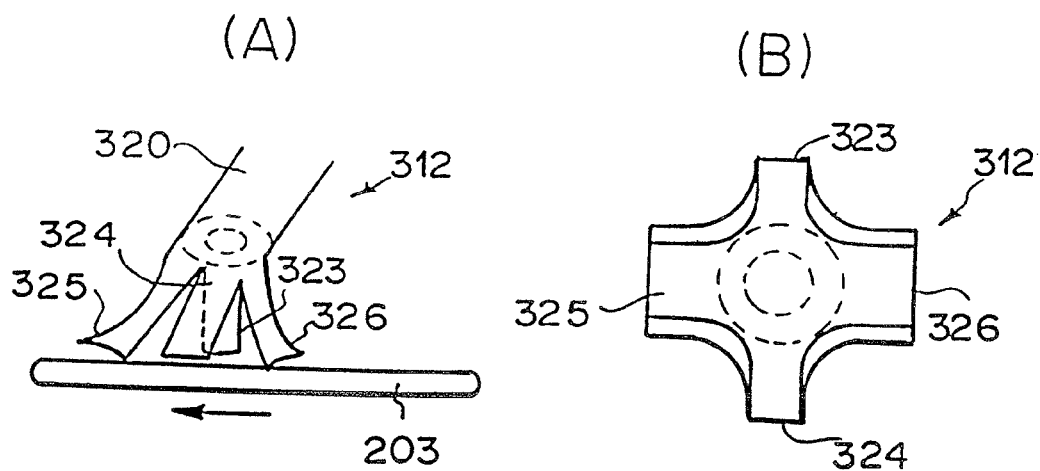
FIG. 68 shows another example of a nozzle for discharging a slurry dispersion liquid to be applied in the apparatus of FIG. 66: (A) is a side view thereof and (B) is a bottom view thereof.

A nozzle of this function may be ones shown in FIGS. 67 and 68. The nozzle 312 shown in FIG. 67 has a structure that two slits having a prescribed length each are formed from the tip portion of the tube shaped body 320 and the tip portion is divided into two tips 321 and 322, and, as a result, a discharging outlet is formed on each of the tips 321 and 322.

In addition, the nozzle 312 shown in FIG. 68 has a structure that four slits having a prescribed length each are formed from the tip portion of the tube shaped body 320 and the tip portion is thus divided into four portions 323 to 326. In this case, on each tip of the four portions 323 to 326 a discharging outlet is formed.

Figure 69:
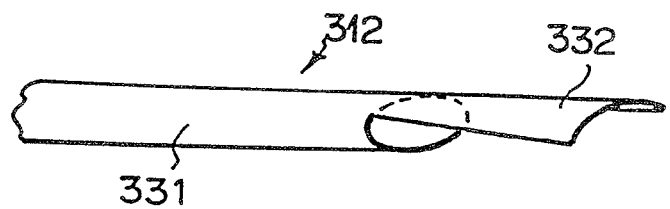
FIG. 69 is a perspective view showing an example of a nozzle for discharging a slurry dispersion liquid to be used for making an absorbent sheet of the present invention.
Figure 70:
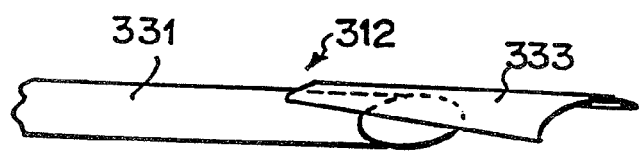
FIG. 70 is a perspective view showing an example of a nozzle for discharging a slurry dispersion liquid to be used for making an absorbent sheet of the present invention.
Figure 71:
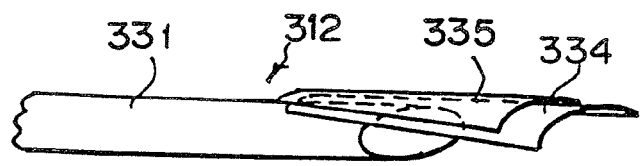
FIG. 71 is a perspective view showing an example of a nozzle for discharging a slurry dispersion liquid to be used for making an absorbent sheet of the present invention.

Examples of other structures of the nozzle are shown in FIGS. 69 to 71. The nozzle 312 of FIG. 69 has a structure in which on the tip of the tube 331 having rigidity or some flexibility a tongue portion 332 is formed in an integrated way. Also, the nozzle 312 of FIG. 70 has a structure in which on the tip of the tube 331 a separately prepared tongue portion having rigidity or some flexibility is mounted. Further, the nozzle 312 of FIG. 71 has a structure in which on the tip of the tube 331 a separately prepared flexible tongue portion 334 and a reinforcing member 335 on the outside of the tongue portion are mounted.

In the cases of the nozzles shown in FIGS. 69 to 71, a discharging outlet on the opening on the tip of the body 331 and a discharging outlet on the tip of each tongue portion 332 to 334 are formed so that each nozzle is provided with a plurality of discharging outlets.

Figure 72:
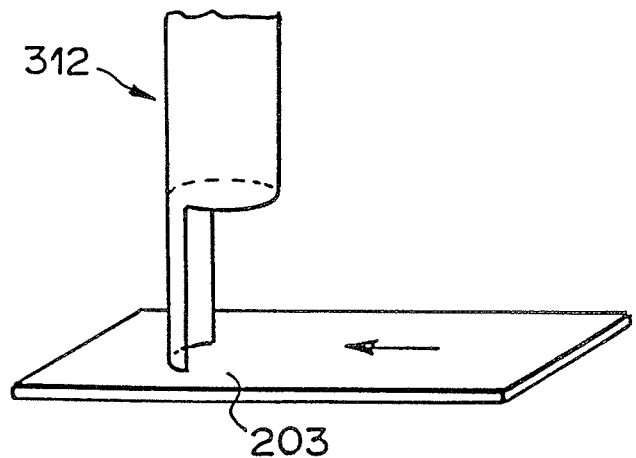
FIG. 72 is an explanatory drawing showing an example of the condition where a nozzle contacts a liquid pervious supporting sheet.
Figure 73:
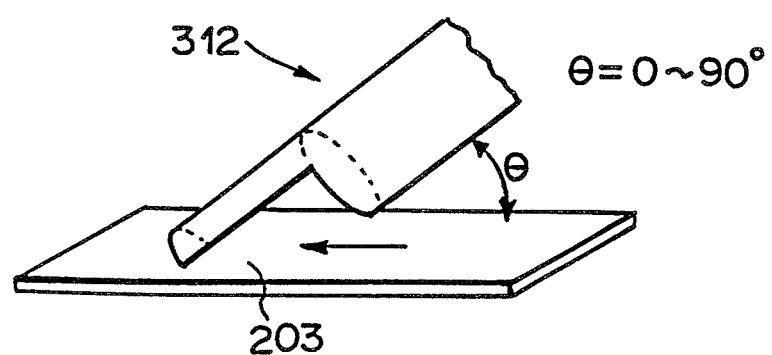
FIG. 73 is an explanatory drawing showing another example of the condition where a nozzle contacts a liquid pervious supporting sheet.

These nozzles 312 are disposed at right angles to the liquid pervious supporting sheet 203 to be coated with the slurry dispersion liquid as shown in FIG. 72 or inclined by some degrees q to the liquid pervious supporting sheet to be coated with the slurry dispersion liquid as shown in FIG. 73. When the slurry dispersion liquid is discharged from the nozzle of this disposition, the dispersion liquid is discharged in a direction of lower resistance depending upon the discharging pressure so that coating is conducted in a pattern having indefinite margins.

The reason why the above-described operation is conducted with relative ease is because the slurry containing the SAP and the HFFM has a structural viscosity (thixotropic flow). The property of the slurry may be contributing to the easy operation of the coating that the slurry is discharged from the nozzle keeping a high liquidity while it has a discharging flow velocity, but after discharged it loses the liquidity and solidifies.

As a result of this, a plurality of high absorbing regions in bands varied in thickness and having indefinite margins are formed on the surface of the liquid pervious supporting sheet.

Another means of forming a distributed pattern of absorbent layers on the supporting sheet is to give pulsation effects by incorporating a pulsation generating area in either of or both of the nozzle portion including a header and the feeding mechanism of the supporting sheet. By this means absorbent layers which are periodically varied in thickness and width can be formed. In the above, the methods of utilizing the pulsation of a pump, utilizing a special type of a nozzle, and vibrating an apparatus to give pulsating effects to the dispersion slurry as the means of forming a distribution of patterns are described. To be combined with either of the methods there is a means of making such SAP as is different in particle size or shape or gives a large difference in absorbing speed co-exist in the dispersion slurry. In this case, with the uniform dispersion and the stable discharging from the nozzle taken into consideration, it is preferable to disperse such SAP as is of larger particle size or of different shape in a dispersion system of such SAP as is of relatively fine particle size.

Now, the purpose of forming a distribution of patterns like this is that while, having different distributions of concentrations (higher and lower concentrations), of densities (higher and lower densities), and of thickness (thicker and thinner) and at the same time increasing the surface area of lower concentration portions, rapid absorbing and diffusion are obtained by utilizing lower concentration portions or non-absorbing portions and time requiring but stable absorbing is realized by utilizing thicker concentration portions so that an absorbent suitable for absorbing as many times as possible utilizing a structure of as many phases as possible can be designed. On the other hand, by imparting this structure sufficient flexibility can be imparted to the whole of an absorbent sheet to fit well the body of a wearer. In other words the portion which is coated thick with absorbent layer has rigidity and is hard to be bent while the portion which is little or not coated with absorbent layer is very easy to be bent with the property of the supporting sheet itself maintained.

Figure 74:
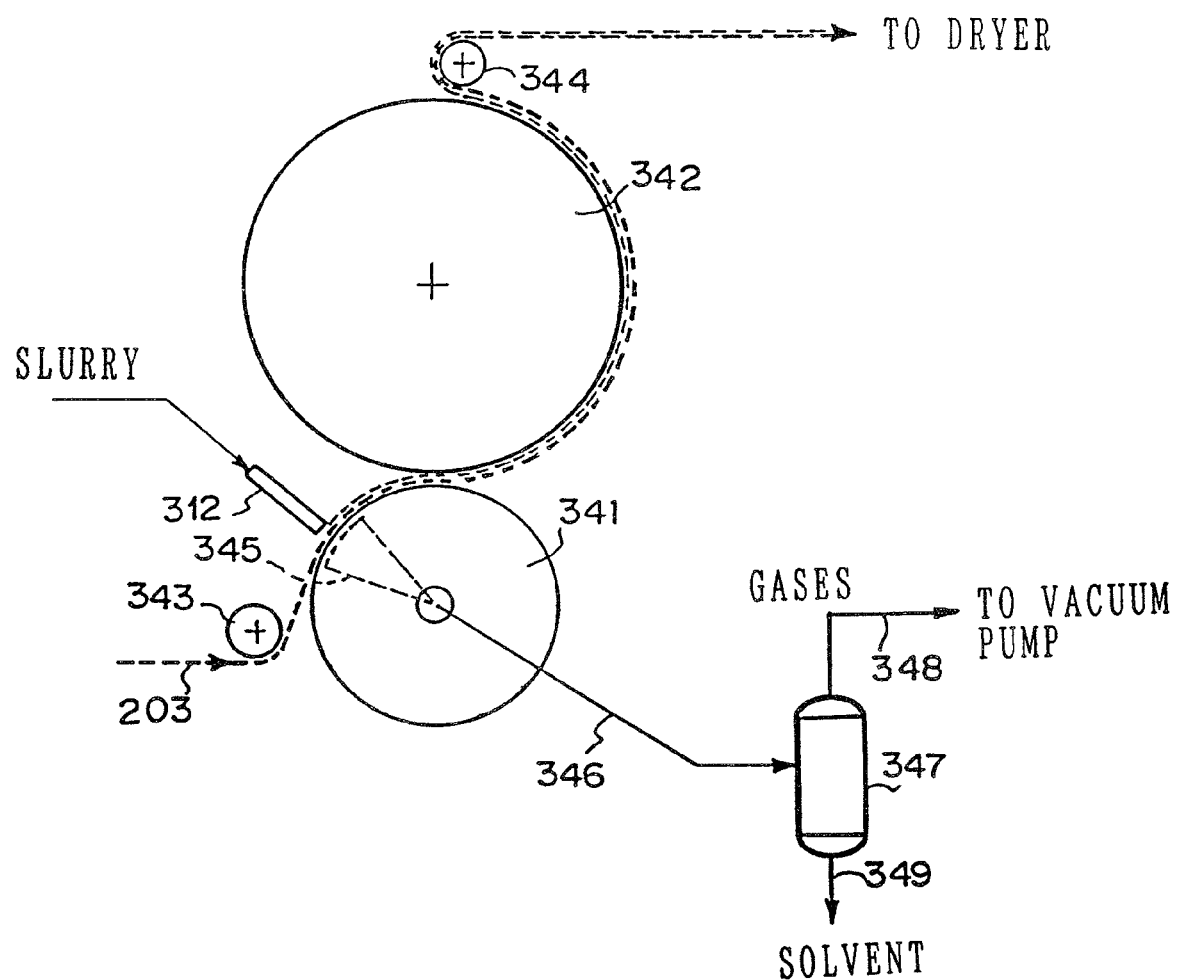
FIG. 74 is a schematic flow diagram showing an apparatus for making an absorbent sheet of the present invention.
Figure 75:
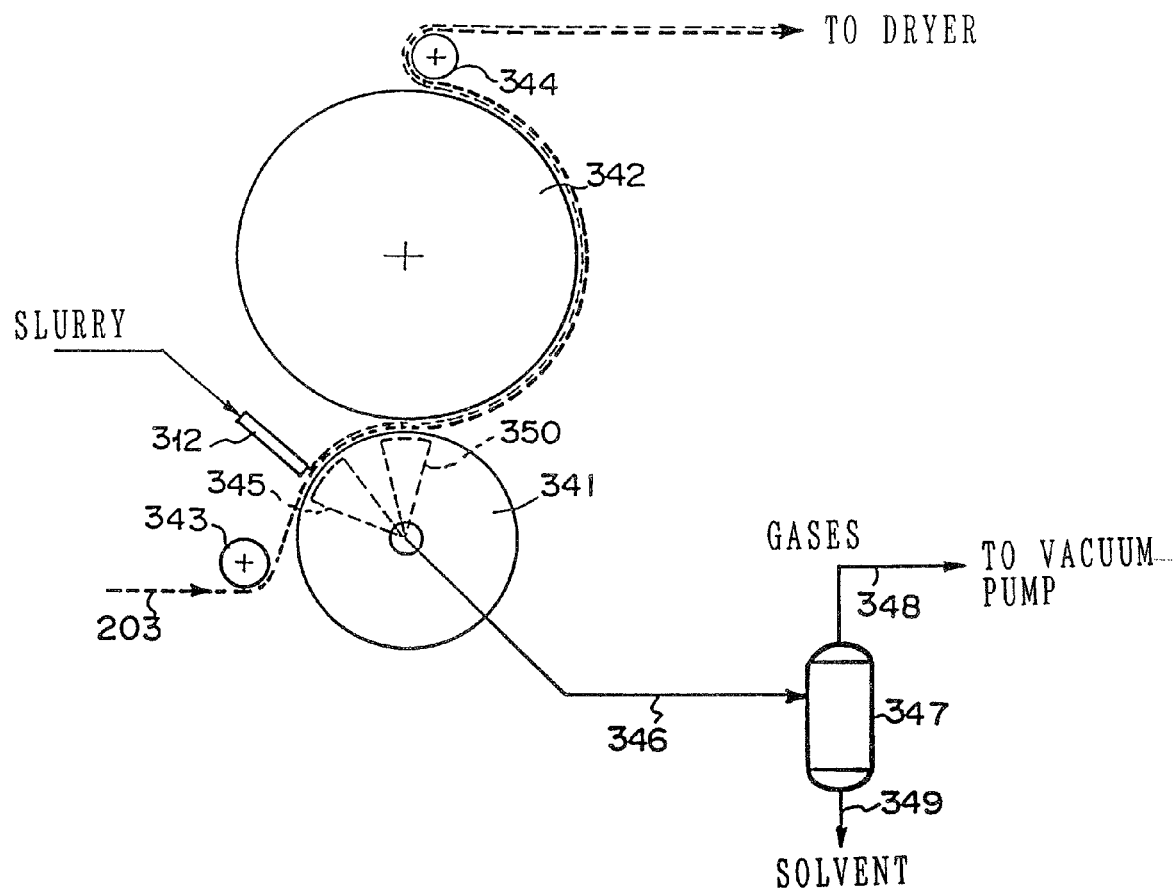
FIG. 75 is a schematic flow diagram showing another apparatus for making an absorbent sheet of the present invention.

This method is extremely effective from the commercial viewpoint. FIGS. 74 and 75 show examples a process of making an absorbent sheet having a plurality of high absorbing regions having high absorbing capability distributed in a pattern according to the present invention.

A coating apparatus shown in FIG. 74 is composed as follows: a suction roll 341 and a heat press roll 342 supported with a shaft and arranged in parallel to each other are provided and a liquid pervious supporting sheet 203 is guided via guide roll 343 to the suction roll 341 and at the position where the liquid pervious supporting sheet 203 is rotated approximately one fourth of the periphery of the suction roll 341, the liquid pervious supporting sheet 203 comes in contact with the heat press roll 342, and then while in contact with the heat-press roll 342 the liquid pervious supporting sheet 203 is rotated approximately one half of the periphery of the heat press roll 342, and finally is guided via a guide roll 344 to a dryer (not shown).

A suction area 345 is provided in the suction roll 341, which area forms a region for sucking the liquid pervious supporting sheet 203 conveyed in contact with the periphery of the suction roll 341. A nozzle 312 is disposed at a position where the nozzle 312 can discharge a slurry dispersion liquid onto the surface of the liquid pervious supporting sheet 203 in this suction area, and forms layers in a desired pattern on the liquid pervious supporting sheet 203. Reduced pressure generated in the suction area makes the slurry dispersion liquid adhere to the surface of the liquid pervious supporting sheet 203 and at the same time sucks an excess of the solvent contained in the slurry dispersion liquid together with surrounding air. The sucked liquid is guided via a pipe 346 to a strainer 347 where the liquid is separated into solvent and gas. The solvent thus separated is taken out via a pipe 349 for recycle to form a slurry dispersion liquid, and the gas is discharged outside from a pipe 348 via a vacuum pump (not shown).

The liquid pervious supporting sheet 203 is then conveyed while in contact with the heat press roll 342, in the process of which slurry dispersion liquid as heated is adhered to the liquid pervious supporting sheet 203, and the obtained absorbent sheet is then guided via the guide roll 344 to the dryer where the absorbent sheet is dried finally.

A coating apparatus shown in FIG. 75 is only different from the coating apparatus of FIG. 74 in that in addition to the suction area 345 disposed facing the nozzle 312, a second suction area 350 is provided as disposed in the nip with a heat press roll 342. In the second suction area 350, the solvent is further strongly sucked and separated from the slurry dispersion liquid while the slurry dispersion liquid is pressed between a suction roll 341 and a heat press roll 342.

Figure 76:
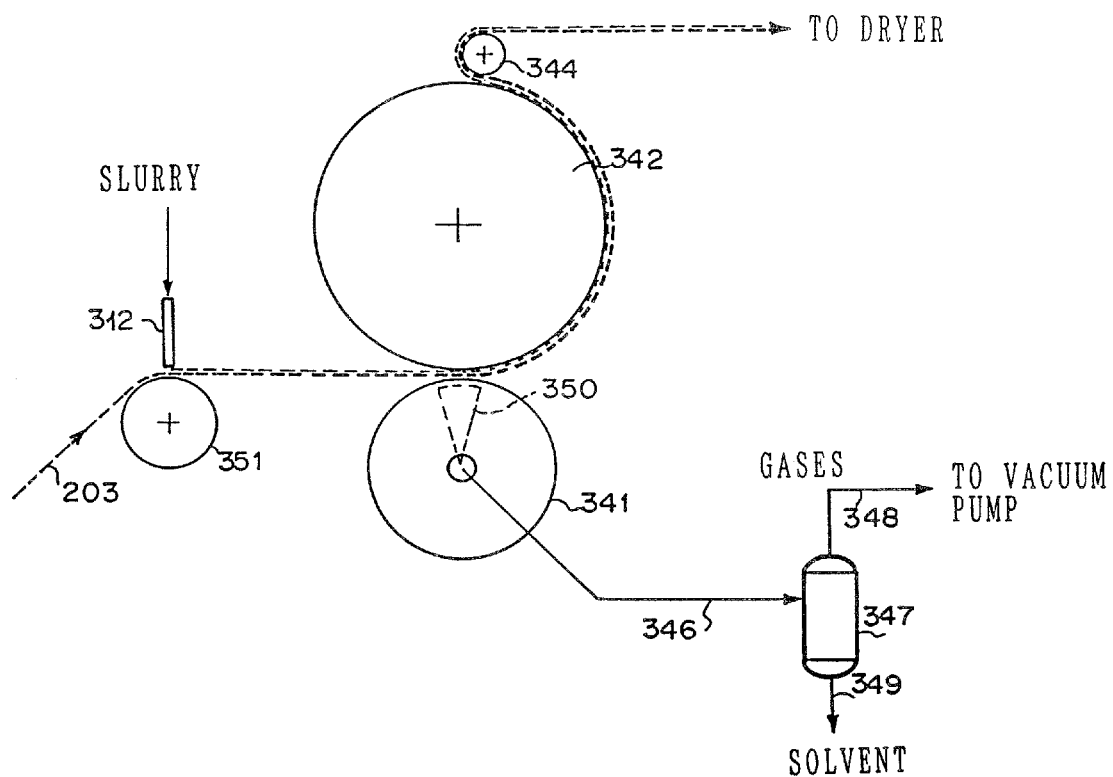
FIG. 76 is a schematic flow diagram showing other apparatus for making an absorbent sheet of the present invention.

A coating apparatus shown in FIG. 76 is different only in that a nozzle 312 is designed to apply a slurry dispersion liquid not over a suction roll 341 but on the periphery of a supporting roll 351 provided before the suction roll 341.

Figure 90:
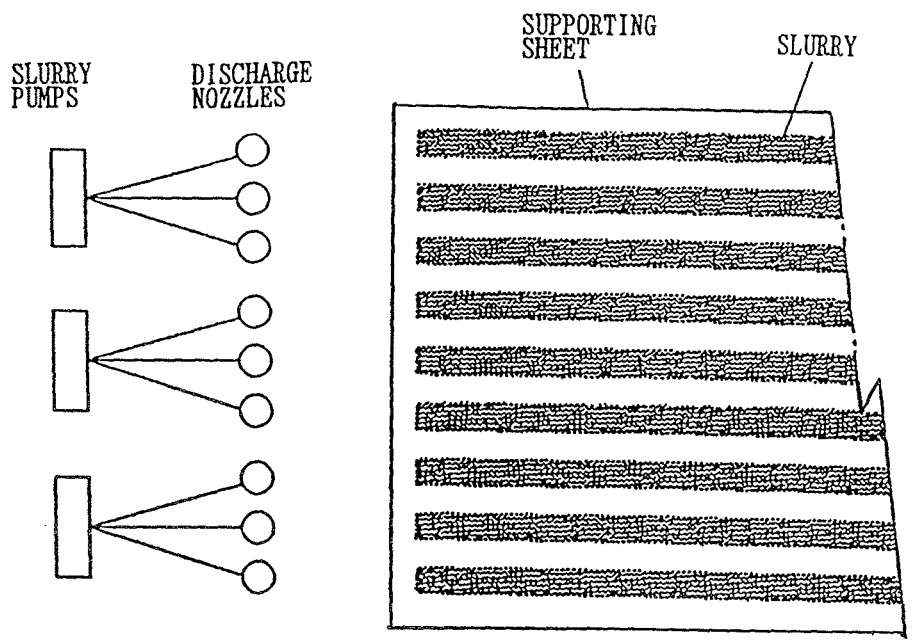
FIG. 90 is an explanatory drawing showing a process of applying a slurry onto a supporting sheet in many bands extending in parallel at intervals.

Slurry to be obtained by dispersing the SAP and the MFC in a dispersion medium of water/organic solvent, when the slurry is discharged from a nozzle and applied to a supporting sheet to form a absorbent sheet, is likely to be separated into two phases depending upon the conditions of the dispersion medium, solids may settle. Therefore, the solids in the slurry may settle in the transportation in a configuration of the apparatus where, as shown in FIG. 61, the slurry is guided to a nozzle via a dispersion tank, a slurry pump, a pipe, and a header (supplying tank). In such case, it is preferable to directly connect a discharging nozzle to each slurry pump and to apply the slurry from this discharging nozzle. FIG. 90 shows an example of this structure: slurry is applied in may bands extending in parallel at intervals.

Figure 91:
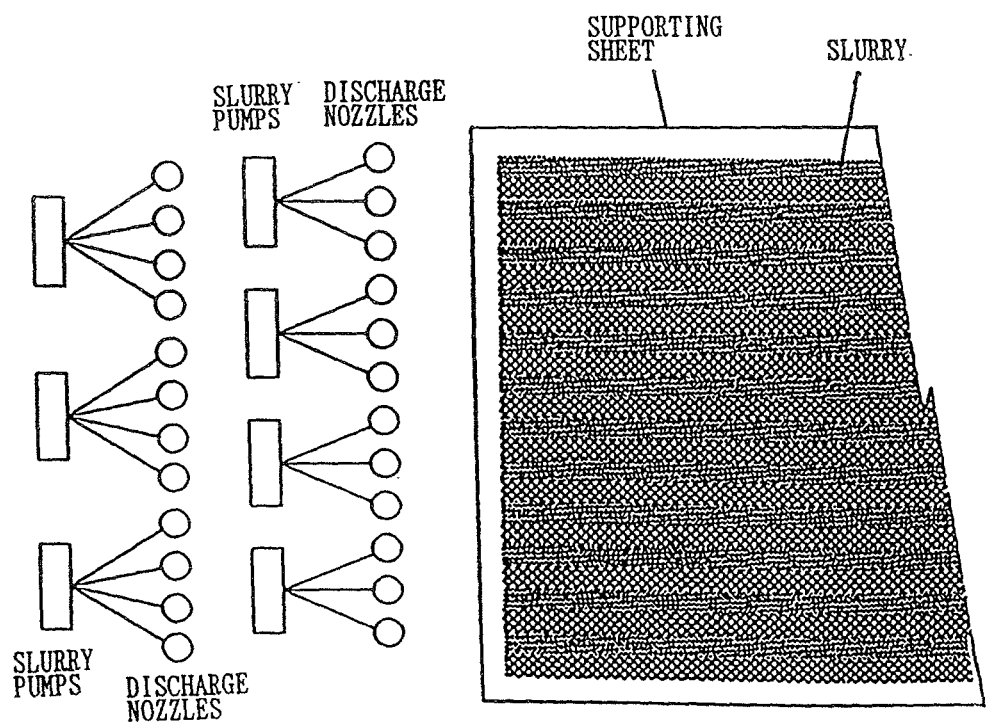
FIG. 91 is an explanatory drawing showing a process of applying a slurry onto a supporting sheet in many bands extending in parallel in contact with each other.

In the configuration illustrated in FIG. 90, slurry is applied in many bands extending in parallel at intervals on a supporting sheet as shown in FIG. 91. In applying the slurry on the whole surface of the supporting sheet, two pairs of a plurality of slurry pumps provided with a plurality of discharging outlets may be arranged in front and in rear in the direction of running of the supporting sheet so that the discharging nozzle in rear are disposed in between the discharging nozzles in front.

EXAMPLES

The examples of practicing the present invention are described hereunder:

Example 1

Preparing the HFFM Dispersion Liquids

Ethyl alcohol and ion-exchanged water were added to a dispersion liquid of the S-MFC (made by Tokushu Paper Mfg. Co., Ltd.) in gel state of 3.0% water dispersion as a stock liquid, to make three kinds of microfibril dispersion liquid where the ratio of ethyl alcohol/water was 70/30 and the concentrations of the S-MFC were 0.25%, 0.5% and 1%, respectively.

Preparing the HFFM/SAP Coexistent Dispersion Liquids 10 grams of the SAP (made by Sanyo Chemical Industries, Ltd. under the trademark "IM-6700") passed by 60 to 100 mesh was added to 50 cc of each of the above-mentioned three kinds of the HFFM dispersion liquid to prepare the HFFM/SAP dispersion slurry.

The prepared dispersion slurry is described as follows:

TABLE 2

| Experiment No. | Ethyl alcohol/water | Concentration of S-MFC (%) | S-MFC/SAP × 100 (%) |
|---|---|---|---|
| No. 1 | 70/30 | 0.2 | 0.1 |
| No. 2 | 70/30 | 0.5 | 2.5 |
| No. 3 | 70/30 | 1.0 | 5.0 |

Forming the HFFM/SAP Composite Sheet Material

Each of the dispersion liquids while stirred was subjected to removing the liquid component under a pressure reduced by an aspirator, and then dried at 5° C. under reduced pressure while spread on a PP non-woven fabric.

The composite after dried was formed in soybean shaped lumps. The composite in lumps as wrapped in a fine mesh shirting was crushed with a wood hammer, and passed by a 40 to 60 mesh to run absorbing tests.

TABLE 3

| Experiment No. | Crushed state |
|---|---|
| No. 1 | Relatively easily crushed |
| No. 2 | Hardened and hard to be crushed |
| No. 3 | Hardened in pebble-like lumps and stickly, and extremely hard to be crushed |

The highly absorbent composite crushed into powder had, observed by a microscope, its surface covered with the HFFM as shown in FIGS. 7(a) and 7(b).

Evaluating Absorbency

The water absorbing speed, gel block state, absorbed amount of water, and retained amount of water of the above-described SAP (both passing by 60 to 100 mesh and 40 to 60 mesh) were measured. For the absorbing speed, an initial absorbing time (sec.) required for absorbing 20 cc of water was measured. For the absorbed amount of water and the retained amount of water, the SAP, after dipped in an excessive amount of physiological saline solution, was measured in accordance with JIS K-7223. The measured results are as shown in Table 4:

TABLE 4

|  | Blank | No. 1 | No. 2 | No. 3 |
|---|---|---|---|---|
| Absorbed amount of physiological saline solution (g/g) | 45 | 47 | 44 | 46 |
| Retailed amount of physiological saline solution (g/g) | 35 | 34 | 34 | 36 |
| Absorbing speed of physiological saline solution (sec.) | 15 (Unswollen lump generated) | 5 | 10 | 30 (Unswollen lump partly generated) |

As clearly shown in the above-tabulated results of measurements, the absorbency and the water retention were little affected by adding the S-MFC. On the other hand, as the concentration of the S-MFC was increased from No. 1 to No. 3, the bonding strength of the SAP was increased, but the SAP became harder to handle because it was hardened. Moreover, since the concentration increased, the absorbing speed was lowered. Therefore, in such applications as such properties (absorbing speed and the like) are important, the percentage of the HFFM to be added to the SAP should be preferably 5% or lower.

Example 2

Concentration of the HFFM and the Properties of a Composite Sheet Material

Preparing the HFFM Dispersion Liquid

Preparing a Bacteria Cellulose (BC) Stock Solution

BC (made by B.P.R.) where the concentration of solids was 30% was stirred and dissolved in ion-exchanged water by a mixer for approximately 2 hours to prepare a stock solution where the concentration of solids was 1.2%.

Preparing Ethyl Alcohol/Water Dispersion Liquids of BC

Ethyl alcohol and water were added to a prescribed amount of the stock solution to prepare BC dispersion liquids of 0.02% to 0.80% BC.

Preparing the HFFM/SAP Coexistent Dispersion Liquid 5 grams of the SAP (made by Sanyo Chemical Industries, Ltd.) was added to 50 cc of each of the dispersion liquids of 0.02% to 0.8% BC to prepare BC/SAP dispersion liquids. In case the concentration of the BC was lower in the dispersion liquid, the SAP settled, but as the concentration of the BC became higher, it became stabilized. By stirring with a stirrer, the systems were kept stabilized to match the conditions of the systems as desired.

The descriptions of thus obtained BC/SAP coexistent dispersion liquids are as follows:

TABLE 5

| Experiment No. | Ethyl alcohol/water | Concentration of BC (%) | BC/SAP × 100 (%) |
|---|---|---|---|
| No. 11 | 70/30 | 0.02 | 0.2 |
| No. 12 | 70/30 | 0.05 | 0.5 |
| No. 13 | 70/30 | 0.10 | 1.0 |
| No. 14 | 70/30 | 0.20 | 2.0 |
| No. 15 | 70/30 | 0.40 | 4.0 |
| No. 16 | 70/30 | 0.80 | 8.0 |
| Blank | 70/30 | 0 | 0 |

Forming the HFFM/SAP Composite Sheet Material

A filter paper and a substrate non-woven fabric (made by Futamura Chemical Co., Ltd. under the trademark "TCF 403", of an apparent specific density of 0.07 gram/cm³) were laid on a Buchner funnel of a 11 cm inner diameter as connected to a pressure reducing apparatus, and 20 cc of the sticky dispersion liquid was poured quickly onto the substrate non-woven fabric. The non-woven fabric was subjected to removal of the liquid component under reduced pressure and dried in hot air to form a composite sheet.

Comparison of the Properties of Composite Sheet Materials

The properties of the composite sheet materials where the concentrations of the BC were different were evaluated and compared, which results are shown in Table 6. The experimental results show that, as the added amount of the BC was increased, the surface strength of the composite sheet materials was increased very much while the rigidity of the sheets was increased on the other hand. Therefore, it is necessary to properly select the added amount of the BC according to the applications.

TABLE 6

| | Experiment No. | | | | | | |
|---|---|---|---|---|---|---|---|
| | No. 11 | No. 12 | No. 13 | No. 14 | No. 15 | No. 16 | Blank |
| BC/SAP ratio (%) | 0.2 | 0.5 | 1.0 | 2.0 | 4.0 | 8.0 | 0 |
| Thickness (mm) | 0.60 | 0.60 | 0.55 | 0.56 | 0.58 | 0.57 | 0.55 |
| Weight (g/cm²) | 126 | 131 | 128 | 126 | 135 | 130 | 135 |
| Deposited SAP + BC (g/cm²) | 88 | 93 | 90 | 88 | 97 | 92 | 97 |
| Apparent specific gravity(g/cm³) | 0.22 | 0.24 | 0.24 | 0.24 | 0.25 | 0.24 | 0.28 |
| Rigidity (mm) | 85 | 78 | 68 | 40 | 25 | 15 | 85 |
| 180 degree peeling test using cellophane adhesive tape | Grade 2 | Grade 3 | Grade 3 | Grade 4 | Grade 5 | Grade 5 | Grade 1 |

The evaluation methods for evaluation items are described below:

Thickness (mm): Measured by a thickness gauge (JIS) in the same way as described in the above.

Weight (g): Measured together with the substrate of 110 mm diameter by an electronic Roberval balance.

Deposited SAP and BC (g/m²): Calculated by deducting the substrate non-woven fabric from the above weight and expressed in grams per square meter.

Apparent specific density (g/cm³): Calculated from the thickness and the weight of the substrate non-woven fabric and the weight of the deposited SAP and BC.

Figure 77:
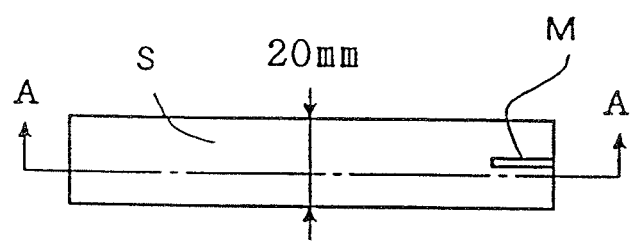
FIG. 77 is an explanatory drawing showing a method of measuring a stiffness and flexibility (mm)
Figure 78:
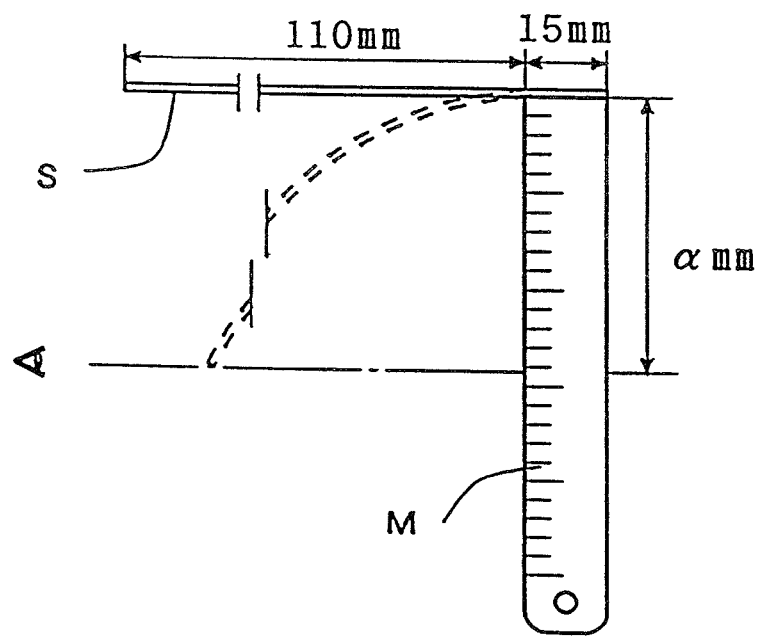
FIG. 78 is a fragmentary sectional view taken along section line A-A of FIG. 77.

Rigidity (mm): A sample of 110 mm×20 mm was measured by a method as shown in FIGS. 77 and 78. One end of the sample S was placed at the edge of a stainless steel measure M at right angle, and the scale of the measure was read at the position where the sample sagged (a mm).

Evaluating the Bonding Stability of the SAP (180 Degree Peeling Test Using Cellophane Adhesive Tape)

Figures 79, 80:
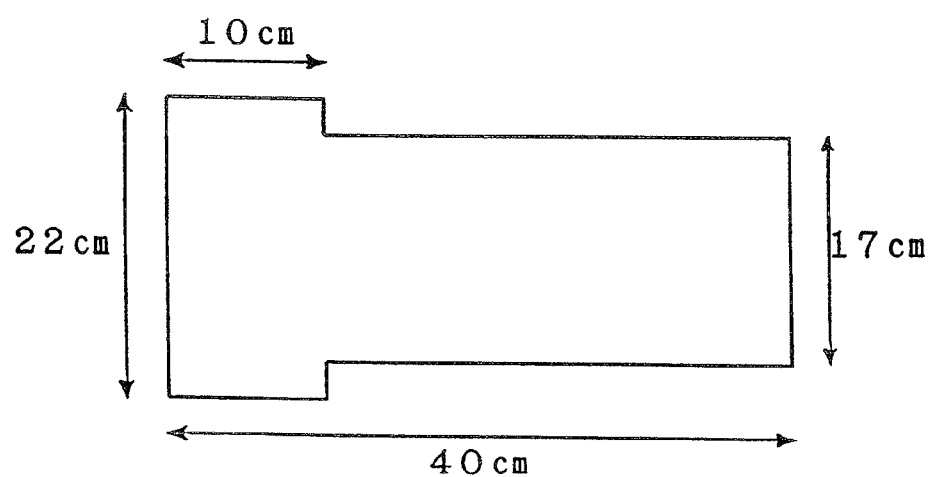
FIG. 79 is a chart drawing showing a criterion of the bonding stability of the SAP.
FIG. 80 is a plan view showing a composite absorbent sheet prepared for incorporating into a sample piece in an example of the present invention.

A cellophane adhesive tape (made by Nichiban Co., Ltd. under trademark "CELLOTAPE") of 15 mm width was adhered on the sample in an adhered area of 15 mm×10 mm, and the adhered area was pressed lightly with a flannel cloth, and a load of 1 kg/cm² was applied for 10 minutes. After the load was removed, the cellophane adhesive tape was peeled off by hand from the sample in a 180 degree peeling condition. By measuring the adhered area (%) of the SAP adhered on the cellophane tape, the bonding strength of the HFFM was judged by such adhered area of the SAP. The judgement criteria are shown in FIG. 79.

Evaluating Absorbed Amounts of Water and Retained Amounts of Water by Composite Samples The composite samples were dipped in a sufficient amount of physiological saline solution for 30 minutes and then the absorbed amounts of water and the retained amounts of water were measured by JIS K-7223. The measurements were converted into the SAP contents. The results are shown in Table 7 below:

TABLE 7

| Experiment No. | Absorbed amount of water (times) | Retained amount of water (times) |
|---|---|---|
| Used SAP samples (Blank) | 45 | 37 |
| No. 12 | 44 | 36 |

TABLE 7-continued

| Experiment No. | Absorbed amount of water (times) | Retained amount of water (times) |
|---|---|---|
| No. 13 | 46 | 38 |
| No. 14 | 48 | 36 |

Example 3

Continuous Coating Experiments

A highly absorbent composite was made by using an apparatus as shown in FIG. 61 provided with a coating unit as shown in FIG. 63, using the following materials:

(1) Microfibril: S-MFC (made by Tokushu Paper Mfg. Co., Ltd.)
(2) SAP: 1M-4000 (made by Hoechst-Celanese Co.)
(3) Suspension medium: Acetone/water system

| | Component | % by weight |
|---|---|---|
| (4) Coating composition: | S-MFC | 0.4 |
| | SAP | 30.0 |
| | Acetone | 48.8 |
| | Water | 20.8 |

(5) Supporting sheet: A two-layered through-air thermal bond web non-woven fabric (40 g/cm², apparent specific density of 0.06) having the following composition was used:
Upper layer: Mixed web of rayon (4 denier×45 mm length (70%)) and PE/PET (2 denier×45 mm length (30%)), approximately 25 g/cm²
Lower layer: Single web of PE/PET bicomponent fiber (2 denier×45 mm length), approximately 15 g/cm².

A mixture dispersion liquid of the composition in (4) above was continuously applied in approximately 10 mm width at an interval of 5 mm width onto the surface of the supporting sheet 13 while the sheet was conveyed at a speed of 10 m/min. Afterwards, the solvent was removed from the supporting sheet as compressed by a roll, and then dried in hot air.

The obtained highly absorbent composite sheet had the following characteristics:

| | |
|---|---|
| Weight | 195 g/cm² |
| Amount of SAP | 150 g/m² |
| Rigidity | Longitudinal: 20 mm |
| Lateral | 75 mm |
| Surface strength | class 5 (180 degree peeling test) |

The retained amount of water in the absorbent was measured by JIS K-7223. As a result, the SAP retained water at the rate of 40.2 grams of water per 1 gram of the SAP, which was nearly equivalent to the level of the "blank".

Example 4

A commercially available ultra thin disposable diaper was used as the "blank". A sample was prepared by removing absorbent components including tissue from one of such disposable diapers and by, for such absorbent components, incorporating an absorbent composed of a highly absorbent composite of the present invention.

The absorbent incorporated in the sample was prepared in the following procedure: first, a composite sheet as obtained in Example 3 above was cut in a shape and dimensions as shown in FIG. 80. On the other hand, a pulp mat provided with tissue of approximately 90 g/cm² was prepared. Water drops were sprayed onto the composite sheet by a hand spray for a domestic use iron to make the weight of the sheet 2 to 3 g/cm². The cut absorbent was laid on the sheet, and pressed under pressure by a iron at a temperature of 140 to 150° C.

Five pieces of the sample were prepared. For each sample piece, the absorbed amount of water, retained amount of water and rewet were measured. The absorbed amount of water and the retained amount of water were measured by JIS K-7223. The rewet was measured as follows: 120 cc of physiological saline solution was poured onto a sample three times at 5 minute interval, and the rewet was measured for each of the three times under the pressure of 12.5 kg per absorbent area.

The above-mentioned test results are tabulated in the following table. The measurements are shown in the average of the five sample pieces.

TABLE 8

| | Blank | Sample of the present invention |
|---|---|---|
| Configuration of absorbent Measurement item | | |
| Thickness (mm) | 3.2 | 1.5 |
| Weight of whole absorbent (g/p) | 26.0 | 17.5 |

TABLE 8-continued

| | Blank | Sample of the present invention |
|---|---|---|
| Fluff pulp (g/p) | 11.8 | 6.1 |
| Tissue (g/p) | 4.0 | 0.5 |
| SAP (g/p) | 10.2 | 10.9 |
| Property of absorbent Measurement item | | |
| Absorbed amount of water (g/p) | 665 | 557 |
| Retained amount of water (g/p) | 420 | 42.5 |
| Re-wet (g) | | |
| First re-wet (120 cc) | 0.6 | 0.4 |
| Second re-wet (240 cc) | 0.8 | 0.9 |
| Third re-wet (360 cc) | 3.9 | 2.2 |

From Table 8 it is shown that a sample where an absorbent composed of a highly absorbent composite of the present invention, which is approximately 70% in weight and one half in thickness of a commercially available disposable diaper, has equivalent or superior absorbing properties compared with the latter.

Example 5

1) Preparing a SAP Slurry

To a dispersion liquid of 2.15% water of the S-MFC (made by Tokushu Paper Mfg. Co., Ltd. under trademark "Super Microfibril Cellulose"), required amounts of water and ethanol were added to prepare a ethanol/water dispersion liquid (ethanol/water ratio being 60/40) where the concentration of MFC was 0.86% by weight.

To this dispersion liquid a short-cut staple fiber component composed of low melting point polyester/PET bicomponent fiber of 1.5 denier and 2 mm fiber length was added in an amount equivalent to the amount of the S-MFC, and dispersed with a mixer. Then, as it was stirred in a stirrer with a propeller, a required amount of the SAP (made by Mitsubishi Chemical Co., Ltd. under the trademark "Aquapearl US-40") was added to make a three component slurry composed of 30% by weight SAP, 0.6% by weight MFC and 0.6% by weight short-cut staple fiber component.

2) Preparing a Supporting Sheet

A two-layered spun-lace non-woven fabric where a first layer was composed of fine denier rayon fiber of 1.25 denier and 51 mm length and a second layer was composed of coarse denier PET fiber of 6 denier and 51 mm length was prepared. The weight of this non-woven fabric was 30 g/m², with an apparent specific density of 0.025 g/cm³, with the first later of higher density and the second layer of lower density.

3) Preparing Composite Absorbent

The three-component slurry was applied onto the second layer of the supporting sheet with a coater in an amount to make the deposited amount of the SAP 150 g/m². Then, immediately after it was sucked and the liquid component was removed, it was hot pressed for a few minutes at 180° C. The supporting sheet was then dried in hot air to make a composite absorbent (I).

Also, the composite absorbent (I) was then dried in hot air again at 150° C. to make a composite absorbent (II).

The structure of the absorbent composites (I) and (II) was observed by a microscope. As shown in a sketch of FIG. 54, it was confirmed that on a second layer 111b of a supporting sheet composed of a first layer 111a and the bulky second layer 111b and in the space, the SAP particles 112 were piled and the short-cut staple fiber component existed as entangled with the SAP particles and covering the SAP particles like an umbrella, and, on the surfaces of the SAP particles and of the short-cut staple fiber component, the MFC 114 was deposited.

Comparative Example 1

In Example 1, a procedure applied in making the composite absorbent (II) was applied to make a composite absorbent (ii) except that no short-cut staple fiber component was added.
<Evaluating the Composite Absorbents>
With the three kinds of absorbent composites obtained in Example 1 and Comparative Example 1 used, the sustainability of the swollen SAP and the diffusion of absorbed liquid by the swollen SAP when wet were tested by the above-described testing methods. The test results are summarized in Table 9 below:
1) 2)

TABLE 9

| Composite absorbent | Sustainability of swollen SAP | | | Dispersion of absorbed liquid | |
| --- | --- | --- | --- | --- | --- |
| | Standing Sustainability | Standing falling-off | Vertically suspended | Absorbing time (sec.) | Time till dispersion finished (sec.) |
| (I) | ◉ | ◉~○ | ◉~○ | 3~4 | 40~50 |
| (II) | ◉ | ◉ | ◉ | 3~5 | 50~60 |
| (ii) | Δ | Δ | Δ | 3~4 | 40~50 |

From the test results tabulated in the above, the following judgements can be made:
① Sustainability of the Swollen SAP
The composite absorbent (I) showed a good retention of the swollen SAP, which was made with a bicomponent short-cut staple fiber containing an easy-to-melt component incorporated.

The composite absorbent (II) which was heat treated adequately showed an outstanding sustainability in a particularly rigorous test of a vertically suspended sustainability.

However, the composite absorbent (ii) in Comparative Example 1 where no short-cut staple fiber component was incorporated showed substantially lower sustainability of the swollen SAP than the absorbent composites (I) and (II) in Example 1.

This was probably because, by incorporating short-cut staple fibers containing easy-to-melt fibers and by heat treating, the short-cut staple fibers were fused with each other and the short-cut staple fibers and the stereo-specific fibers of the supporting sheet were fused in their contact points, so that stereo-specific networks were generated, which networks held the swollen SAP.
② Dispersion of Absorbed Liquid
Although it was feared that the combination of the easy-to-melt short-cut staple fibers and the thermal fusion of fibers by heat treatment would affect unfavorably the absorption and the diffusion speed of a liquid, there was none or little influence on the absorbing time and only a little influence on the time until diffusion was finished, which was a level never giving rise to any problems in practical use at all.

Example 6

1) Preparing the SAP Slurries
To a 0.5% water dispersion liquid of the BC (made by Ajinomoto Co., Ltd. under the trade-mark "BACTERIA CELLULOSE") as the HFFM, required amounts of water and ethanol were added to prepare an ethanol/water dispersion liquid (the ratio of ethanol to water being 60 to 40) where the concentration of the BC is 0.21% by weight.

To this dispersion liquid, PE pulp (made by Mitsui Chemical Co., Ltd. under the trademark "SWP-E400") of 0.1 to 3 denier and 0.3 to 5 mm fiber length as the short-cut staple fiber component was added in amounts to make seven ratios of the short-cut staple fiber component to BC (P/Q ratio), and the mixture was dispersed uniformly by a mixer to prepare seven kinds of dispersion liquid of different mixing ratios.

In addition, to each of the seven kinds (different in mixing ratios of the BC and the SWP) of BC/SWP dispersion liquid while it was stirred by a propeller mixer, a required amount of the SAP (made by Mitsubishi Chemical Co., Ltd. under trademark "AQUAPEARL") was added to prepare seven kinds of three component slurry. In all the three-component slurries the concentration of the SAP was 15% and the ratio of the BC to the SAP was 1%. The concentrations of the components and the dispersion of the SAP in all the three component slurries are shown in Table 10 below:

TABLE 10

| Concentration of BC (P) (%) | 0.15 | 0.15 | 0.15 | 0.15 | 0.15 | 0.15 | 0.15 |
| --- | --- | --- | --- | --- | --- | --- | --- |
| Concentration of SWP (Q) (%) | 0.015 | 0.03 | 0.05 | 0.15 | 0.45 | 0.75 | 1.50 |
| P/Q ratio | 10/1 | 5/1 | 3/1 | 1/1 | 1/3 | 1/5 | 1/10 |
| Suspension of SWP | SWP stably | SWP stably | SWP stably | SWP stably | SWP not coagurated, though concentration gets high. | SWP coagurated, but can be used as slurry. | SWP coagurated, like soybean cake, and can not be used as slurry. |

In the P/Q ratios of 10/1 to 1/3 (concentration of the SWP being 0.45%), there was no coagulation of the SWP and the SWP was stably dispersed, but when the ratio exceeded 1/5 (concentration of the SWP being 0.75%), the slurry became cloudy with a little coagulation seen but still could be practically used. However, in case the P/Q ratio was around 1/10, the SWP coagulated too much to make a slurry. Therefore, from the viewpoint of stable dispersion, the upper limit was judged to be 1/5 for practical purposes.
2) Preparing Supporting Sheets
A two-layered through-air thermal bond non-woven fabric was prepared, with a first layer composed of a mixed carded web of 50% rayon of 1.5 denier and 40 mm length and 50%

PE/PET bicomponent fiber of 2 denier and 51 mm length and a second layer composed of only PE/PET bicomponent fiber of 3 denier and 51 mm length laid on each other and bonded in hot air. The weight of the non-woven fabric was 30 g/m$^2$, and the apparent specific density was 0.02 g/cm$^2$.

3) Preparing Composite Absorbent

Onto the second layer of this supporting sheet each of the six kinds of three-component slurry (excepting the one which could not be prepared into a dispersion slurry because of the P/Q ratio 1/10 from the seven kinds of the three-component slurry) was applied by a coater in an amount to make the deposited amount of the SAP 150 g/m$^2$. After sucking and removing the liquid component were done, supporting sheets were heat pressed for several minutes by means of a heated roller at 180° C. and then dried in hot air to prepare six kinds of composite absorbent (III) to (VIII).

<Evaluating Composite Absorbents>

For the six kinds of composite absorbent the sustainability of the swollen SAP and the diffusion of absorbed liquid by the swollen SAP when wet were tested by the above-described testing methods. The test results are summarized in the following table:

TABLE 11

| Composite absorbent | P/Q ratio | Sustainability of swollen SAP | | | Dispersion of absorbed liquid | |
|---|---|---|---|---|---|---|
| | | Standing Sustainability | Standing sustainability | Vertically suspended | Absorbing time (sec.) | Time till dispersion finished (sec.) |
| (III) | 10/1 | ○ | ○ | ○ | 3~5 | 50~60 |
| (IV) | 5/1 | ◉ | ○ | ○ | 5~7 | 50~60 |
| (V) | 3/1 | ◉ | ○ | ○ | 6~8 | 60~80 |
| (VI) | 1/1 | ◉ | ◉ | ◉ | 8~10 | 80~100 |
| (VII) | 1/3 | ◉ | ◉ | ◉ | 20~30 | 150~200 |
| (VIII) | 1/5 | ◉ | ◉ | ◉ | 30~50 | 240~300 |

From the above-tabulated test results the following judgements can be made:

① Sustainability of the Swollen SAP

In the composite absorbent where the content of the SWP was low (P/Q=10/1), no remarkable improvement in sustainability of the swollen SAP was seen, but as the content of the SWP increased, the sustainability of the swollen SAP improved: at around 3/1 of the P/Q ratio, the retention reached a nearly constant level, and at the P/Q ratio of 1/1 or higher, the sustainability of the swollen SAP in wet state was excellent. The lowest limit for realizing the effects of the SWP seemed to be around the P/Q ratio of 5/1 for practical purposes.

② Dispersion of Absorbed Liquid

The speed of a composite absorbent absorbing a liquid and the speed of the absorbed liquid being dispersed in the composite absorbent were affected by the concentration of a short-cut staple fiber component combined and the P/Q ratio. For example, in the absorbent composites (III) to (VI) of the P/Q ratio ranging from 10/1 to 1/1, there was no appreciable difference among them and they were all good. However, in the absorbent composites (VII) and (VIII) of the P/Q ratio of 1/3 and 1/5, while the sustainability of the swollen SAP improved, the absorption of a liquid and the diffusion of a liquid tended to be lowered.

Example 7

1) Preparing a SAP Slurry

To a 2.15% water dispersion liquid of the S-MFC (made by Tokushu Paper Mfg. Co., Ltd. under the trademark "SUPER MICRO FIBRIL CELLULOSE"), required amounts of water and propylene glycol were added to prepare a water/propylene glycol (PG) dispersion liquid (PG/water=70/30) where the concentration of the MFC was 0.86.% by weight. To this dispersion liquid, a required amount of the SAP (made by Mitsubishi Chemical Co., Ltd. under the trademark "AQUA-PEARL US-40") was added to prepare a two-component slurry of 30% by weight SAP and 0.6% by weight MFC.

2) Preparing a Supporting Sheet

A two-layered through-air thermal bond non-woven fabric was prepared, with a first layer composed of carded web of PE/PET bicomponent fibers of 1.5 denier and 51 mm length and a second layer composed of PE/PET bicompoent fibers of 3 denier and 51 mm length laid on each other and bonded in hot air. The weight of this non-woven fabric was 30 g/m$^2$, and the apparent specific density was 0.03 g/cm$^3$.

3) Preparing a Composite Absorbent

The supporting sheet was placed on a plastic net with the second layer facing upward, and the above-described two-component slurry was applied by a roll coater onto the whole surface of the supporting sheet, as it was continuously conveyed, in an amount to make the deposited amount of the SAP 200 g/m$^2$. Immediately thereafter, sucking and removal of the liquid component were carried out. Then, a 0.5% wood pulp dispersion liquid was poured onto the slurry layer as a thin layer stream from a flow coater in an amount to make the wood pulp 2% (4 g/m$^2$) to the SAP. Immediately thereafter, sucking and removal of the liquid component were run so that no SAP swelled, the supporting sheet was then hot pressed for several minutes by means of a heated roller whose surface temperature was 150° C. Further, the supporting sheet was again dried in hot air at 140° C. to make a composite absorbent.

<Evaluating the Composite Absorbent>

The composite absorbent showed an outstanding sustainability of the swollen SAP: No swollen SAP came off or peeled off from the substrate. Also, since the surface of the supporting sheet was coated with hydrophilic wood pulp, the absorbency of a liquid was excellent and the diffusion of an absorbed liquid was also at a level not giving rise to any practical problems. It was confirmed that, when this composite absorbent was used as the absorbent of a baby diaper, no additional non-woven fabric layer for acquisition was required because, as the first layer and the topsheet were used as bonded together, the first layer functioned as the acquisition layer.

Example 8

The surface of a wet process non-woven fabric of 40 g/m$^2$ weight (made by Futamura Chemical Industries Co., Ltd.

under the trademark "TCF 404") was raised by a brush to make the apparent specific density 0.04 g/cm³.

On the raised surface of this supporting sheet, the SAP particles (made by Mitsubishi Chemical Co., Ltd. under the trademark "US-40") was scattered using a sieve as it was vibrated in an amount to make the scattered amount of 120 g/m².

Separately, a mixture dispersion liquid where the S-MFC and easy-to dissolve-in-hot-water PVA staple fiber (of 1.5 denier and 2 mm length) were dispersed in water in a way that the concentration of each of the MFC and the PVA fiber was 0.5% was prepared. The raised surface of the supporting sheet was coated with the mixture dispersion liquid by a flow coater in an amount to make the percentage each of the S-MFC and the PVA fiber to the SAP 1% (1.5 g/m²), and immediately thereafter, sucking and liquid removing of the liquid component were run. Then, the supporting sheet was hot pressed by a roller heated at 200° C., and dried in hot air at 100° C. to make a composite absorbent.

Only a little SAP came off or peeled off from the obtained composite absorbent, and thus had a level of sustainability of the swollen SAP not giving rise to any practical problems. The absorbing and diffusion of a liquid were extremely good. This was probably because both the supporting sheet and the short-cut staple fiber component were hydrophilic.

Example 9

1) Preparing a Three-Component Dispersion Liquid 1.4 denier and 3 mm length LYOCELL (trademark, made by Coutaulds) was added to and dispersed in a dispersion medium of ethanol/water=60/40 to prepare a 0.5% dispersion liquid. This dispersion liquid was stirred by a mixer to fibrillate Lyocell. Then, the MFC was added to and dispersed in the dispersion liquid in an amount to make the concentration of the MFC in the dispersion liquid 0.5%, and the dispersion liquid was treated for 5 minutes by a mixer to prepare a two-component dispersion liquid.

SAP flake (made by Hoechst-Celanese under the trademark "IM-4000") of 50 mesh was added to the two-component dispersion liquid while the dispersion liquid was slowly stirred in an amount to make the concentration of the SAP 25%, to make a three-component dispersion liquid of the SAP, the MFC and LYOCELL.

2) Preparing a Supporting Sheet

A mixed carded web was prepared composed of 50% rayon staple fiber (of 1.5 denier×35 mm length) and 50% PE/PET bicomponent fiber (of 3 denier×41 mm length) with the weight of 15 g/m², and the carded web laid on PP spun-bond non-woven fabric of 15 g/m² weight was entangled by water jet to make a plural layered non-woven fabric, which was made a supporting sheet.

3) Making a Composite Absorbent

As shown in FIG. 81, the three-component slurry 822 was discharged from a plurality of discharging tubes directly connected to a slurry pump onto the rayon staple fiber/bicomponent fiber surface of a supporting sheet 821 in the pattern as shown in FIG. 81. After removal of the liquid component under reduced pressure, the supporting sheet was fixed by a heat press and dried to make a composite absorbent.

The obtained composite absorbent was approximately 130 g/m² in terms of the total SAP applied, and the portions (SAP) formed in lines on the obtained composite absorbent was approximately 200 to 250 g/m².

4) Applying to the Absorbent for Use in Baby Diaper

As shown in FIG. 82(a), a dry laid carded web non-woven fabric 831 as the topsheet in contact with the skin of a wearer, as mainly composed of 18 g/m² PE/PET bicomponent fiber of 1.5 denier×41 mm length was prepared. Onto this non-woven fabric 831, polyurethane filament yarns 832 (made by Toray Co., Ltd. under the trademark "LYCRA") was bonded by hot melt method in rows at such intervals as shown in FIG. 82(a) to form a topsheet. The topsheet provided with an elastic member and a composite absorbent 833 as shown in FIG. 82(b) obtained in this Example 9 of the present invention were bonded by thermal fusion at the portions where no absorbent existed thereby a bonded member of the topsheet and the composite absorbent having a structure shown in FIG. 82(c) was obtained.

The bonded member was covered at the side of the composite absorbent by a leakage resistant member 834 made by bonding PE film and non-woven fabric as shown in FIG. 82(d) to obtain an absorbent for use in a baby diaper, of 200 mm width and 400 mm length. This absorbent was dipped in a physiological saline solution and then taken out and placed on a net so that a free liquid is removed from the absorbent. The total amount of the solution absorbed, as measured, was 600 cc. The initial penetration speed was 20 seconds with 100 cc, and the rewet was 0.5 gram. Thus, the composite absorbent of the present invention was proved to have excellent properties as the absorbent.

5) Applying for Use in Incontinent Pad for Women

As shown in FIG. 83, a slurry of the above-described composition 842 was applied onto a circular supporting sheet 841 as shown in FIG. 83(a) in a doughnut shape of 120 mm a circular supporting sheet 841 as shown in FIG. 83(a) in a doughnut shape of 120 mm diameter with a center hole of 50 mm diameter, and, after drying, the surface was covered with a hydrophobic spun-bond 843 to make a composite absorbent. This composite absorbent was folded in a folding fan-like shape as shown in FIG. 83(c), and the tip of the composite absorbent was covered with an apertured PE non-woven fabric 844 to make an incontinent pad of a structure as shown in FIG. 83(d). No absorbent existed at the portion where the apertured PE non-woven fabric 844 was provided and the portion which was in thin sheet was for partial insertion in a vagina for securing the pad to the body of a wearer. The amount of liquid retained by this incontinent pad was 50 cc, and the incontinent pad was used as a sample in a wearing test by a patient having a light incontinence with the result that the patient's underwear was not stained and that it can be used stably.

Example 10

<Preparing a Slurry>

A water dispersion stock solution of 3% by weight S-MFC was added to make a dispersion medium composed of 60 parts ethanol and 40 parts water, to prepare a dispersion liquid of 0.6% by weight S-MFC. Into this dispersion liquid, the SAP equivalent to 30% by weight (made by Mitsubishi Chemical Co., Ltd. Under the trademark "US-40" with the average particle diameter of 200 microns) was added while the SAP was stirred by a propeller mixer to prepare a slurry.

<Forming with the Slurry Pattern on a Supporting Sheet>

Using a slurry coating apparatus as shown in FIG. 76 (a slurry discharging part thereof being shown, as enlarged, in FIG. 66), the slurry was applied onto the top surface of 40 g/m² TCF (cellulosic non-woven fabric) used as a supporting sheet to form a pattern of slurry by means of tube pumps arranged in many rows in an amount to make the average deposited amount of the SAP 125 g/m². By the pulsation generated by the stroke of the tube pump, a sheet having the ellipsoidal pattern which has intermittently thicker slurry in the center regions was formed.

<Bonding the Slurry Formed in a Pattern to the Supporting Sheet>

A supporting sheet on which the slurry was formed in a pattern was hot pressed by means of a hot press roll of 160° C. and a suction roll, as shown in FIG. 76, and at the same time an excess of the dispersion medium was sucked and removed. Thereafter, the sheet was made to contact with a hot roll for approximately 5 seconds to remove the liquid component from the sheet and the applied slurry was bonded to the supporting sheet securely. Afterwards, the supporting sheet was peeled off from the hot roll and air dried to make an absorbent sheet. At that time, there was no deposit of the slurry on the hot roll because partially peeled off from the supporting sheet. For comparison, the sheet was passed at room temperature, with the hot roll not heated, in which case a majority of the slurry formed in a pattern on the supporting sheet was peeled off and deposited on the surface of the roll. From this fact the effects of bonding the SAP to the supporting sheet by hot roll were be confirmed.

After hot pressing, the dried sheet showed a distribution of patterns as shown in FIG. 55. The bonding to the supporting sheet was as shown in a fragmentary sectional view of FIG. 56, and the applied SAP was in one layer at the thin regions, in nearly thee layers at the thick regions and in nearly two layers at the medium regions. This difference in thickness, or in the number of layers, gave a desired distribution of the concentrations which were not uniform, but continuous.

<Properties of Pattern-Formed Sheets>

A sample piece taken from each of the regions having the thick SAP pattern, the thin SAP pattern and the medium SAP pattern was observed in cross-section by a magnifying glass, to confirm the number of the SAP layers whereby the amount of absorbed liquid and the absorbing speed were evaluated as the liquid absorbing properties of the SAP.

①Amount of absorbed liquid: Using a 0.9% NaCl aqueous solution (physiological saline solution), a method corresponding to a method of testing an amount of absorbed water of JIS K-7223 was applied.

②Absorbing speed: A plurality of sample pieces of approximately 5 mm×10 mm were dipped in a large amount of a 0.9% NaCl aqueous solution and the time until the SAP in a sample became nearly completely swollen in seconds was measured.

For the amount of liquid absorbed, sample pieces of 10 cm×10 cm were taken from the supporting sheet including from thickly to thinly coated portions and as the average value of the whole sheet, the total amount of liquid absorbed was 6.0 kg/m². As the process of absorbing a liquid was observed, it was confirmed that the thinly coated region, first, absorbed, and the absorbing progressed gradually to the medium coated and then to the thickly coated region. The differences in liquid absorbing speed among the regions are shown in Table 12:

TABLE 12

| | Region of sample | | |
|---|---|---|---|
| | Thinly coated region (one layer of SAP) | Medium coated region (two layer of SAP) | Thickly coated region (three layer of SAP) |
| Absorbing speed (sec.) | 10-15 | 30-60 | 90-180 |

From the above-tabulated results, it was confirmed that the obtained absorbent sheet was flexible and had a characteristic property of providing a distribution of highly absorbing regions different in absorbing speeds.

Example 11

<Preparing a Slurry from the SAP Having Different Particle Diameters>

The SAP whose average particle diameters were 200 microns and 800 microns were prepared. As the 200 micron sample Mitsubishi Chemical's US-40 as used in Example 10 was used as the blank, while as the 800 micron sample a pelletized SAP with higher surface cross-linking was used.

The following table shows the measurements of the time of absorbing 20 cc of physiological saline solution by 1 g of the SAP: As for the time of absorbing a liquid by the SAP (Refer to Example 10 above), as the particle diameter became larger, liquid took more time to penetrate into inside and the swelling became lower.

TABLE 13

| Average particle diameter of SAP (micron) | 200 | 800 |
|---|---|---|
| Speed of absorbing liquid | 10-15 | 60-150 |

Two kinds of slurry of 30% by weight SAP having the above-described properties were prepared in the same way as in Example 10 above.

<Coating of a Supporting Sheet with the Slurry>

Two headers were provided on a slurry coating apparatus as shown in FIG. 66 in order to feed two kinds of slurry containing the SAP whose particle diameters were different, and the apparatus was modified to feed different kinds of slurry alternately to the respective pumps.

Using this apparatus, two kinds of slurry were deposited in a pattern on the TCF side of a supporting sheet in an amount to make the average deposited amount of SAP 125 g/m², respectively, in a procedure similar to the one applied in Example 10 above. Thus, absorbent sheets with the slurry deposited in a pattern were obtained. In the distribution of the pattern in this case, as mentioned in the above, the rows of the pattern were coated with the SAP of different particle diameters alternately. Although the SAP of the same concentration was applied, because of the difference in particle diameter, the pattern where larger particle diameter SAP was applied was relatively thick.

The obtained sheet on which the SAP of different particle diameters was applied was cut into a size of 10 cm×10 cm, and placed in a Petri dish. 60 cc of physiological saline solution was added at three times of 200 cc each at 5 minute interval, and the state of absorption was observed. The observation results are shown in Table 14.

It was confirmed that finer particle SAP first swelled and the absorption progressed to coarser particle diameters.

TABLE 14

| Liquid supplied | Patterns in absorbent layer composed of SAP of small particle diameter | Patterns in absorbent layer composed of SAP of large particle diameter |
|---|---|---|
| First 200 cc | Swelling rapidly started | Surface a little seemed to be absorbing, but nearly dry condition continued |
| Second 200 cc | Swelling reach saturation | Overall swelling started, but there remained ample room left for absorbing |
| Third 200 cc | Excess of water travelling in supporting sheet and transferred to patterns of larger particle diameter SAP | Swollen overall reaching saturation |

Example 12

<Preparing a First Dispersion Liquid>

To wood pulp (made by Weyerhaeuser, NBKP, needle leaf wood bleached kraft pulp) and the SAP (made by Hoechst-Celanese under the trademark "IM-4500"), a small amount of thickener (P.E.O.) for paper-making was added to prepare a dispersion liquid of EtOH/water=50/50 containing pulp/SAP=4 parts/6 parts. The concentration of thus prepared slurry was approximately 2%.

<Forming an Absorbent Sheet from the First Dispersion Liquid>

The above-described slurry dispersion liquid was poured onto a PE/PET non-woven fabric (made by Unitika Co., Ltd. under the trade name "ELVES") of 20 g/m² treated to be hydrophilic disposed on a plastic mesh of 60 mesh to prepare a wet formed absorbent mat. By pressing and drying this absorbent mat, an absorbent sheet having 100 g/m² absorbent layers composed of pulp/SAP=4/6 was obtained.

<Preparing a Second Dispersion Liquid>

A slurry was prepared by including 30% SAP and 0.6% MFC in a dispersion liquid of EtOH/water=6/4 prepared in a procedure identical with the one applied in Example 10 above.

<Forming an Absorbent Sheet from the Second Dispersion Liquid>

Onto an absorbent sheet made from the above-described first dispersion liquid having uniform layers of pulp/SAP, slurry was fed in a sea island-like pattern at 5 mm intervals, using an experimental use tube pump (marketed under the trademark "MASTER FLEX") with the second dispersion liquid contained in a silicone rubber tube of 3 mm inside diameter. Then, the absorbent sheet was hot pressed, using a Teflon-coated domestic use iron heated at 130° C. and then dried. The layers formed from the second dispersion liquid had the SAP of approximately 120 g/m² on average, although thicker at some places and thinner at others.

<Absorbent Sheet Having Highly Absorbing Regions in a Sea Island Pattern and Its Properties>

Thus obtained absorbent sheet had a distribution of nearly uniform absorbent layers (containing the SAP of approximately 60 g/m²) derived from the first dispersion liquid and of absorbent layers (containing SAP of approximately 120 g/m²) derived from the second dispersion liquid which latter absorbent layers were distributed in a pattern given tails partly to the pattern shown in FIG. 16. Thus, an absorbent sheet having a thick and thin two layered structure was obtained.

The absorbent sheet was cut in 10 cm×10 cm to make a sample. The sample was placed in a Petri dish, and 0.9% physiological saline solution was poured to run multi times of absorbing test. The absorbing test was run four times at 5 minute intervals with 15 cc each. The test results are shown in Table 15.

Example 13

<Preparing a SAP Slurry>

A slurry composed of the SAP and the MFC was prepared in a procedure identical with the one applied in Example 10 above.

<Preparing a Liquid Pervious Supporting Sheet>

An air laid pulp sheet containing the SAP (made by Honshu Kinocloth under the trademark "B-SAP") whose weight was 85 g/m² was prepared. In this pulp sheet, the SAP of 20 g/m² was blended.

<Discharging the Slurry to Form a Pattern>

The above-described slurry from a slurry pump was discharged in a pattern arranged in many rows of bands having indefinite circumference each onto the above-described supporting sheet, as moving, from a nozzle having a cleavage-like discharging outlet as shown in FIG. 68. Then, the supporting sheet was pressed under pressure by a hot roll whose surface temperature was 140° C. and air dried to make an absorbent sheet. In the distribution of the patterns on this absorbent sheet, absorbent layers were distributed in a pattern similar to the one in the sketch of FIG. 17.

Example 14

The HFFM (made by Daicel Co., Ltd. under the trademark "Cellish KY100G") in gel state was dispersed in a dispersed medium of MeOH/water=70/30 to make a dispersion liquid of 0.6% concentration. In 1 liter of this dispersion liquid, 400 g of the SAP (made by Mitsubishi Chemical Co., Ltd. under the trademark "US40") was added and stirred to prepare a dispersion slurry of the HFFM and the SAP.

This co-dispersion slurry was applied on either surface of a cellulose non-woven fabric of 30 g/m² (made by Futamura Chemical Co., Ltd. under the trademark "TCF#403"), and the non-woven fabric was subjected to removal of the liquid component and dried to obtain an absorbent sheet. The thickness of this absorbent sheet was approximately 0.6 mm and the content of the SAP was 150 g/m².

Figure 84:
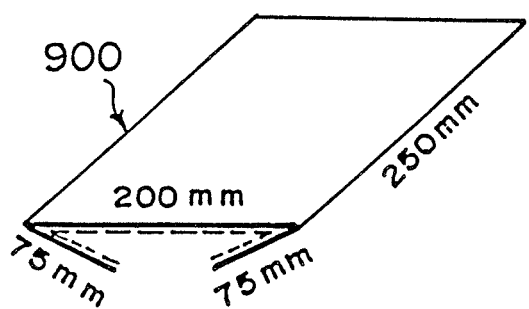
FIG. 84 is a perspective view showing material of an absorbent tube used in an example of the present invention.
Figure 85:
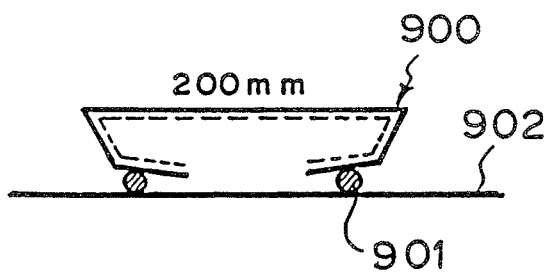
FIG. 85 is a cross sectional view of an absorbent tube constituted by the material of FIG. 84.

The absorbent sheet was cut in 350 cm×250 cm. As shown in FIG. 84, the sheet was folded inside at the position 75 mm each from both sides with the surface coated with the SAP facing inside to make an absorbent. Then, as shown in FIG. 85, the sheet was bonded to a liquid impervious sheet 902 at the folded sides via adhesive 901 to make an absorbent tube 900. The thickness of thus obtained absorbent tube 900 was 1.3 mm including the liquid impervious sheet 902.

Swelling test was run by pouring physiological saline solution of 200 cc each time twice, 400 cc in total, onto the absorbent side of the absorbent tube. The result was that 2 minutes after the first 200 cc was poured the absorbent side swelled in a tube having an ellipsoidal cross-section of

TABLE 15

| Amount of water added | State of absorption | Results of observation |
|---|---|---|
| First 150 cc added | Only thin layers absorbed | Dispersed all over first layer, second layer remained dry |
| Second 150 cc added | Absorption partly moved from first layer to second layer | Whole first layer became wet, but second layer only partly wetted |
| Third 150 cc added | Whole second layers started to swell | Boundary between first and second layers still distinct |
| Fourth 150 cc added | Whole first and second layers swollen | Second layer much swollen to have ridges | approximately 6 mm thickness, and 2 minutes after the second 200 cc was poured, the thickness increased to approximately 12 mm.

Example 15

A non-woven fabric (made by Oji Paper Co., Ltd. under the trademark "TECCEL") obtained by entangling PP/PE bicomponent spun-bond non-woven fabric and pulp together in high pressure jet stream was prepared.

On the other hand, commercially available bio-cellulose gel was dispersed in a dispersion medium of EtOH/water=60/40 to prepare a dispersion liquid of 0.3% concentration. In 1 liter of this dispersion liquid, 400 g of the SAP (made by Mitsubishi Chemical Co., Ltd. under the trade-mark "US 40") was added and stirred to prepare a co-dispersion slurry of the HFFM and the SAP.

Either surface of the above-described non-woven fabric was line-coated with this co-dispersion slurry in a plurality of bands of 7 mm width at 5 mm intervals, and the non-woven fabric was subjected to removal of the liquid component and dried to obtain an absorbent sheet.

Figure 86:
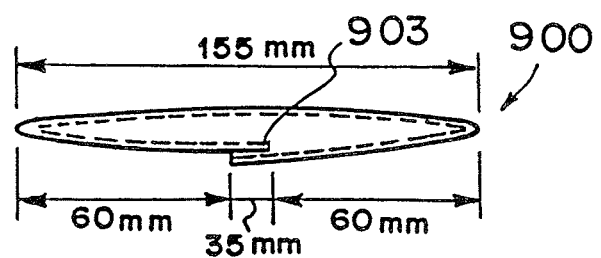
FIG. 86 is a cross sectional view of an absorbent tube used in an example of the present invention.
Figure 87:
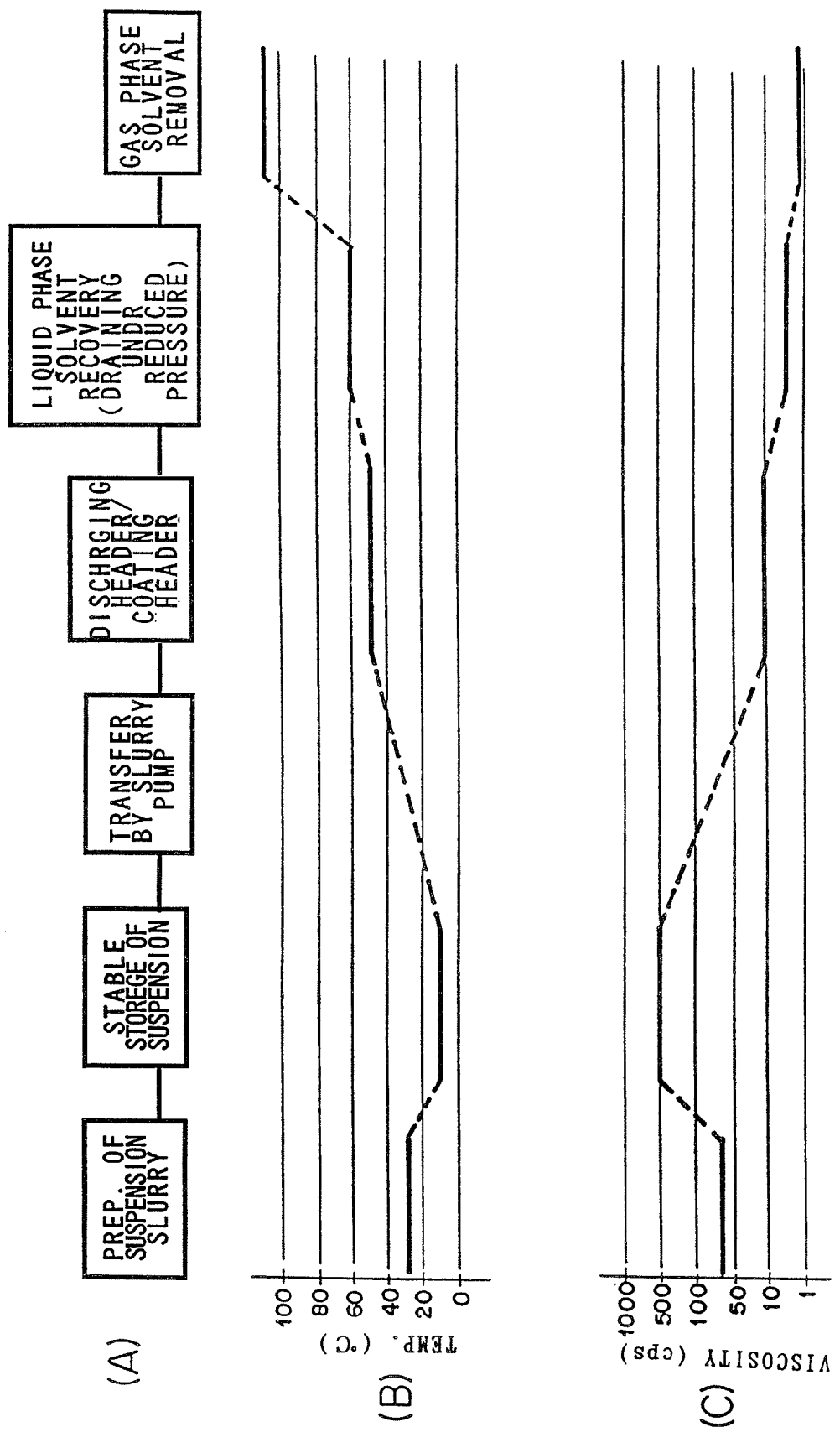
FIG. 87 shows an example of setting a viscosity and a temperature in each area of a process with propylene glycol as an example: (A) is a process flow thereof, (B) is a chart showing a fluctuation of temperature in each area of the process, and (C) is a chart showing a fluctuation of viscosity in each area of the process.

The absorbent sheet was cut in 350 mm×250 mm, and then, the cut sheet was folded with the SAP applied surface facing inside in a flat cylindrical shape as shown in FIG. 86, and the folded portions of both sides were bonded together via adhesive 903 to make an absorbent tube 900. The thickness of thus obtained absorbent tube was approximately 2 mm.

Swelling test was run by pouring physiological saline solution of 200 cc each twice, 400 cc in total, onto the absorbent tube. The result was that 2 minutes after the first 200 cc was poured, the absorbent tube swelled in a tube shape having a ellipsoidal cross-section of approximately 10 mm, and 2 minutes after the second 200 cc was poured, the thickness increased to approximately 20 mm.

Example 16

A PP spun-bond of 18 g/m$^2$ and a mixed carded fiber web of 30 g/m$^2$ composed of 60% PET staple fiber (3 denier×51 mm length) and 40% rayon staple fiber (1.5 denier×35 mm length) were prepared. Such mixed carded web laid on such spun-bond non-woven fabric was entangled in high pressure water jet stream to prepare a composite non-woven fabric of a structure as shown in FIG. 37.

The composite non-woven fabric was coated with a co-dispersion slurry of the HFFM and the SAP used in Example 14 above, and subjected to removal of the liquid components and dried to obtain an absorbent sheet of approximately 2 mm thickness composed of three layers of the spun-bond non-woven fabric, the carded web, and the SAP layer fixed by the HFFM, only on either surface of which absorbent sheet the SAP particles were carried at the density of 150 g/cm$^2$.

This absorbent sheet was cut in bands of 350 mm width, and the cut sheet was formed in tube with both longitudinal sides made to face each other at approximately 30 mm interval.

Separately, from a disposable diaper (manufactured by Kao Corporation under the trade name "Super Merries (L size)"), the inner sheet and the absorbent core were taken out, and, instead in the region where such sheet and core existed as shown in FIG. 38, the above-described absorbent tube in contact with the exposed outer sheet of the diaper was linked to the liquid impervious sheet at both side ends via adhesive.

On thus obtained diaper, absorbing tests were conducted in a procedure generally practiced in this field. As the result of the tests, the following results were obtained:

① Amount of rewet (3 minute interval)
  First rewet (100 cc): 0.5 g
  Second rewet (100 cc): 0.8 g
  Third rewet (100 cc): 2.0 g
② Total absorbed amount (physiological saline solution): 680 cc
Retained amount: 480 cc Example 17

A PE/PET bicomponent non-woven fabric of 20 g/m$^2$ weight (made by Unitika Co., Ltd. under the trademark "ELVES") was stretched and heat set as shown in FIG. 57 to prepare a easy-to-elongate non-woven fabric. This non-woven fabric had the following properties:

| | |
|---|---|
| Weight | 31.2 g/m$^2$ |
| Thickness | 0.24 mm |
| Density | 0.132 g/cm$^3$ |
| Breaking elongation | 35% (MD)/370% (CD) |
| 100% elongation modulus in CR | 83 g/5 cm. |

The above-described easy-to-elongate non-woven fabric was coated with a co-dispersion slurry of the HFFM and the SAP in a procedure identical with the one applied in Example 14 above, and heated and pressed and subjected to removal of the liquid component and dried to obtain an absorbent sheet with the SAP particles carried in a density of 180 g/m$^2$ only on either surface. The absorbent sheet was folded in tube with the surface carrying the SAP facing inside. Both side ends of the sheet were made to face and bonded at the meeting portion of both side ends with a thermal adhesive tape disposed on the outside to prepare an absorbent tube of approximately 30 mm outer diameter having nearly circular cross-section.

Thus obtained absorbent tube was placed in a plastic vat, and ion exchanged water was poured on the absorbent tube until the tube did not absorb water any more, and allowed to stand for 10 minutes. As a result, the diameter of the absorbent tube increased to 66 mm, but no SAP was observed to leak from the outside of the non-woven fabric.

Example 18

An elastic net of 60 g/m$^2$ weight commercially available on the market was prepared as an absorbent sheet, where polyethylene monofilaments as longitudinal filament members and SEBS monofilaments as lateral filament members were crossed at right angle with each other and bonded at the points of intersection.

Separately, a carded parallel web of 25 g/m$^2$ composed of the following fibers A and B was prepared:
  A: bicomponent fiber of 2 denier×51 mm length, composed of a random polymer of poly-propylene as the core and ethylene/propylene as the sheath.
  B: LYOCELL made by Coutaulds of 1.5 denier×35 mm length.

A carded parallel web A was laminated on one surface of the above-described elastic net and another carded parallel web B was laminated on the other surface of the net, and the net with the carded parallel webs were entangled by water jet stream one time each on the top and the bottom side of the laminated members under the pressure of 50 kg/cm$^2$ from a nozzle having orifices of 0.13 mm diameter provided at 0.6 mm interval. Further, water stream was jetted from the top under the pressure of 80 kg/cm$^2$ from a nozzle having orifices of 0.13 mm diameter provided in one row at 5 mm interval.

Then, the laminated members were dehydrated and dried to make an easy-to-stretch non-woven fabric with bonded portions in parallel lines formed longitudinally, of a structure as shown in FIGS. 59 and 60.

The properties of the non-woven fabric were as follows:

| Weight | 110.00 g/m$^2$ |
| Thickness | 1.22 mm |
| Tensile strength in CD | 1.50 kg/5 cm |
| Elongation in CR | 270.00% |
| Elongation modulus in CD | |
| 50% | 150 g/5 cm |
| 100% | 200 g/5 cm |
| 150% | 320 g/5 cm |

(Notes) The above-described properties were measured under the following conditions:

Tensile strength: A sample piece of 5 cm width and 15 cm length (the cross direction of the non-woven fabric being the longitudinal direction of the sample) was held at the holding distance of 10 cm, and elongated at the rate of 30 cm per minute by means of a constant rate stretching type tensile tester. The load value at breaking was taken as the tensile strength.

Elongation modulus: A sample piece of 5 cm width and 15 cm length (the direction of the non-woven fabric being the longitudinal direction of the sample) was held at the holding distance of 10 cm, and elongated 150% at the rate of 30 cm per minute by means of a constant rate stretching type tensile tester. From the stress-strain curve obtained at that time, the stress each at 50%, 100% and 150% elongation was read out. The readings were taken as the elongation modulus.

Thickness: The thickness was measured by a thickness gauge (made by Daiei Kagaku Seiki Co., Ltd. under the trademark "THICKNESS GAUGE") under a load of 3 g per 1 cm$^2$.

The LYOCELL side of the above-described easy-to-stretch non-woven fabric was coated with a co-dispersion slurry of the HFFM and the SAP in a procedure identical with the one applied in Example 14 above. The non-woven fabric was subjected to removal of the liquid component and dried to obtain an absorbent sheet with the SAP particles carried in a density of 125 g/m$^2$ only on one surface. Further, a crushed wood pulp layer of 150 g/m$^2$ was laid on the side of the absorbent sheet that carried the SAP particles, with such side facing inside the absorbent sheet was folded in a tube with the side ends facing each other at 30 mm interval and bonded to a separately prepared polyethylene outer sheet by means of hot melt type adhesive to obtain a absorbent tube bonded in an integrated way to the outer sheet. The thickness of this absorbent tube was approximately 4 mm.

The thus obtained absorbent tube was placed in a plastic vat, and from the top of the absorbent tube ion-exchanged water was poured until the absorbent tube did not absorb water any more, and allowed to stand for 10 minutes. As a result, the thickness of the absorbent tube increased to 30 mm, but no SAP was observed to leak to the outside of the non-woven fabric.

Example 19

<Preparing a Liquid Impervious Sheet Having Dents on the Surface>

Polyethylene film of 30 microns having taper-like openings, as shown in FIG. 39, all over the surface (made by Tredgar under the trademark "VISPORE X-6170") was prepared.

<Preparing a Slurry of Absorbent Materials>

Separately, MFC gel (made by Daicel Co., Ltd. under the trademark "CELISH KY-100G") was dispersed in a dispersion medium of ethanol/water=70/30 to prepare 1 liter of dispersion liquid of 0.5 MFC. To this dispersion liquid, 200 g of the SAP particles (made by Mitsubishi Chemical Co., Ltd. under the trademark "US40") was added to prepare a co-dispersion slurry of the SAP and the MFC.

<Preparing an Absorbent Sheet>

The above-described polyethylene film having openings was, with the surface having larger openings facing upward, was coated with the co-dispersion slurry of the SAP and the MFC as the polyethylene film was fed and conveyed on a belt conveyor of plastic belt of 80 mesh provided with a suction zone.

In the suction zone the co-dispersion slurry of the SAP and the MFC on the polyethylene film having openings was subjected to removal of the liquid component through the openings to fill inside the openings with the solid substance in the slurry. Then, the solid substance was dried by blowing hot air of 80° C. onto the solid substance.

The openings of the absorbent sheet had, as observed by a microscope, a structure as shown in FIG. 40.

<Evaluating the Permeability>

Permeability tests were conducted on the absorbent sheet by a Garret type test method provided in JIS P117. The result was that the air permeability of the absorbent sheet was 100 sec/100 cc.

<Measuring the Water Resistance>

10 sheets of commercially available tissue were placed under the absorbent sheet, and a water column of physiological saline solution made by utilizing a glass tube of 20 mm diameter was built covering the openings filled with highly absorbent material to measure the water resistance pressure. At the portion which was filled with the highly absorbent material, the SAP was observed to mount due to its swelling, and although the water column was raised up to 800 mm H$_2$O, the liquid did not leak out to wet the tissue.

Example 20

<Preparing a Substrate for Liquid Impervious Sheet Material>

Hot melt type adhesive was sprayed on the surface of a matte-finished polyethylene sheet of 25 microns composed of LLDPE, and a spun-lace non-woven fabric having a high elasticity in the cross direction composed of PP staple fiber (1.5 denier×35 mm length) was laid on the sprayed surface of the polyethylene sheet and pressed together as heated to be bonded to prepare a composite of the non-woven fabric and the film having a structure as shown in FIG. 42A.

This composite was treated in a process shown in FIG. 42. First, the composite was made to pass on a grid roll (crest pitch 10 mm, width of top 0.5 mm, and depth 2 mm) of stainless steel whose surface temperature was 100° C. to make linear grooves formed on the film (step B of FIG. 42), ad then laterally extended 1.5 times to obtain a composite of the non-woven fiber and the film with the film portion and the non-woven exposed in bands (step C of FIG. 42).

<Preparing a Slurry of Absorbent Material>

Ethanol and water were added to a water dispersion liquid of 5% BC gel (made by Ajinomoto Corporation under the trademark "Biocellulose") to prepare one liter of 0.4% dispersion liquid of ethanol/water=60/40. To this dispersion liquid the SAP particles (made by Mitsubishi Chemical Co., Ltd.

under the trademark "US 40") of 0.3 mm average particle diameter were added to prepare a co-dispersion slurry of the SAP and the BC.
<Preparing an Absorbent Sheet>
The non-woven fabric and film composite was coated with the above-describe co-dispersion slurry in 200 g/m² weight and approximately 10 mm width in a way that the non-woven fabric portion was covered (step D of FIG. 42).
<Preparing an Absorbent Composite Having Dents>
The above-described absorbent sheet was formed in a corrugated shape by means of a grooved guide, and was laid on a PE/PET spun-bond of 20 g/m² (made by Unitika Co., Ltd. under the trademark "ELVES") treated to be hydrophilic to make an absorbent with a topsheet (step E of FIG. 42).
<Evaluating the Air Permeability>
Air permeability tests (of a Garret type provided for in JIS P8117) were conducted on the above-described absorbent sheet with the result that the air permeability was good, 80 sec/100 cc.
<Wearing Tests of Absorbent Products>
10 pieces of baby diaper were made by attaching a gather and a fastening tape to the above-described absorbent sheet having dents, and wearing tests were conducted. With two pieces of baby diaper leakage occurred from the side portion, but no leakage occurred at all for the back side with any of the diapers.

Example 21

<Preparing a Water Resistant Material Having Dents and Projections>
An MS (melt-blown and spun-bond composite) non-woven fabric (18 g/m²) mainly composed of PP melt-blown (5 g/m²) and PP spun-bond (13 g/m²) was prepared. On the other hand, an apertured film made by providing openings of 2 mm diameter on PE film of 30 micron thickness mainly composed of LLDPE was prepared. A small amount of hot melt type adhesive was sprayed onto the apertured film, and a MS non-woven fabric was attached onto the sprayed side to obtain a composite sheet as shown in FIG. 43.
On this composite sheet a water column test was conducted in a procedure identical with the one applied in Example 19 above with the result that the value was approximately 200 mm $H_2O$.
<Preparing an Absorbent Slurry>
An absorbent slurry was prepared under the same conditions as in Example 19 above. The above-described composite of the MS non-woven fabric and the apertured film was, in a procedure identical with the one applied in Example 19 above, supplied with the apertured film side facing upward on a conveyor belt provided with a suction zone and the absorbent slurry was fed onto the composite. The composite was subjected to removal of the liquid component in the suction zone and the SAP particles as absorbent material were bonded to and filled in the exposed surface of the MS non-woven fabric by means of the MFC to obtain a absorbent sheet as shown in FIG. 44.
<Air Permeability of the Absorbent Sheet>
Air permeability test (based on the Garret test provided for in ES P8117) was conducted on the obtained absorbent sheet with the result that the air permeability was 160 sec/100 cc.
<Evaluating the Water Resistance of the Absorbent Sheet>
10 sheets of tissue paper commercially available on the market were placed under the above-described absorbent sheet, a column of physiological saline solution was built by using a glass tube of 20 mm diameter covering the openings which were filled with the SAP particles to measure the water resistance. The SAP in contact with physiological saline solution swelled to mount raising the water column up to 800 mm $H_2O$, but no liquid leaked nor the tissue wetted.

Example 22

<Varying Viscosity and Temperature of a Dispersion Slurry in a Process of Making a Composite>
FIG. 86 shows an example of a process of making a composite with the PG taken as an example showing the varying viscosity and temperature of a slurry in each step of the process. In this example a dispersion slurry was used where 30% SAP particles (made by Mitsubishi Chemical Co., Ltd. under the trademark "US 40") and 0.5% MFC (made by Tokushu Paper Mfg. Co., Ltd. under the trademark "S-MFC") were dispersed in a dispersion medium of PG/water=70/30.
In preparing the dispersion slurry, stirring was required for mixing and dispersing the SAP and the MFC, and in order to save energy for stirring the stirring was conducted at 30° C. and 400 rpm. The obtained dispersion slurry was guided to a storage tank provided with a cooling jacket, where the slurry was stored at 10° C. while it was stirred slowly at approximately 400 rpm, and from the storage tank was transferred to a coating header through a heating jacketed pipe by means of a Moino pump (made by Hyojin Pump Mfg. Co., Ltd.).
The coating header had a dwelling capacity of approximately 20 minutes and provided inside with a heating unit by a steam pipe. At this coating header, the temperature of the slurry was controlled at approximately 50° C. The heated slurry was supplied to a coating roll provided with a grid, and applied in 10 mm width at 1 mm interval onto a non-woven fabric. The non-woven fabric was TECCEL of 50 g/m² (made by Oji Paper Co., Ltd.). The amount of coating was approximately 150 g/m². The non-woven fabric with the coated surface facing upward was guided to steaming zones provided with a steam generator where adding of water and heating were performed, and then, was made to pass a reduced pressure suction zone where the PG and water were removed. Remaining PG and water were further removed as the coated non-woven fabric was dried in hot air of 130° C. to make an absorbent sheet.
<Embodiments of the Present Invention in Dispersing Process>
The SAP particles/MFC were dispersed in a water/PG dispersion medium to make a dispersion slurry. In a process of making a composite absorbent by forming the dispersion slurry, the SAP particles were bonded with each other and the SAP and the substrate were bonded by the strong hydrogen bonds of the MFC covering the surface of the SAP particles. Hydrogen bonds were only completed with the PG removed first and then moisture removed, in a mixed dispersion medium system having higher content of the PG. Also, since the boiling point of an aqueous solution of the PG becomes lower, as the content of water becomes higher, it is advantageous process-wise to have as much water as possible in the process for removing the PG.

TABLE 16

| | PG/water | | | | |
|---|---|---|---|---|---|
| | 90/10 | 80/20 | 70/30 | 60/40 | 50/50 |
| Boiling point (° C.) | 135 | 116 | 110 | 106 | 104 |

On the other hand, however, as, in a dispersion medium of PG/water, the content of water was raised in the ratio of PG/water, the dispersion slurry containing the SAP became less stable as it changed against time, as shown in the following Table:

TABLE 17

| PG/water | Duration of stability of slurry containing SAP confirmed | Changing condition |
|---|---|---|
| 80/20 | Longer than 24 hours | Not changed |
| 70/30 | Around 4 hours | Viscosity of system increased |
| 60/40 | Around 30 minutes | Viscosity of system rapidly increased |
| 50/50 | Around 5 minutes | Whole solidified |

Figure 88:
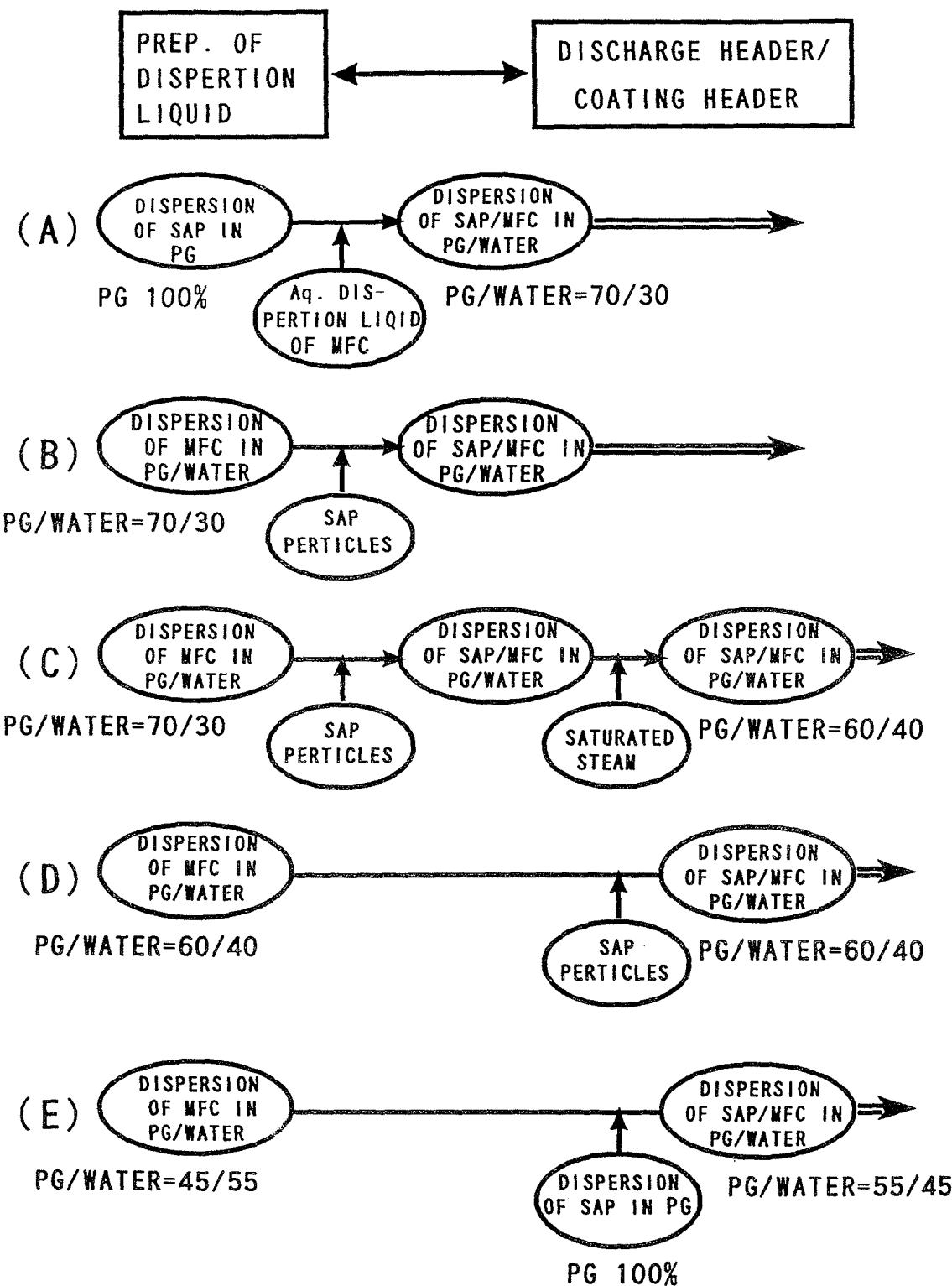
FIGS. 88(A) through (E) each are an explanatory drawing showing an embodiment of how the preparation of a dispersion slurry is carried out in each step leading to a coating header.

It is, therefore, important from the technical viewpoint how to replace the PG with water in the process. A first point of technical importance is how a system where the content of water is high can be adopted, and a second point of technical importance is how to replace the PG with water, after the slurry system is formed into a sheet. FIG. 88 shows an embodiment of the present invention showing in which steps the preparation of the dispersion slurry should be conducted leading to the slurry supplying zone of the forming process, i.e. the coating header.

Both of processes A and B are for preparing a dispersion slurry from a dispersion medium of PG/water=70/30. In process A, a water dispersion liquid of the MFC is added to a SAP dispersion liquid of 100% PG eventually to make the ratio of 70/30. Suspending is a simple process, but stirring is important because in adding a water dispersion liquid if the water ratio is higher locally, the SAP swells and the dispersion system becomes non-uniform.

In process B, after a PG/water dispersion liquid of the MFC is prepared at the mixed ratio of 70/30, the SAP particles are dispersed. Thus, a dispersion slurry can be prepared with relative ease.

In process C, when a slurry of mixed ratio of 70/30 obtained in the same way as applied in process B is heated at a coating header, heating and uniformly adding of water are carried out at the same time in a short period of time by adding steam directly, whereby the content of water is increased in a short period of time, that is to say, only during the dwelling time at the header, and the viscosity is much lowered and the liquidity is increased by the heating and adding of water for forming the coating.

In processes D and E embodying the present invention, an amount of water is made relatively larger in a short period of the dwelling time of the slurry by making the addition of the SAP particles immediately before the header. In process D, a case is conceived that the amount of water is made larger, i.e. the mixing ratio being 60/40, by adding the SAP particles immediately before the header. Process E attempts to prepare a dispersion slurry of higher water content, i.e. the mixing ratio being 55/45, by preparing higher water content dispersion liquid of the MFC and adding to the dispersion liquid and mixing a 100% PG dispersion liquid of the SAP so that a uniform mixing is realized in a short period of time immediately before the header.

<Embodiment of a Process of Removing the Liquid Component from PG/Water Dispersion Liquid System>

Embodiments of the present invention of preparing a dispersion slurry of PG/water of higher water content were described in the above. In order to efficiently remove the liquid component from a formed SAP sheet containing the PG and to have a higher content of water, such means are available as spraying water in droplets and making water stream flowing down the sheet in thin layer by means of a flow coater so that the PG is replaced with water. However, if such means is carelessly applied, the surface of the sheet may be non-uniform.

Figure 89:
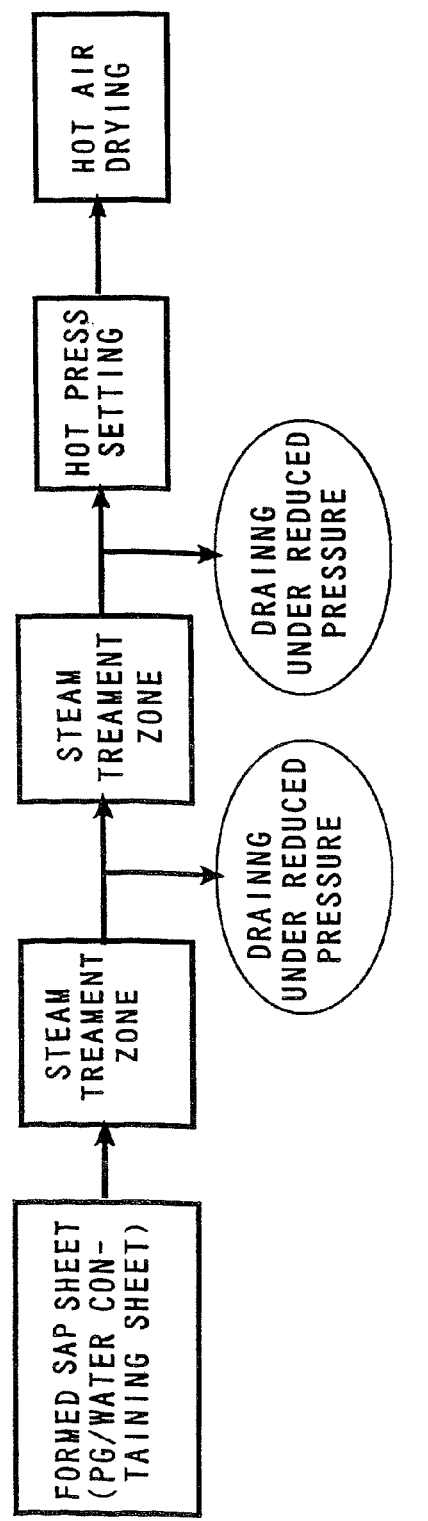
FIG. 89 is an explanatory drawing showing, with steam as a source of heating and hydrating, the order of a process consisting of removal of the liquid component by decompression in a liquid phase of a formed SAP sheet containing propylene glycol and removing the liquid component in a gaseous phase by hot air drying and fluctuations of propylene glycol/water composition and of residual quantity of propylene glycol.

FIG. 89 shows an example where steam is used in place of water stream as the source for adding water and heating. This is an embodiment of the present invention showing a means for removing the liquid component in the liquid phase by removing the liquid component under reduced pressure the formed SAP sheet containing the PG and for afterwards removing the liquid component in the gas phase by hot press and hot air. A SAP composite sheet formed on a substrate from the PG/water medium in slurry of mixed ratio of 70/30 is guided together with the substrate to a first steam treatment zone where heating and removing of the liquid component under reduced pressure are performed with the water content raised to approximately 50/50 and the residual amount of the PG lowered, and then guided to a second steam treatment zone. In the second steam treatment zone, further heating and removing of the liquid component under reduced pressure with the water content raised to approximately 30/70 are performed and part of the surface of the sheet is dried by hot press with the content of the PG lowered so that the surface of the sheet is stabilized, and with the surface thus stabilized and with the content of the PG further lowered, the sheet is guided into a hot air dryer to remove water together with the PG so that eventually the liquid removed and dried highly absorbent sheet of the present invention may be obtained. It should be noted that in FIG. 89 the residual amount of the PG is indicated as a relative value when the residual amount of the PG in a sheet immediately after it is formed is 100.

The above-described examples are designed to provide a system of making a highly absorbent sheet by utilizing a dispersion medium of a polyvalent alcohol and water as a dispersion medium of the SAP and by dexterously combining the viscosity and temperature characteristic of the dispersion medium in the configuration of the processes.

As described above, the absorbent composite of the present invention is such that the water swollen solid member contained in the structure can be formed in any shape such as powder, particle, pellet, sheet and any given three-dimensional structure and accordingly, the handling of the absorbent composite is made easier and the range of its applications is widened. When the SAP is utilized as such member and held stably in the network structure of the HFFM, not only the SAP can be used as it is in particles, but also an absorbent of any shape can be easily formed. Especially, formed in the shape of a sheet, the SAP can be made thin while having an extremely high capacity of absorbing water, and the thickness of absorbent products such as baby and adult diapers and feminine hygiene products can be minimized to the limits.

In the present invention in case an absorbent layer of a composite absorbent provided at least on either surface of a supporting sheet is composed of three components consisting of the SAP particles, the HFFM and short-cut staple fibers, the SAP particles among themselves and the top surface of layers formed by the SAP particles are covered in network structure by the short-cut staple fibers whose fiber length is longer than the diameter length of the SAP particles so that the SAP is taken in the network structure whereby, even when swollen with liquid, the swollen SAP particles can be prevented from coming off.

Further, the absorbent sheet of the present invention, unlike conventional absorbent sheets, can exhibit the capacity of absorbing quickly and stably many times body exudates discharged in varied ways and irregularly in terms of frequency depending upon environments and living conditions, in addition to being of excellent flexibility. Besides, the absorbent sheet of the present invention very quickly absorbs a discharged liquid first time, but also similarly very quickly absorbs second and third times of repeated discharging.

In addition, in case a dispersion medium system composed of a polyvalent alcohol system or a polyvalent alcohol/water system, polyvalent alcohol being highly viscous at low temperatures and logarithmically reduced in viscosity as heated, is used, forming and removing of the liquid component can easily be performed so that the efficiency of making highly absorbent sheets can be improved and the cost of making such sheets can be reduced.

What is claimed:

1. A method of making an absorbent sheet comprising the steps of:
   preparing a three component dispersion slurry by adding and dispersing a short-cut staple fiber component and absorbent polymer particles in a dispersion liquid where hydratable fine fibers in the form of microfibril are dispersed in a dispersion medium, the short-cut staple fiber component having longer fiber length than average diameter of the absorbent polymer particles;
   forming a slurry layer by spreading said three component dispersion slurry on at least either surface of a supporting sheet; and
   removing said dispersion medium from said slurry layer and then drying,
   wherein the ratio (P/Q) of weight (P) of said hydratable fine fibers in the form of microfibril to weight (Q) of said short-cut staple fiber component is in the range of from 1/5 to 5/1.

2. The method of claim 1, wherein said short-cut staple fiber component is thermally fusible fibers, and which further comprises the step of heating and melting said staple fiber component at the melting or higher temperatures, in or after said step of removing the dispersion medium.

3. A method of making an absorbent sheet comprising the steps of:
   preparing a two component dispersion liquid by dispersing hydratable fine fibers in the form of microfibril and absorbent polymer particles in a dispersion medium;
   forming a first slurry layer by spreading said two component dispersion liquid on at least either surface of a supporting sheet;
   forming a second slurry layer covering said first slurry layer by feeding a dispersion liquid where a short-cut staple fiber component is dispersed in a dispersion medium from the top of said first slurry layer, the short-cut staple fiber component having longer fiber length than average diameter of the absorbent polymer particles; and
   removing said dispersion mediums from said first and second slurry layers, and then drying,
   wherein the ratio (P/Q) of weight (P) of said hydratable fine fibers in the form of microfibril to weight (Q) of said short-cut staple fiber component is in the range of from 1/5 to 5/1.

4. A method of making an absorbent sheet comprising a supporting sheet, a first layer comprising two components of hydratable fine fibers in the form of microfibril and a short-cut staple fiber component, and a second layer comprising three components of absorbent polymer particles, hydratable fine fibers in the form of microfibril and a short-cut staple fiber component, said first and second layers being laid on at least one surface of said supporting sheet in a desired pattern, the short-cut staple fiber component having longer fiber length than average diameter of the absorbent polymer particles, comprising the steps of:
   forming a slurry layer by spreading a slurry where hydratable fine fibers in the form of microfibril and short-cut staple fiber component are dispersed in a dispersion medium so that said absorbent polymer particles on the supporting sheet are covered; and
   removing said dispersion medium from said slurry layer containing absorbent polymer particles and then drying,
   wherein the ratio (P/Q) of weight (P) of said hydratable fine fibers in the form of microfibril to weight (Q) of said short-cut staple fiber component is in the range of from 1/5 to 5/1.

5. A method of making an absorbent sheet comprising the steps of:
   preparing a dispersion liquid in the form of a slurry by dispersing absorbent polymer particles into a dispersion medium consisting of a water soluble polyvalent alcohol or a mixture of said alcohol with water;
   storing said dispersion liquid;
   forming said dispersion liquid into a sheet;
   removing said dispersion medium from said sheet; and
   drying said sheet to foam an absorbent body;
   wherein the viscosity of said dispersion liquid slurry is lowered by heating said dispersion liquid in succession in a process from a transfer of said dispersion liquid to said forming step up to said removing step, and said polyvalent alcohol is selected from a group consisting of ethylene glycol, propylene glycol, diethylene glycol, triethylene glycol, low molecular weight polyethylene glycol and glycerin.

6. The method of claim 5, wherein the viscosity is lowered by heating and adding an amount of water in the process leading up to the removing step.

7. The method of claim 5, wherein said dispersion medium is a mixture of a polyvalent alcohol and water, the ratio of the polyvalent alcohol to water being 9/1 to 5/5.

8. The method of claim 5, wherein the concentration of water to said polyvalent alcohol in said dispersion medium is increased in succession in said preparation step, said forming step and said removing step.

9. The method of claim 5, wherein said dispersion liquid contains hydratable fine fibers in the form of microfibril finer than the average particle diameter of the absorbent polymer particles coexistent with said absorbent polymer particles to make a co-dispersion system.

10. The method of claim 9, wherein said dispersion liquid in a liquid feeding step during said forming step is kept at a temperature of 30 C. or higher and 20 C. higher than the temperature in said storage step.

11. The method of claim 10, wherein heating in said liquid feeding step is done by directly blowing saturated steam so that the polyvalent alcohol/water ratio is adjusted by the effect of heating and water addition to said dispersion liquid during said liquid feeding.

12. The method of claim 5, wherein said dispersion liquid contains a short-cut staple fiber component having a length longer than the average particle diameter of said absorbent polymer particles and being fibrous material of 10 mm or shorter in fiber length and 3 denier or less in diameter.

13. The method of claim 5, wherein said dispersion liquid contains a combination of hydratable fine fibers in the form of microfibril shorter and finer than the average particle diameter of said absorbent polymer particles and a short-cut staple fiber component having a fiber length longer than the average particle diameter of said absorbent polymer particles and of 10 mm or shorter in length and 3 denier or less in diameter.

14. The method of claim 5, wherein the formed sheet obtained in said forming step is transferred to a steam treatment apparatus where heating of said formed sheet and water displacement are carried out whereby liquid removal is facilitated.

\* \* \* \* \*